United States Patent
Agoston et al.

(10) Patent No.: US 7,135,581 B2
(45) Date of Patent: Nov. 14, 2006

(54) ANTIANGIOGENIC AGENTS

(75) Inventors: Gregory E. Agoston, Germantown, MD (US); Jamshed H. Shah, Brookeville, MD (US); Kimberly A. Hunsucker, Germantown, MD (US); Victor S. Pribluda, Silver Spring, MD (US); Theresa M. LaVallee, Rockville, MD (US); Shawn J. Green, Vienna, VA (US); Christopher J. Herbstritt, Rockville, MD (US); Xiaoguo H. Zhan, Montgomery Village, MD (US); Anthony M. Treston, Rockville, MD (US)

(73) Assignee: Entremed, Inc., Rockville, MD (US)

( * ) Notice: Subject to any disclaimer, the term of this patent is extended or adjusted under 35 U.S.C. 154(b) by 0 days.

(21) Appl. No.: 09/939,208

(22) Filed: Aug. 24, 2001

(65) Prior Publication Data

US 2002/0082433 A1   Jun. 27, 2002

Related U.S. Application Data

(63) Continuation-in-part of application No. 09/933,894, filed on Aug. 21, 2001, now abandoned, which is a continuation-in-part of application No. 09/641,327, filed on Aug. 18, 2000.

(60) Provisional application No. 60/278,250, filed on Mar. 23, 2001, provisional application No. 60/255,302, filed on Dec. 13, 2000, provisional application No. 60/253,385, filed on Nov. 27, 2000.

(51) Int. Cl.
C07J 1/00 (2006.01)
C07J 41/00 (2006.01)
C07J 9/00 (2006.01)

(52) U.S. Cl. ............... 552/518; 552/519; 552/614; 552/522; 552/618; 552/662

(58) Field of Classification Search ............... 514/176, 514/171, 178, 179; 540/55; 424/238; 552/540, 552/618, 662, 518, 519, 614, 522
See application file for complete search history.

(56) References Cited

U.S. PATENT DOCUMENTS

| | | | |
|---|---|---|---|
| 2,584,271 A | 2/1952 | Huffman | |
| 2,846,453 A | 8/1958 | Hoehn | |
| 3,166,577 A | 1/1965 | Ringold et al. | |
| 3,410,879 A | 11/1968 | Smith et al. | |
| 3,470,218 A | 9/1969 | Farah | |
| 3,492,321 A | 1/1970 | Crabbe | |
| 3,496,272 A | 2/1970 | Kruger | |
| 3,562,260 A | 2/1971 | De Ruggieri et al. | |
| 3,950,437 A | 4/1976 | Imamura et al. | |
| 3,956,348 A | 5/1976 | Hilscher | |
| 4,172,132 A | 10/1979 | Draper et al. | |
| 4,212,864 A | 7/1980 | Tax | |
| 4,307,086 A | 12/1981 | Tax | |
| 4,444,767 A | 4/1984 | Torelli et al. | |
| 4,522,758 A | 6/1985 | Ward et al. | |
| 4,552,758 A | 11/1985 | Murphy et al. | |
| 4,634,705 A | 1/1987 | DeBernardis et al. | |
| 4,743,597 A | 5/1988 | Javitt et al. | |
| 4,808,402 A | 2/1989 | Leibovich et al. | |
| 4,994,443 A | 2/1991 | Folkman et al. | |
| 5,001,116 A | 3/1991 | Folkman et al. | |
| 5,135,919 A | 8/1992 | Folkman et al. | |
| 5,504,074 A | 4/1996 | D'Amato et al. | |
| 5,521,168 A | 5/1996 | Clark | |
| 5,621,124 A | 4/1997 | Seilz et al. | |
| 5,629,340 A | 5/1997 | Kuwano et al. | |
| 5,639,725 A | 6/1997 | O'Reilly et al. | |
| 5,643,900 A | 7/1997 | Fotsis et al. | |
| 5,661,143 A | 8/1997 | D'Amato et al. | |
| 5,716,981 A | 2/1998 | Hunter et al. | |
| 5,733,876 A | 3/1998 | O'Reilly et al. | |
| 5,763,432 A * | 6/1998 | Tanabe et al. | ............... 514/176 |
| 5,776,704 A | 7/1998 | O'Reilly et al. | |
| 5,792,845 A | 8/1998 | O'Reilly et al. | |
| 5,837,682 A | 11/1998 | Folkman et al. | |
| 5,854,205 A | 12/1998 | O'Reilly et al. | |
| 5,854,221 A | 12/1998 | Cao et al. | |
| 5,861,372 A | 1/1999 | Folkman et al. | |
| 5,885,795 A | 3/1999 | O'Reilly et al. | |

(Continued)

FOREIGN PATENT DOCUMENTS

DE   1907330   10/1969

(Continued)

OTHER PUBLICATIONS

Flshman et al., AN CA54:18587f CAOLD.*

(Continued)

Primary Examiner—Sabiha Qazi
(74) Attorney, Agent, or Firm—Kilpatrick Stockton LLP

(57) ABSTRACT

Compositions and methods for treating mammalian disease characterized by undesirable angiogenesis by administering derivatives of 2-methoxyestradiol of the general formula:

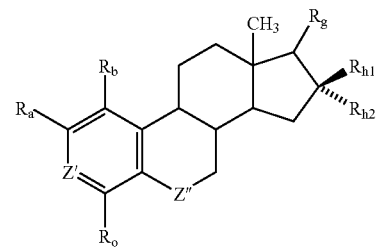

wherein the variables are defined in the specification.

2 Claims, No Drawings

U.S. PATENT DOCUMENTS

| | | | |
|---|---|---|---|
| 5,892,069 | A | 4/1999 | D'Amato et al. |
| 5,958,892 | A | 9/1999 | Mukhopadhyay et al. |
| 6,011,023 | A | 1/2000 | Clark et al. |
| 6,046,186 | A * | 4/2000 | Tanabe et al. ............ 514/178 |
| 6,051,726 | A | 4/2000 | Sachdeva et al. |
| 6,054,598 | A | 4/2000 | Sachdeva et al. |
| 6,136,992 | A * | 10/2000 | Ram et al. |
| 6,200,966 | B1 | 3/2001 | Stewart |
| 6,239,123 | B1 | 5/2001 | Green et al. |
| 6,284,789 | B1 | 9/2001 | LaLonde et al. |
| 6,358,940 | B1 | 3/2002 | Conney |
| 6,399,773 | B1 | 6/2002 | Liu et al. |
| 6,407,086 | B1 * | 6/2002 | Faarup et al. ............ 514/182 |
| 6,410,029 | B1 | 6/2002 | Mukhopadhyay et al. |
| 6,514,971 | B1 | 2/2003 | Thomas et al. |
| 6,528,676 | B1 | 3/2003 | D'Amato et al. |
| 6,605,622 | B1 | 8/2003 | Green et al. |
| 6,730,665 | B1 | 5/2004 | Maran et al. |
| 6,930,128 | B1 * | 8/2005 | D'Amato et al. ........... 514/511 |
| 2002/0035098 | A1 | 3/2002 | Slaga et al. |
| 2002/0068724 | A1 | 6/2002 | Slaga et al. |
| 2003/0027803 | A1 | 2/2003 | Slaga et al. |
| 2003/0036539 | A1 | 2/2003 | Slaga et al. |
| 2004/0053906 | A1 | 3/2004 | Slaga et al. |
| 2005/0014737 | A1 * | 1/2005 | Agoston et al. ............ 514/182 |
| 2005/0101573 | A1 * | 5/2005 | Faarup et al. ............. 514/129 |

FOREIGN PATENT DOCUMENTS

| | | |
|---|---|---|
| DE | 2 004 516 | 9/1970 |
| DE | 27 57 157 | 12/1977 |
| DE | 3625315 | 1/1998 |
| EP | 0166937 A2 | 8/1986 |
| GB | 857080 | 12/1960 |
| GB | 857081 | 12/1960 |
| GB | 1570597 | 7/1980 |
| JP | 39-5480 B | 4/1939 |
| JP | 41 000100 A | 1/1966 |
| JP | 42-928 B | 1/1967 |
| JP | 63090763 A | 4/1988 |
| SU | 1240038 A1 | 10/1996 |
| WO | WO 87/02367 A3 | 4/1987 |
| WO | WO 88/08002 A1 | 10/1988 |
| WO | WO 90/15816 A1 | 12/1990 |
| WO | WO 93/03729 | 3/1993 |
| WO | WO 93/19746 A1 | 10/1993 |
| WO | WO 95/04535 | 2/1995 |
| WO | WO 98/32763 A1 | 7/1998 |
| WO | WO 98/40398 | 9/1998 |
| WO | WO 99/01142 A1 | 1/1999 |
| WO | WO 99/22728 A1 | 5/1999 |
| WO | WO 99/33858 A3 | 7/1999 |
| WO | WO 99/33859 A2 | 7/1999 |
| WO | WO 99/35150 A3 | 7/1999 |
| WO | WO 00/07576 A2 | 2/2000 |
| WO | WO 00/10552 A2 | 3/2000 |
| WO | WO 00/66095 A2 | 11/2000 |
| WO | WO 00/68246 A1 | 11/2000 |
| WO | WO 01/27132 A1 | 4/2001 |
| WO | WO 01/85755 A1 | 11/2001 |

OTHER PUBLICATIONS

Fishman Jack, AN CA52:13765i CAOLD.*
Cushman et al., AN 1997:436019, HCAPLUS, J. of Medicinal Chemistry (1997), 40(15), 2323-2334.*
Aboulwafa et al., Synthesis and evaluation for uterotrophic and antiimplantation activities of 2-substituted estradiol derivatives, Steroids, vol./Iss: 57, pp. 199-204, Apr. 1992.
Blickenstaff et al., Synthesis of Some Analogs of Estradiol, Steroids, vol./Iss: 46(4,5), pp. 889-902, Oct. 1985.
Brandi et al., Bone endothelial cells as estrogen targets (Abstract only), Calcif. Tissue Int. vol./Iss: 53 (5), pp. 312-317, 1993.
Brueggemeier et al., 2-Methoxymethylestradiol: a new 2-methoxy estrogen analogs that exhibits antiproliferative activity and alters tubulin dynamics, Journal of Steroid Biochemistry & Molecular Biology, vol./Iss: 78, pp. 145-156, 2001.
Crabbe, P., Cotton effect on the styrene chromophore (Abstract only), Chem. Ind., vol./Iss: 27, pp. 917-918, 1969.
Dubey et al., Methoxyestradiols Meidate the Antimitogenic Effects of Estradiol on Vascular Smooth Muscle Cells via Estrogen Receptor-Independent Mechanisms, Biochemical and Biophysical Research Communications, vol./Iss: 278, pp. 27-33, 2000.
El-Tombary . Synthesis, Uterotropic, And Antiuterotrophic Activities of Some Estradiol Derivatives Containing Thiadiazole, Thiazoline, and Thiazolidinone Moieties, Arch. Pharm. Pharm. Med. Chem., vol./Iss: 330 (9-10), pp. 295-302, 1997.
Emons et al., Modulation der hypophysaren Sekretion von Luteinisierendem Hormon (LH) durch Ostrogene, Focus MHL, vol./Iss: 3, pp. 221-228, 1986.
Fanchenko et al., Characteristics of the guinea pig uterus estrogen receptor system (Abstract only), Byull.Eksp. Biol. Med., vol./Iss: 85 (4), pp. 467-470, 1978.
Fraser et al., Angiogenesis and its control in the female reproductive system (Abstract only), British Medical Bulletin, vol./Iss: 56 (3), pp. 787-797, 2000.
Gandhi et al., Mannich reaction of estrone, Journal of Indian Chem. Soc., vol./Iss: 39, pp. 306-308, 1962.
Hahnel et al., The Specificity of the Estrogen Receptor of Human Uterus, Journal of Steroid Biochemistry, vol./Iss: 4, pp. 21-31, 1973.
He et al., Novel Cytokine Release Inhibitors. Part II: Steroids, Bioorganic & Medicinal Chemistry Letters, vol./Iss: 8, pp. 2825-2828, 1998.
Hejaz et al., Synthesis and Biological Activity of the Superestrogen (E)-17Oximino-3-O-sulfamoyl-1,3,5(10)-estratriene: X-ray Crystal Structure of (E)-17-Oximino-3-hydroxy-1,3,5(10)-estratriene, Journal of Medicinal Chemistry, vol./Iss: 42 (16), pp. 3188-3192, 1999.
Holker et al., The Reactions of Estrogens with Benzeneseleninic Anhydride and Hexamethyldisilazane, J. Chem. Soc. Perkin Trans., vol./Iss: 1, pp. 1915-1918, 1982.
Hu, G. Neomycin inhibits angiogenin-induced angiogenesis (Abstract only) Proceedings of the National Academy of Sciences, USA, vol./Iss: 95(17), pp. 9791-9795, 1998.
Ikegawa et al., Immunoaffinity extraction for liquid chromatographic determination of equilin and its metabolites in plasma (Abstract only), Biomed. Chromatogr., vol./Iss: 10 (2), pp. 73-77, 1996.
Iriarte et al., Steroids (XCIV). Synthesis of 2-methyl and 1,2-dimethyl estrogens (Abstract only), Tetrahedron, vol./Iss: 3, pp. 28-36, 1958.
Jaggers et al., Potent Inhibitory effects of steroids in an in vitro model of angiogenesis (Abstract only), Journal of Endocrinology, vol./Iss: 150 (3), pp. 457-464, 1996.
Kovacs et al., Steroids. XXIII. Synthesis of 2- and 4-hydroxy and 2,4-dihydroxy derivatives of estrone and estradiol (Abstract only), Acta Phys.Chem., vol./Iss: 19 (3), pp. 287-290, 1973.
Kurebayashi et al., Paradoxical hormone responses KPL-1 breast cancer cells in vivo: a significant role of angiogenesis in tumor growth (Abstract only), Oncology, vol./Iss: 59 (2), pp. 158-165, 2000.
Lippert et al., The effects of A-ring and D-ring metabolites of estradiol on the proliferation of vascular endothelial cells, Life Sciences, vol./Iss: 67, pp. 1653-1658, 2000.
Loozen et al., An approach to the synthesis of 7.beta.-amino estrogens (Abstract only), Recl.: J.R. Neth.Chem. Soc., vol./Iss: 102 (10), pp. 433-437, 1983.
Lovely et al., 2-(Hydroxyalkyl)estradiols: Synthesis and Biological Evaluation, Journal of Medicinal Chemistry, vol./Iss: 39, pp. 1917-1923, 1996.
McCarthy-Morrogh, Differential Effects of Estrone and Estrone-3-O-Sulfamate Derivatives on Mitotic Arrest, Apoptosis, and Microtubule Assembly in Human Breast Cancer Cells, Cancer Research, vol./Iss: 60, pp. 5441-5450, Oct. 1, 2000.

Michel et al., Inhibition of synaptosomal high-affinity uptake of dopamine and serotonin by estrogen agonists and antagonists (Abstract only), *Biochem. Pharmacol.*, vol./Iss: 36 (19), pp. 3175-3180, 1987.

Morisaki et al., Steroids. LI. Aromatization reaction of the cross-conjugated dienone system by Zinc 9. (Abstract only), *Chem. Pharm. Bull.*, vol./Iss: 14 (8), pp. 866-872, 1966.

Mueck et al., Angiogenetic and anti-angiogenetic effects of estradiol and its metabolites (Abstract only), *Journal of Clinical and Basic Cardiology*, vol./Iss: 4 (2), pp. 153-155, 2001.

Nambara et al., Microbial transformation products derived from steriods. I. Synthesis of 1,2- and 3-dimethoxy-4-methylestratrienes (Abstract only), *Chem. Pharm. Bull.*, vol./Iss: 20 (2), pp. 336-342, 1972.

Numazawa et al., Novel and Regiospecific Synthesis of 2-Amino Estrogens via Zincke Nitration, *Steroids*, vol./Iss: 41 (5), pp. 675-682, 1983.

Omar et al., Synthesis, binding affinities and uterotrophic activity of some 2-substituted estradiol and ring-A-fused pyrone derivatives, *European Journal of Medicinal Chemistry*, vol./Iss: 29, pp. 25-32, 1994.

Pert et al., Preparations of 2,4-disubstituted estradiols (Abstract only), *Australian Journal of Chemistry*, vol./Iss: 42 (3), pp. 421-432, 1989.

Peters et al., 17-Desoxy Estrogen Analogues, *Journal of Medicinal Chemistry*, vol./Iss: 32 (7), pp. 1642-1652, 1989.

Pfeiffer et al., Are catechol estrogens obligatory mediators of estrogen action in the central nervous system? I. Characterization of pharmacological probes with different receptor binding affinities and catechol estrogen formation rates (Abstract only), *Journal of Endocrinology*, vol./Iss: 110 (3), pp. 489-497, 1986.

Sato et al., Natural estrogens induce modulation of microtubules in Chinese hamster V79 cells in culture (Abstract only), *Horm. Carcinog. II. Proceedings Int. Symp., 2nd (1996), Meeting*, pp. 454-457, 1996, 1994.

Shishkina et al., Synthesis and properties of condensed heterocyclic derivatives of estra-4, 9-dien-17.beta-ol-3-one (Abstract only), *Khim.-Farm. Zh.*, vol./Iss: 8 (1), pp. 7-11, 1974.

Singh et al., Inhibition of deoxyglucose uptake in MCF-7 breast cancer cells by 2-methoxyestrone and 2-methoxyestrone-3-O-sulfamate (Abstract only), *Molecular and Cellular Endocrinology*, vol./Iss: 160 (1-2), pp. 61-66, 2000.

Siracusa et al., The effect of microtubule- and microfilament-disrupting drugs on preimplantation mouse embryos (Abstract only), *Journal of Embryology and Experimental Morphology*, vol./Iss: 60, pp. 71-82, Dec. 1980.

Spyriounis et al., Copper (II) complex of an estradiol derivative with potent antiinflammatory properties (Abstract only), *Arch. Pharm.*, vol./Iss: 324 (9), pp. 533-536, 1991.

Wang et al., Photoaffinity labeling of human placental estradiol 17.beta.-dehydrogenase with 2- and 4-azidoestrone, 2- and 4-azidoestradiol (Abstract only), *Shengwu Huaxue Zazhi*, vol./Iss: 8 (6), pp. 715-718, 1992.

Wang et al., Synthesis of B-Ring Homologated Analogues that Modulate Tubulin Polymerization and Microtubule Stability, *Journal of Medicinal Chemistry*, vol./Iss: 43, pp. 2419-2429, 2000.

Wiese et al., Induction of the Estrogen Specific Mitogenic Response of MCF-7 Cells by Selected Analogues of Estradiol-17β. A 3D QSAR Study, *Journal of Medicinal Chemistry*, vol./Iss: 40, pp. 3659-3669, 1997.

Wurtz et al., Three-Dimensional Models of Estrogen Receptor Ligand Binding Domain Complexes, Based on Related Crystal Structures and Mutational and Structure-Activity Relationship Data, *Journal of Medicinal Chemistry*, vol./Iss: 41, pp. 1803-1814, 1998.

Gujjar et al., The Effect of Estradiol on *Candida albicans* Growth, *Annals of Clinical and Laboratory Science*, vol./Iss: 27 (2), pp. 151-156, 1997.

Li, J., et al., (DN 103:65176) Catechol Formation of Fluoro- and Bromo-substituted Estradiols by Hamster Liver Microsomes. Evidence for Dehalogenation. (Abstract only), *CAPLUS: Molecular Pharmacology*, vol./Iss: 27 (5), pp. 559-565, 1985.

Nambara, T., et al., DN 82:43650; Analytical Chemical Studies on Steroids. LXXIII. Synthesis of Epimeric 2-Hydroxy-16-Chlorestrong Monomethyl Ethers (Abstract only), *HCAPLUS-Chemical and Pharmaceutical Bulletin*, vol./Iss: 22 (10), pp. 2455-2457, 1974.

Yasuda et al., Accelerated differentiation in seminiferous tubules of fetal mice prenatally exposed to ethinyl estradiol (Abstract only), *Anat. Embryol. (Berl.)*, vol./Iss: 174 (3), pp. 289-299, 1986.

Wheeler et al., Mitotic Inhibition and Chromosome Displacement Induced by Estradiol In Chinese Hamsters Cells, *Cell Motility and the Cytoskeleton*, vol./Iss: 7 (3), pp. 235-247, 1987.

Yue et al., 2-Methoxyestradiol, an Endogenous Estrogen Metabolite, Induces Apoptosis In Endothelial Cells and Inhibits Angiogenesis: Possible Role for Stress-Activated Protein Kinase Signaling Pathway and Fas Expression, *Molecular Pharmacology*, vol./Iss: 51, pp. 951-952, 1997.

Rao et al., Structural Specificity of Estrogens in the Induction of Mitotic Chromatid Non-Disjunction in Hela Cells, *Experimental Cell Research*, vol./Iss: 48, pp. 71-81, 1967.

Sakakibara, Kyoichi, 2-Hydroxy-1,3,5(10)-estratriene derivatives (abstract only) (Identifier: XP-002186126), *Chemical Abstracts*, vol./Iss: 60(1), Jan. 6, 1964.

Lilopriatone/(1-[4-(Dimethylamino)phenyl]-17-hydroxy-17-(3-hydroxy-1-propenyl) estra-4,9-diene-3-one; AK 98734.

(paragraphs 583-584), *The Merck Index 11th Edition*, pp. 88, 1969.

Adams, E.F. et al., Steroidal regulation of oestradiol-17B dehydrogenase activity of the human breast cancer cell line MCF-7, *Journal of Endocrinology*, vol./Iss: 188 (1), pp. 149-154, Jul. 1988.

Aizu-Yokota et al. Natural Estrogens Induce Modulation of Microtubules in Chinese Hamster V79 Cells In Culture, *Cancer Research*, vol./Iss: 55, pp. 1863-1868, May 1, 1995.

Attalia et al., 2-Methoxyestradiol Arrests Cells In Mitosis without Depolarizing Tubulin, *Biochemical and Biophysical Research Communications*, vol./Iss: 228, pp. 467-473, 1996.

Ayala et al., The Induction of Accelerated Thymic Programmed Cell Death During Polymicrobial Sepsis: Control by Corticosteriods but not Tumor Necrosis Factor (Abstract only), *Shock*, vol./Iss: 3 (4), pp. 259-267, Apr. 1995.

Banik et al., Orally Active Long-Acting Estrogen (3-(2-propynyloxy)-estra-1,3,5,(10)-triene-17. beta.-ol trimethylacetate) (Identifier only), *Steroids*, vol./Iss: 16 (3), pp. 289-296, 1970

Bardon et al., Steroid Receptor-Mediated Cytotoxicity of an Antiestrogen and an Antiprogestin in Breast Cancer Cells (Abstract only), *Cancer Research*, vol./Iss: 47 (5), pp. 1441-1448, Mar. 1, 1987.

Bhat et al., Estradiol-Induced Mitotic Inhibition in the Buraa of Fabriclus of Male Domestic Duckling, *Mikroskopie*, vol./Iss: 39, pp. 113-117, May 1982.

Blagosklonny et al., Raf-1/bcl-2 Phosphorylation: A Step from Microtubule Damage to Cell Death, *Cancer Research*, vol./Iss: 57, pp. 130-135, Jan. 1, 1997.

Blickenstaff et al., Estrogen-Catharanthus (Vinca) Alkaloid Conjugates, *Cytotoxic Estrogens in Hormone Receptive Tumors*, pp. 89-105, 1980.

Boye et al., 185. Deaminocolchinyl Methyl Ether: Synthesis from 2,3,4,4'-Tetramethoxybiphenyl-2-carbaldehyde. Comparison of Antitubulin Effects of, *Helvetica Chimica Acta*, vol./Iss: 72, pp. 1690-1696, 1989.

Brodie, A.M., Aromatase Inhibitors in the Treatment of Breast Cancer (Abstract only), *Journal of Steroid Biochemistry and Molecular Biology*, vol./Iss: 49 (4-6), pp. 281-287, Jun. 1994.

Brosens et al., Comparative Study of the Estrogenic Effect of Ethinylestradiol and Mestranol on the Endometrium, *Laboratory for Gynecological Physiopathology*, vol./Iss: 14 (6), pp. 679-685, Dec. 1, 1976.

Castagnetta, L. et al., Simple Approach to Measure Metabolic Pathways of Steroids In Living Cells, *Journal of Chromatography*, vol./Iss: 572, pp. 25-39, Dec. 6, 1991.

Chasserot-Golaz et al., Biotransformation of 17.beta.-hydroxy-11.beta.-(4-dimethylaminophenyl)17.alpha.1-propynyl-estra-4,9-diene-3-one (RU486) In Rat Hepatoma Variants (Identifier only), *Biochemical Pharmacology*, vol./Iss: 46 (11), pp. 2100-2103, Jan. 1, 1993.

Chen et al., A New Synthetic Route to 2- and 4-Methoxyestradiols by Nucleophilic Substitution, *Steroids*, vol./Iss: 47 (1), pp. 63-66, Jan. 1986.

Chen et al., Synthesis of 11.beta.-(4-dimethylaminophenyl)-17.beta-hydroxy-17.alpha.-(1-propyl) estra-4, 9-dien-3-one (RU486) (Identifier only), *Nanjing Yaoxueyuan Xuebao*, vol./Iss: 17 (4), pp. 282-285, 1986.

Cohen et al., Novel Total Synthesis of (+)-Estrone 3-Methyl Ether, (+)-13B-Ethyl-3-methoxygona-1,3,5(10-triane-17-one, and (+)-Equilenin 3-Methyl Ether, *The Journal of Organic Chemistry*, vol./Iss: 6, pp. 681-685, Mar. 21, 1975.

Collins et al., The Structure and Function of Estrogens. XI* Synthesis of (+/−)-7(8-1α)abeo-Estradiol and its 9,11-Didehydro Derivative, *Aust. Journal of Chemistry*, vol./Iss: 45, pp. 71-97, 1992.

Crum, R. et al., A New Class of Steroids Inhibits Angiogenesis in the Presence of Heparin or a Heparin Fragment, *SCIENCE*, vol./Iss: 230, pp. 1375-1378, Dec. 20, 1985.

Cummings et al., Apoptosis, *The American Journal of Surgical Pathology*, vol./Iss: 21 (1), pp. 88-101, 1997.

Cushman et al., Synthesis, Antitubulin and Antinitotic Activity, and Cytotoxicity of Analogs of 2-Methoxyestradiol, an Endogenous Mammalian Metabolite of Estradiol that, *Journal of Medical Chemistry*, vol./Iss: 38 (12), pp. 2041-2049, 1995.

Cushman et al., Synthesis of Analogs of 2-Methoxyestradiol with Enhanced Inhibitory Effects of Tubulin Polymerization and Cancer Cell Growth, *Journal of Medical Chemistry*, vol./Iss: 40 (15), pp. 2323-2334, 1997.

D'Amato et al., 2-Methoxyestradiol, an Endogenous Mammalian Metabolite, Inhibits Tubulin Polymerization by Interacting at the Colchicine Site, *Proceedings of the National Academy of Science USA*, vol./Iss: 91, pp. 3964-3968, Apr. 1994.

Dvir et al., Thin-layer Chromatography of DANSYL-oestrogens, *Journal of Chromatography*, vol./Iss: 52, pp. 505-506, Nov. 4, 1970.

Epe et al., Microtubular Proteins as Cellular Targets for Carchogenic Estrogens and Other Carcinogens, *Mechanisms of Chromosome Distribution and Aneuploidy*, pp. 345-351, 1989.

Evans et al., A Convergent Total Synthesis of (+)- Colchicine and (+)-Desacetamidolsocolchicine, *Journal of the American Chemical Society*, vol./Iss: 103, pp. 5813-5821, Sep. 23, 1981.

Fishman, J., Synthesis of 2-Methoxyestrogens, *Journal of the American Chemical Society*, vol./Iss: 80, pp. 1213-1216, Mar. 5, 1998.

Fitzgerald, Molecular Features of Colchicine Associated with Antimitotic Activity and Inhibition of Tubulin Polymerization, *Biochemical Pharmacology*, vol./Iss: 25, pp. 1383-1387, Jun. 15, 1976.

Fotsis et al., The Endogenous Oestrogen Metabolite 2-Methoxyestradiol Inhibits Angiogenesis and Suppresses Tumour Growth, *Nature*, vol./Iss: 368, pp. 237-239, Mar. 17, 1994.

Getahun et al., Synthesis of Alkoxy-Substituted Diaryl Compounds and Correlation of Ring Separation with Inhibition of Tubulin Polymerization: Differential Enhancement of Inhibitory Effects Under Suboptimal Polymerization, *Journal of Medical Chemistry*, vol./Iss: 35 (6), pp. 1058-1067, Mar. 20, 1992.

Gross et al., Inhibition of Tumor Growth, Vascularization, and Collagenolysis in the Rabbit Cornea by Medroxyprogesterone, *Proceedings of the National Academy of Science USA*, vol./Iss: 78 (2), pp. 1176-1180, Feb. 1981.

Guangrong et al., Effect of Components of Crowth Ether Copper(I)Iodide Mixed Catalyst on Nucleophilic Substitution of Bromoestrogen (Abstract No. 195225), *Chemical Abstracts*, vol./Iss: 111 (21), pp. 818, col. 1, Nov. 20, 1989.

Haldar et al., Bc12 is the Guardian of Microtubule Integrity, *Cancer Research*, vol./Iss: 57, pp. 229-233, Jan. 15, 1997.

Hamel et al., Interactions of 2-Methoxyestradiol, an Endogenous Mammalian Metabolite, with Unpolymerized Tubulin and with Tubulin Polymers, *Biochemistry*, vol./Iss: 35 (4), pp. 1304-1310, 1996.

Hartley-Asp et al., Diethylstibestrol Induces Metaphase Arrest and Inhibits Microtubule Assembly, *Mutation Research*, vol./Iss: 143 (4), pp. 231-235, Aug. 1985.

He et al., A Versatile Synthesis of 2-Methoxyestradiol, an Endogenous Metabolite of Estradiol which Inhibits Tubulin Polymerization by Binding to the Colchicine Biding Site, *Bioorganic & Medicinal Chemistry Letters*, vol./Iss: 4 (14), pp. 1724-1728, 1994.

Huber et al., Tubulin Binding of Conformationally Restricted Bis-Aryl Compounds, *Bioorganic & Medicinal Chemistry Letters*, vol./Iss: 1 (5), pp. 243-246, 1991.

Josefsson et al., Suppression of Type II Collagen-Induced Arthritis by the Endogenous Estrogen Metabolite 2-Methoxyestradiol, *Arthritis & Rheumatism*, vol./Iss: 40 (1), pp. 154-163, Jan. 1997.

Kabarity et al., Further Investigations on the cytological effects of some contraceptives, *Mutation Research*, vol./Iss: 135, pp. 181-188, 1964.

Kelly et al., The Stimulation of Prostaglandin Production by Two Antiprogesterone Steroids in Human Endometrial Cells (Abstract only), *Journal of Clinical Endocrinology Metabolism*, vol./Iss: 62 (6), pp. 1116-1123, Jun. 1986.

Klauber et al., Inhibition of Angiogenesis and Breast Cancer in Mice by the Microtubufe Inhibitors 2-Methoxyestradiol and Taxol, *Cancer Research*, vol./Iss: 57, pp. 81-86, Feb. 1, 1997.

Lebras, J. et al., Activation and Regioselective Ortho-Functionalization of the A-Ring of B-Estradiol Promoted by "Cp'Ir": An Efficient Organometallic Procedure for the Synthesis of 2-Methoxyestradiol, *Organometallics*, vol./Iss: 16, pp. 1765-1771, 1997.

Lin et al., Interactions of Tubulin with Potent Natural and Synthetic Analogs of the Antimitotic Agent Combretastatin: A Structure-Activity Study, *Molecular Pharmacology*, vol./Iss: 34 (2), pp. 200-208, Aug. 1988.

Lincoln et al., Conformation of Thiocolchicine and Two 8-Ring-Modified Analogues Bound to Tubulin Studied with Optical Spectroscopy, *Biochemistry*, vol./Iss: 30 (5), pp. 1179-1187, Feb. 5, 1991.

Lottering et al., Effects of the 17β-Estradiol Metabolites on Cell Cycle Events in MCF-7 Cells, *Cancer Research*, vol./Iss: 52, pp. 5926-5932, Nov. 1, 1992.

Lottering et al., 17β-Estradiol Metabolites Affect Some Regulators of the MCF-7 Cell Cycle, *Cancer Letters*, vol./Iss: 110, pp. 181-186, 1996.

Mayol et al., Ethynylestradiol-Induced Cell Proliferation in Rat Liver Involvement of Specific Populations of Hepatocytes (Abstract only), *Carcinogenesis*, vol./Iss: 12 (12), pp. 2381-2388, 1992.

Meikrantz et al., Apoptosis and the Cell Cycle, *Journal of Cellular Biochemistry*, vol./Iss: 58, pp. 160-174, Jun. 1995.

Miller et al., Synthesis and Structure-Activity Profiles of A-Homoestranes, the Estratropones, *Journal of Medicinal Chemistry*, vol./Iss: 40, pp.3836-3841, 1997.

Morgan et al., Calcium and Oestrogen Interactions upon the Rat Thymic Lymphocyte Plasma Membrane, *Biochemical and Biophysical Research Communications*, vol./Iss: 72 (2), pp. 663-672, Sep. 20, 1978.

Mukhopadhyay et al., Induction of Apoptosis in Human Lung Cancer Cells after Wild-Type p53 Activation by Methoxyestradiol, *Oncogene*, vol./Iss: 14, pp. 379-384, 1997.

Mukundan et al., Liver Regeneration In Oral Contraceptive Treated Female Rate—Effects of Moderate Malnutrition, *Hormone and Metabolic Research*, vol./Iss: 16, pp. 641-645, Dec. 1984.

Nakagawa-Yagi et al., The Endogenous Estrogen Metabolite 2-Methoxyestradiol Induces Apoptotic Neuronal Cell Death *In Vitro*, *Life Sciences*, vol./Iss: 58 (17), pp. 1461-1467, 1996.

Nakamura et al., Studies on the Total Synthesis of dl-Coichicine. I. Synthesis of 3-Hydroxy-9, 10, 11-trimethoxy-1,2,3,4,6,7-hexahydro-5H-dibenso[a,c] cycloheptatrien-5-one, *Chemical and Pharmaceutical Bulletin*, vol./Iss: 10, pp. 281-290, 1962.

Nambara et al., Studies on Steroid Conjugates. III. New Synthesis of 2-Methoxyestrogens, *Chem. Pharm. Bulletin*, vol./Iss: 18 (3), pp. 474-480, Mar. 1970.

Napolitano et al., 11 Beta-Substituted Estradiol Derivatives. 2. Potential Carbon-11 and Iodine-Labeled Probes for the Estrogen Receptor (Abstract only).

Nishigaki et al., Anti-Proliferative Effect of 2-Methoxyestradiol on Cultured Smooth Muscle Cells from Rabbit Aorta, *Atherosclerosis*, vol./Iss: 113, pp. 167-170, 1995.

Ochs et al., Effect of Tumor Promoting Contraceptive Steroids on Growth and Drug Metabolizing Enzymes in Rat Liver (Abstract only), *Cancer Research*, vol./Iss: 46 (3), pp. 1224-1232, 1988.

Oppolzer et al., 177. The Enantioselective Synthesis of (+)-Estradiol from 1,3-Dihydrobenzo[c] thiophene-2,2-dioxide by Successive Thermal $SO_2$-Extrusion and Cycloaddition Reactions, *Helvetica Chimica Acta*, vol./Iss: 63, pp. 1703-1707, 1980.

Parthasarathy et al., Antioxidant: A New Role for RU-486 and Related Compounds (Abstract only), *Journal of Clinical Investigation*, vol./Iss; 94 (5), pp. 1990-1995, Nov. 1994.

Paull et al., Identification of Novel Antimitotic Agents Acting at the Tubulin Level by Computer-assisted Evaluation of Differential Cytotoxicity Data, *Cancer Research*, vol./Iss: 52, pp. 3892-3900, Jul. 15, 1992.

Poli et al., Tumor Necrosis Factor α Functions in an Autocrine Manner in the Induction of Human Immunodefficiency Virus Expression, *Proceedings of the National Academy of Science USA*, vol./Iss: 87, pp. 782-785, Jan. 1990.

Ravindra, R., Effect of Estradiol on the *In vitro* Assembly of Rat Brain Tubulin, *Journal of Indian Institute of Science*, vol./Iss: 64 (3), pp. 27-35, Mar. 1983.

Sakakibara et al., Effects of Diethylstilbestrol and its Methl Ethers on Aneuploidy Induction and Microtubule Distribution in Chinese Hamster V79 cells, *Mutation Research*, vol./Iss: 263, pp. 269-276, Aug. 1991.

Sato et al., Effect of Estradiol and Ethynylestradiol on Microtubule Distribution in Chinese Hamster V79 Cells, *Chemical and Pharmaceutical Bulletin*, vol./Iss: 40 (1), pp. 182-184, Jan. 1992.

Sato et al., Disruptive Effect of Diethylstilbestrol on Microtubules, *Gann*, vol./Iss: 75, pp. 1046-1048, Dec. 1984.

Sawada et al., Colchicine-Like Effect of Diethylstilbestrol (DES) on Mammalian Cells in Vitro, *Mutation Research*, vol./Iss: 57, pp. 175-182, May 1978.

Seegers et al., Cyclic-AMP and Cyclic-GMP Production in MCF-7 Cells Exposed to Estradiol-17 Beta, Catecholestrogens and Methoxy-Estrogens in MCF-7 Cells (Meeting Abstract only), *Joint MCI-1st Symposium. Third 1st International Symposium. Biology and Therapy of Breast Cancer*, Sep. 25, 1989.

Seegers, J.C. et al., The Cytotoxic Effects of Estradiol-17Β, Catecholestradiols and Methoxyestradiols on Dividing MCF-7 and HeLa Cells, *Journal of Steroid Biochemistry*, vol./Iss: 32 (6), pp. 797-809, 1989.

Sharp et al., Diethylstilboestrol: the Binding and Effects of Diethylstilboestrol upon the Polymerization and Depolymerisation of Purified Microtubule Protein In vitro, *Carcinogens*, vol./Iss: 6 (6), pp. 865-871, Jun. 1985.

Spicer et al., Catecholestrogens Inhibit Proliferation and DNA Synthesis of Porcine Granulosa Cells In Vitro: Comparison with Estradiol, 5α-dihydrotestosterone, Gonadotropins and Catecholamines, *Molecular and Cellular Endocrinology*, vol./Iss: 64, pp. 119-126, 1989.

Sternlight et al., Colchicine Inhibition of Microtubule Assembly via Copolymer Formation, *The Journal of Biological Chemistry*, vol./Iss: 254 (20), pp. 10540-10550, Oct. 25, 1979.

Sun et al., Antitumor Agents. 139. Synthesis and Biological Evaluation of Thiocolchicine Analogs 5,6-Dihydro-6(S)-(acyloxy)-and 5,6-Dihydro-6(S)-[(acyloxy)methyl]-1,2,3-, *Journal of Medicinal Chemistry*, vol./Iss: 36, pp. 544-551, Mar. 5, 1993.

Sunagawa et al., Synthesis of Colchicine; Synthesis of d-Demelthyoxydeoxy-hexahydrocolchicine, *Chem. Pharm. Bulletin*, vol./Iss: 9, pp. 81-83, 1961.

Teranishi, M. et al., Methylation of Catechol Estrogen with Diazomethane, *Chemical and Pharmaceutical Bulletin*, vol./Iss: 31 (9), pp. 3309-3314, Sep. 1983.

Tishler et al., Microtubule-Active Drugs Taxol, Vinblastine, and Nocodazole Increase the Levels of Transcriptionally Active p53, *Cancer Research*, vol./Iss: 55, pp. 6021-6025, Dec. 15, 1995.

Tsutsui et al., Comparison of Human Versus Syrian Hamster Cells In Culture for Induction of Mitotic Inhibition, Binucleation and Multinucleation, Following Treatment with Four Aneuploidogens, *Toxicology in Vitro*, vol./Iss: 4 (1), pp. 75-84, 1990.

Utne et al., The Synthesis of 2- and 4-Fluoroestradiol, *Journal of Organic Chemistry*, vol./Iss: 33 (6), pp. 2469-2473, Jun. 1968.

Van Geerestein et al., Structure of 11.beta.-(4-(dimethylamino)phenyl)-17.beta.-hydroxy-17. alpha.-(2- propenyl) estra-4,9-dien-3-one (Identifier only), *Acta Crystall Ogr., Secl. C: Cryst. Struct. Commun.*, vol./Iss: C43 (2), pp. 319-322, 1987.

Van Tamelen et al., The Synthesis of Colchicine, *Tetrahedron*, vol./Iss: 14, pp. 8-34, Sep. 1961.

Wang, Z. et al., An Optimized Synthesis of 2-Methoxyestradiol, a Naturally Occurring Human Metabolite with Anticancer Activity, *Synth. Commun.*, vol./Iss: 28 (23), pp. 4431-4437, 1998.

Wheeler et al., Mitotic Inhibition and Aneuploidy Induction by Naturally Occurring and Synthetic Estrogens in Chinese Hamster Cells In Vitro, *Mutations Research*, vol./Iss: 171, pp. 31-41, 1968.

Wheeler et al. Mitotic Inhibition and Chromosome Displacement Induced by Estradiol In Chinese Hamsters Cells, *Cell Motility and the Cytoskeleton*, vol./Iss: 7 (3), pp. 235-247, 1987.

Yue et al., 2-Methoxyestradiol, an Endogenous Estrogen Metabolite, Induces Apoptosis In Endothelial Cells and Inhibits Angiogenesis: Possible Role for Stress-Activated Protein Kinase Signalling Pathway and Fas Expression, *Molecular Pharmacology*, vol./Iss: 51, pp. 951-952, 1997.

Arnold et al., Sweet Isovanilyl Derivatives: Synthesis and Structure-Taste Relationships of Conformationally Restricted Analogs (abstract only), *Journal of Agric. Food Chem.*, vol./Iss: 46(10), pp. 4002-4010, 1998.

Audier et al., Orientation de la fragmentation en spectrometrie de masse par Introduction de groupements fonctionnels. VII.—Etheylenecellals de ceto-2-steroides, *Bulletin De La Societe Chimique De France*, vol./Iss: 10, pp. 3088-3090, 1965.

Cambie et al., Aromatic Steroids. Part II. Chronium Trioxide Oxidation of Some Oestra-1,3-5(10)-trienes, *Journal of the Chemical Society*, vol./Iss: 9, pp. 1234-1240, 1969.

Fetizon et al., Synthesis of 2-keto steroids (abstract only) *Bull. Soc. Chim. FR*, vol./Iss: 8, pp. 3301-3306, 1968.

Lichtenauer et al., Zur Behandlung des Prostata-Karzinoma, *Deutsches medizinisches Journal*, vol./Iss: 23, pp. 248-249, Jan. 1972.

Limantsev et al., Effect of some estrogen structural analogs on the development of the mouse embryo (abstract only), *Akusk Jimekol.*, vol./Iss: 6, pp. 55-56, 1982.

Miller, Thomas, Tubulin as a Therapeutic Target (Abstract only), *Dissertations Abstracts International*, vol./Iss: 5907B, pp. 3454, 1998.

Rao et al., Structural Specificity of Estrogens in the Induction of Mitotic Chromatid Non-Disjunction in Hela Cells, *Experimental Cell Research*, vol./Iss: 48, pp. 71-81, 1967.

Sakakibara, Kyoichi, 2-Hydroxy-1,3,5(10)-estratriene derivatives (abstract only) (Identifier: XP-002186126), *Chemical Abstracts*, vol./Iss: 60(1), Jan. 6, 1964.

Registry No. 56933-77-8, *Chemical Abstracts*.
Registry No. 56933-78-9, *Chemical Abstracts*.
Registry No. 57380-15-1, *Chemical Abstracts*.
Registry No. 71782-94-0, *Chemical Abstracts*.
Registry No. 71782-95-1, *Chemical Abstracts*.
Registry No. 101277-11-6, *Chemical Abstracts*.
Registry No. 101429-40-7, *Chemical Abstracts*.
Registry No. 162853-20-5, *Chemical Abstracts*.

Algire, G.H. et al., Vascular reactions of normal and malignant tumors in vivo. I. Vascular reactions of mice to wounds and to normal and neoplastic transplants, *Journal of the National Cancer Institute*, vol./Iss: 6, pp. 73-85, Aug. 1945.

Aliev et al., 54929q Synthesis of cycloalkyl derivatives of dihydric phenols and their ethers, *Chemical Abstracts*, vol./Iss: 72, pp. 370, 1970.

Anstead et al., The Estradiol Pharmacophore: Ligand Structure-Estrogen Receptor Binding Affinity Relationships and a Model for the Receptor Binding Site, *Steroids*, vol./Iss: 62, pp. 268-303, 1997.

Attalla et al., 2-Methoxyestradiol-Induced Phosphorylation of Bcl-2: Uncoupling from JNK/SAPK Activation (Abstract only), *Biochemical and Biophysical Research Communications*, vol./Iss: 247 (3), pp. 616-619, Jun. 29, 1998.

Barnes et al., Tumor Necrosis Factor Production in Patients with Leprosy, *Infection and Immunity*, vol./Iss: 60 (4), pp. 1441-1446, Apr. 1992.

Bindra et al., Studies in Antifertility Agents.8.Seco Steroids. 2, 5,6-Secoestradiol and Some Related Compounds, *Journal of Medicinal Chemistry*, vol./Iss: 18 (9), pp. 921-925, 1975.

Brem, H, et al., Interstitial chemotherapy with drug polymer implants for the treatment of recurrent gliomas, *Journal of Neurosurgery*, vol/Iss: 74 pp. 441-446, Mar. 1, 1991.

Burrows, N.P., Thalidomide Modifies Disease, *British Medical Journal*, vol./Iss: 307 (6909), pp. 939-940, Oct. 9, 1993.

Cambie et al., Aromatic Steroids. Part I. Oxidation Products of 3-Methoxyestra-1,3,5(10)-triene- 17βyl Acetate, *J. Chem. Soc.*, pp. 2603-2608, 1968.

Corey et al., Applications of N,N-Dimethylhydrazones to Synthesis. Use in Efficient, Positionally and Stereochemically Selective C-C Bond Formation; Oxidative Hydrolysis to Carbonyl Compounds, *Tetrahedron Letters*, vol./Iss: 1, pp. 3-6, 1976.

Corey et al., Facile Conversion of N,N-Dimethylhydrazones to Cabonyl Compounds by Cupric Ion-Catalyzed Hydrolysis, *Tetrahedron Letters*, vol./Iss: 41, pp. 36678-3668, 1976.

D'Amato, R.J. et al., Thalidomide is an Inhibitor of Angiogenesis, *Proceedings of the National Academy of Science USA*, vol./Iss: 91, pp. 4082-4085, Apr. 1, 1994.

Ding et al., Sex Hormone-Binding Globulin Mediates Prostate Androgen Receptor Action via a Novel Signaling Pathway (Abstract only), *Endocrinology*, vol./Iss: 139 (1), pp. 213-218, 1998.

Durani et al., Seco-Oestradiols and Some Non-Steroidal Oestrogens: Structural Correlates of Oestrogenic Action, *Journal of Steroid Biochemistry*, vol./Iss: 11, pp. 67-77, 1979.

Eder et al., Synthese von Ostradiol (In German—No translation available), *Chem. Ber.*, vol./Iss: 109, pp. 2948-2953, 1976.

Fevig et al., A Short, Stereoselective Route to 16α(Substituted-alkyl)estradiol Derivatives, *Journal of Organic Chemistry*, vol./Iss: 52, pp. 247-251, 1987.

Field et al., Effect of Thalidomide on the Graft versus Host Reaction, *Nature*, vol./Iss: 211 (5055), pp. 1308-1310, Sep. 17, 1966.

Fieser et al., N-Methylformanilide, *Organic Synthesis Collective vol. 3*, vol./Iss: 3, pp. 590-591, 1955.

Folkman, J., Tumor Angiogenesis: Therapeutic Implications, *New England Journal of Medicine*, vol./Iss: 285 (21), pp. 1182-1186, Nov. 18, 1971.

Folkman, J. et al., Induction of Angiogenesis During the Transition from Hyperplasia to Neoplasia, *Nature*, vol./Iss: 339, pp. 58-61, May 4, 1989.

Folkman, J. et al., Tumor Behavior In Isolated Perfused Organs in vitro Growth and Metastases of Biopsy Material in Rabbit Thyroid and Canine Intestinal Segment, *Annals of Surgery*, vol./Iss: 164(3), pp. 491-502, Sep. 1, 1966.

Gadosy et al., Generation, Characterization, and Deprotonation of Phenol Radical Cations, *Journal of Physical Chemistry*, vol./Iss: 103, pp. 8834-8839, 1999.

Gaslini et al., Reaction of Eugenol with Synthesis Gas. Synthesis of 5,6,7,8-Tetrahydro-3-methoxy-2-napthol, *Journal of Organic Chemistry*, vol./Iss: 29 (5), pp. 1177-1180, May 1964.

Gimbrone, M.A. et al., Tumor Growth and Neovascularization: An Experimental Model Using the Rabbit Cornea, *Journal of the National Cancer Institute*, vol./Iss: 52(2), pp. 413-427, Feb. 1974.

Gimbrone, M.A. et al., Tumor dormancy *In vivo* by Prevention of Neovascularization, *Journal of Experimental Medicine*, vol./Iss: 136, pp. 261-276, 1972.

Gonzalez et al., Synthesis and Pharmacological Evaluation of BαEstradiol Derivatives, *Steroids*, vol./Iss: 40 (2), pp. 171-187, Sep. 1982.

Gross, J.L. et al., Modulation of Solid Tumor Growth in vivo by bFGF (Abstract only), *Proceedings of the American Association of Cancer Research*, vol./Iss: 31, pp. 79, Mar. 1990.

Gunzler, V., Thalidomide-A Therapy for the Immunological Consequences of HIV Infection? *Medical Hypothesis*, vol./Iss: 30 (2), pp. 105-109, Oct. 1989.

Gupta et al., Antifertility Agents. XIV. Secosteroids. VII. Synthesis of 2αand 2β, 6β-dimethyl- 3β-(p-hyroxyphenyl)-trans-bicycle[4.3.0]nonan-7-ones and some related compounds (Abstract only), *Indian Journal of Chemistry*, vol./Iss: 13 (7), pp. 759-760, 1975.

Gupta et al., Studies in Antifertility Agents. Part XVIII. 2α6β-Diethyl-3β-(p-hydroxyphenyl)-trans-bicyclo[4.3.0]nonan-7β-ol and 6β-methyl-3β-(p-hydroxyphenyl)-2α-propyl- trans-bicyclo[4.3.0]nonan-7β-ol (Abstract only), *Indian Journal of Chemistry*, vol./Iss: 19B (10), pp. 886-890, 1980.

Gutierrez-Rodriguez, Treatment of Refractory Rheumatoid Arthritis—The Thalidomide Experience et al., *The Journal of Rheumatology*, vol./Iss: 16 (2), pp. 158-163, Feb. 1989.

Gutierrez-Rodriguez, Thalidomide—A Promising New Treatment for Rheumatoid Arthritis O., *Arthritis and Rheumatism*, vol./Iss: 27 (10), pp. 1118-1121, Oct. 1984.

Han et al., Dehydroeplandrosterone and Dihydrotestosterone Recognition by Human Estrogenic 17β-Hydroxysteroid Dehydrogenase, *Journal of Biological Chemistry*, vol./Iss: 275 Iss 2, pp. 1105-1111, Jan. 14, 2000.

Handley et al., Chronic bullous disease of childhood and ulcerative colitis, *British Journal of Dermatology*, vol./Iss: 127 (40), pp. 67-68, Jul. 1, 1992.

Heney et al., Thalidomide treatment for chronic graft-versus-host disease, *British Journal of Haematology*, vol./Iss: 78 (1), pp. 23-27, May 1991.

Hori, A. et al., Suppression of Solid Tumor Growth by Immunoneutralizing Monoclonal Antibody Against Human Basic Fibroblasts Growth Factor, *Cancer Research*, vol./Iss: 51, pp. 6180-6184, Nov. 15, 1991.

Ingber, D. et al., Synthetic analogues of fumagillin that inhibit angiogenesis and suppress tumor growth, *Nature*, vol./Iss: 348, pp. 555-557, Dec. 6, 1990.

Jhingran et al., Studies in Antifertility Agents—Part XLI: Secosteroids-x: Syntheses of Various Stereoisomers of (+-)-2,6β-diethyl-7α-ethynyl-3-(p-hydroxyphenyl)-trans-bicyclo [4.3.0]nonan-7β-ol., *Steroids*, vol./Iss: 42 (6), pp. 627-634, 1983.

Karwat, Separation and Recovery of Hydrogen Sulfide from Hydrocarbon Mixture, *Caplus DE 1103310*, Sep. 2, 1959.

Kataoka et al., An Agent that Increases Tumor Suppressor Transgene Product Coupled with Systemic Transgene Delivery Inhibits Growth of Metastatic Lung Cancer in Vivo (Abstract only), *Cancer Research*, vol./Iss: 58 (21), pp. 4761-4765, Nov. 1998.

Kim, K.J. et al., Inhibition of Vascular Endothelial Growth Factor-induced Angiogenesis Suppresses Tumor Growth In Vivo, *Nature*, vol./Iss: 362, pp. 841-844, Apr. 29, 1993.

Knightton, D. et al., Avascular and Vascular Phases of Tumour Growth in the Chick Embryo, *British Journal of Cancer*, vol./Iss: 35, pp. 347-356, 1977.

Kole et al., Studies in Antifertility Agents. 11. Secosteroids.5. Synthesis of 9,11-Secoestradiol, *Journal of Medicinal Chemistry*, vol./Iss: 18 (7), pp. 765-766, 1975.

Lewis, Richard J., *Hawley's Condensed Chemical Dictionary*, pp. 577, Jan. 1993.

Lewis, Richard J., *Hawley's Condensed Chemical Dictionary*, pp. 128-129, Jan. 1993.

Lien, W. et al., The blood supply of experimental liver metastases. II. A Microcirculatory study of the normal and tumor vessels of the liver with the use of perfused silicone rubber, *Surgery*, vol./Iss: 68 (2), pp. 334-340, Aug. 1970.

Liu et al., Total Synthesis of (+–) -$\Delta^{9(12)}$-Capnellene, *Tetrahedron Letters*, vol./Iss: 26 (40), pp. 4847-4850, 1985.

Maro et al., Mechanism of Polar Body Formation in the Mouse Oocyte: An Interaction Between the Chromosomes, the Cytoskeleton and the Plasma Membrane, *Journal of Embryology and Experimental Morphology*, vol./Iss: 92, pp. 11-32, 1988.

Meza et al., Managing the Gastrointestinal Complications of AIDS, *Drug Therapy*, vol./Iss: 23 (11), pp. 74-83, Nov. 1993.

Naafs et al., Thalidomide Therapy An Open Trial, *International Journal of Dermatology*, vol./Iss: 24 (2), pp. 131-134, Mar. 1985.

Nambara et al., Synthesis of 16β-Oxygenated Catechol Estrogen Methyl Ethers, New and Potential Metabolites, *Chemical & Pharmaceutical Bulletin*, vol./Iss: 23 (7), pp. 1613-1616, Jul. 1975.

Newkome et al., Synthesis of Simple Hydrazones of Carbonyl Compounds by an Exchange Reaction, *Journal of Organic Chemistry*, vol./Iss: 31, pp. 677-681, Mar. 1966.

Nguyen, M. et al., Elevated Levels of the Angiogenic Peptide Basic Fibroblast Growth Factor in Urine of Bladder Cancer Patients, *Journal of the National Cancer Institute*, vol./Iss: 85 (3), pp. 241-242, Feb. 3, 1993.

Pakala et al., Modulation of Endothelial Cell Proliferation by Retinoid X Receptor Agonists, *European Journal of Pharmacology*, vol./Iss: 385 (2/3), pp. 255-261, Sep. 1999.

Peng et al., Synthesis and Optical Properties of Novel Unsymmetrical Conjugated Dendrimers, *Journal of the American Chemical Society*, vol./Iss: 122, pp. 6619-6623, 2000.

Powell et al., Investigation and Treatment of Orogenital Ulceration; studies on a Possible Mode of Action of Thalidomide, *British Journal of Dermatology*, vol./Iss: 113 Supp. 28, pp. 141-144, Jul. 1985.

Romanelli et al., Ethyl-o-Dimethylaminophenylacetate, *Organic Synthesis*, vol./Iss: 5, pp. 552.

Seegers et al., The Mammalian Metabolite, 2-methoxyestradiol, Affects P53 Levels and Apoptosis Induction in Transformed Cells but Not in Normal Cells (Abstract only), *Journal of Steroid Biochemistry and Molecular Biology*, vol./Iss: 62 (4), pp. 253-267, Jul. 1997.

Shah et al., (+/−)-(N-alkylamino)benzazepine Analogs: Novel Dopamine DI Receptor Antagonists, *Journal of Medicinal Chemistry*, vol./Iss: 38 (21), pp. 4284-4293, Oct. 13, 1995.

Sidky et al., Inhibition of Angiogenesis by Interferons: Effects on Tumor- and Lymphocyte-induced Vascular Responses, *Cancer Research*, vol./Iss: 47, pp. 5155-5161, Oct. 1, 1987.

Srivastava, A. et al., The Prognostic Significance of Tumor Vascularity in Intermediate-Thickness (0.76-4.0mm Thick) Skin Melanoma, *American Journal of Pathology*, vol./Iss: 133 (2), pp. 419-424, Nov. 1988.

Starkov et al., Mono- and Dialkylation of Guaiacol by Olefins on KU-2 Cation Exchanger (Abstract only), *Zhumal Prikiadnoi Khimji*, vol./Iss: 41 (3), pp. 688-690, 1968.

Taylor, S. et al., Protamine is an Inhibitor of Angiogenesis, *Nature*, vol./Iss: 297, pp. 307-312, May 27, 1982.

Tremblay et al., A Convenient Synthetic Method for Alpha-Alkylation of Steroidal 17-Ketone: Preparation of 16β-(THPO-Heplyl)-Estradiol, *Synthetic Communications*, vol./Iss: 25 (16), pp. 2483-2495, 1995.

Tremblay et al., Synthesis of 16-(Bromoalkyl)-Estradiols Having Inhibitory Effect on Human Placental Estradiol 17β-Hydroxysteroid Dehydrogenase (17βHSD Type 1), *Bioorganic & Medicinal Chemistry*, vol./Iss: 3(5), pp. 505-523, 1995.

Vicente et al., In Vitro Activity of Thalidomide Against Mycobacterium avium Complex, *Archives of Internal Medicine*, vol./Iss: 153 (4), pp. 534, Feb. 22, 1993.

Weidner, N. et al., Tumor angiogenesis: A New Significant and Independent Prognostic Indicator in Early-Stage Breast Carcinoma, *Journal of the National Cancer Institute*, vol./Iss: 84, pp. 1875-1887, Dec. 16, 1992.

Weidner, N. et al., Tumor Angiogenesis Correlates with Metastasis in Invasive Prostate Carcinoma, *American Journal of Pathologgy*, vol./Iss: 143 (2), pp. 401-409, Aug. 1993.

Weidner, N. et al., Tumor Angiogenesis and Metastasis-Correlation in Invasive Breast Carcinoma, *New England Journal of Medicine*, vol./Iss: 324 (1), pp. 1-8, Jan. 3, 1991.

Welsch et al., Staphylostatic Activity of Some New Diphenols, Napthols, and Chalcones (Abstract only), *Experientia*, vol./Iss: 11, pp. 350-351, 1955.

White et al., Treatment of Pulmonary Hemanglomatosis with Recombinant Interferon Alfa-2a, *The New England Journal of Medicine*, vol./Iss: 32 (18), pp. 1197-1200, May 4, 1989.

Zoubine et al., 2-Methoxyestradiol-Induced Growth Suppression and Lethality in Estrogen-Responsive MCF-7 Cells May Be Mediated by Down Regulation of p34cdc2 and Cyclic B1 Expression (Abstract only), *International Journal of Oncology*, vol./Iss: 15 (4), pp. 639-646, Oct. 1999.

\* cited by examiner

ANTIANGIOGENIC AGENTS

CROSS-REFERENCE TO RELATED APPLICATIONS

This application is a continuation-in-part of U.S. patent application Ser. No. 09/933,894, filed Aug. 21, 2001, now abandoned which is a continuation-in-part of U.S. patent application Ser. No. 09/641,327, filed Aug. 18, 2000; this application also claims the benefit of U.S. Provisional Application No. 60/253,385, filed Nov. 27, 2000, U.S. Provisional Application No. 60/255,302, filed Dec. 13, 2000, and U.S. Provisional Application No. 60/278,250, filed Mar. 23, 2001.

FIELD OF THE INVENTION

The present invention relates to treating disease states characterized by abnormal cell mitosis and to treating disease states characterized by abnormal angiogenesis and to treating disease states characterized by a combination of these events. More particularly, the present invention relates to analogs of 2-methoxyestradiol ($2ME_2$) and their effect on diseases characterized by abnormal cell mitosis and/or abnormal angiogenesis.

BACKGROUND OF THE INVENTION

Angiogenesis is the generation of new blood vessels into a tissue or organ. Under normal physiological conditions, humans and animals undergo angiogenesis only in very specific, restricted situations. For example, angiogenesis is normally observed in wound healing, fetal and embryonal development, and formation of the corpus luteum, endometrium and placenta.

Angiogenesis is controlled through a highly regulated system of angiogenic stimulators and inhibitors. The control of angiogenesis has been found to be altered in certain disease states and, in many cases, pathological damage associated with the diseases is related to uncontrolled angiogenesis. Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. Endothelial cells, lining the lumen of blood vessels, then protrude through the basement membrane. Angiogenic stimulants induce the endothelial cells to migrate through the eroded basement membrane. The migrating cells form a "sprout" off the parent blood vessel where the endothelial cells undergo mitosis and proliferate. The endothelial sprouts merge with each other to form capillary loops, creating a new blood vessel.

Persistent, unregulated angiogenesis occurs in many disease states, tumor metastases, and abnormal growth by endothelial cells. The diverse pathological disease states in which unregulated angiogenesis is present have been grouped together as angiogenic-dependent or angiogenic associated diseases.

One example of a disease mediated by angiogenesis is ocular neovascular disease. This disease is characterized by invasion of new blood vessels into the structures of the eye, such as the retina or cornea. It is the most common cause of blindness and is involved in approximately twenty eye diseases. In age-related macular degeneration, the associated visual problems are caused by an ingrowth of choroidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma, and retrolental fibroplasia. Other diseases associated with corneal neovascularization include, but are not limited to, epidemic keratoconjunctivitis, Vitamin A deficiency, contact lens overwear, atopic keratitis, superior limbic keratitis, and pterygium keratitis sicca. Other diseases associated with undesirable angiogenesis include Sjögren's syndrome, acne rosacea, phylectenulosis, syphilis, *Mycobacteria* infections, lipid degeneration, chemical burns, bacterial ulcers, fungal ulcers, *Herpes simplex* infection, *Herpes zoster* infections, protozoan infections, Kaposi's sarcoma, Mooren's ulcer, Terrien's marginal degeneration, marginal keratolysis, rheumatoid arthritis, systemic lupus, polyarteritis, trauma, Wegener's sarcoidosis, scleritis, Stevens-Johnson's disease, pemphigoid, and radial keratotomy.

Diseases associated with retinal/choroidal neovascularization include, but are not limited to, diabetic retinopathy, macular degeneration, sickle cell anemia, sarcoidosis, syphilis, pseudoxanthoma elasticum, Paget's disease, vein occlusion, artery occlusion, carotid obstructive disease, chronic uveitis/vitritis, *Mycobacteria* infections, lyme's disease, systemic lupus erythematosis, retinopathy of prematurity, Eales' disease, Behcet's disease, infections causing retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications. Other eye-related diseases include, but are not limited to, diseases associated with rubeosis (neovascularization of the angle) and diseases caused by the abnormal proliferation of fibrovascular or fibrous tissue, including all forms of prolific vitreoretinopathy.

Another angiogenesis associated disease is rheumatoid arthritis. The blood vessels in the synovial lining of the joints undergo angiogenesis. In addition to forming new vascular networks, the endothelial cells release factors and reactive oxygen species that lead to pannus growth and cartilage destruction. Angiogenesis may also play a role in osteoarthritis. The activation of the chondrocytes by angiogenic-related factors contributes to the destruction of the joint. At a later stage, the angiogenic factors promote new bone growth. Therapeutic intervention that prevents the bone destruction could halt the progress of the disease and provide relief for persons suffering with arthritis.

Chronic inflammation may also involve pathological angiogenesis. Such diseases as ulcerative colitis and Crohn's disease show histological changes with the ingrowth of new blood vessels and the inflamed tissues. Bartonelosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

The hypothesis that tumor growth is angiogenesis-dependent was first proposed in 1971. (Folkman, *New Eng. J Med.*, 285:1182–86 (1971)). In its simplest terms, this hypothesis states: "Once tumor 'take' has occurred, every increase in tumor cell population must be preceded by an increase in new capillaries converging on the tumor." Tumor 'take' is currently understood to indicate a prevascular phase of tumor growth in which a population of tumor cells occupying a few cubic millimeters volume, and not exceeding a few million cells, can survive on existing host microvessels. Expansion of tumor volume beyond this phase requires the induction of new capillary blood vessels. For example, pulmonary micrometastases in the early prevascular phase in mice would be undetectable except by high power microscopy on histological sections.

Examples of the indirect evidence which support this concept include:

(1) The growth rate of tumors implanted in subcutaneous transparent chambers in mice is slow and linear before neovascularization, and rapid and nearly exponential after neovascularization. (Algire, et al., *J. Nat. Cancer Inst.,* 6:73–85 (1945)).

(2) Tumors grown in isolated perfused organs where blood vessels do not proliferate are limited to 1–2 mm$^3$ but expand rapidly to >1000 times this volume when they are transplanted to mice and become neovascularized. (Folkman, et al., *Annals of Surgery,* 164:491–502 (1966)).

(3) Tumor growth in the avascular cornea proceeds slowly and at a linear rate, but switches to exponential growth after neovascularization. (Gimbrone, Jr., et al., *J. Nat. Cancer Inst.,* 52:421–27 (1974)).

(4) Tumors suspended in the aqueous fluid of the anterior chamber of the rabbit eye remain viable, avascular, and limited in size to <1 mm$^3$. Once they are implanted on the iris vascular bed, they become neovascularized and grow rapidly, reaching 16,000 times their original volume within 2 weeks. (Gimbrone, Jr., et al., *J. Exp. Med.,* 136:261–76).

(5) When tumors are implanted on the chick embryo chorioallantoic membrane, they grow slowly during an avascular phase of >72 hours, but do not exceed a mean diameter of 0.93+0.29 mm. Rapid tumor expansion occurs within 24 hours after the onset of neovascularization, and by day 7 these vascularized tumors reach a mean diameter of 8.0+2.5 mm. (Knighton, *British J. Cancer,* 35:347–56 (1977)).

(6) Vascular casts of metastases in the rabbit liver reveal heterogeneity in size of the metastases, but show a relatively uniform cut-off point for the size at which vascularization is present. Tumors are generally avascular up to 1 mm in diameter, but are neovascularized beyond that diameter. (Lien, et al., *Surgery,* 68:334–40 (1970)).

(7) In transgenic mice which develop carcinomas in the beta cells of the pancreatic islets, pre-vascular hyperplastic islets are limited in size to <1 mm. At 6–7 weeks of age, 4–10% of the islets become neovascularized, and from these islets arise large vascularized tumors of more than 1000 times the volume of the pre-vascular islets. (Folkman, et al., *Nature,* 339:58–61 (1989)).

(8) A specific antibody against VEGF (vascular endothelial growth factor) reduces microvessel density and causes "significant or dramatic" inhibition of growth of three human tumors which rely on VEGF as their sole mediator of angiogenesis (in nude mice). The antibody does not inhibit growth of the tumor cells in vitro. (Kim, et al., *Nature,* 362:841–44 (1993)).

(9) Anti-bFGF monoclonal antibody causes 70% inhibition of growth of a mouse tumor which is dependent upon secretion of bFGF as its only mediator of angiogenesis. The antibody does not inhibit growth of the tumor cells in vitro. (Hori, et al., *Cancer Res.,* 51:6180–84 (1991)).

(10) Intraperitoneal injection of bFGF enhances growth of a primary tumor and its metastases by stimulating growth of capillary endothelial cells in the tumor. The tumor cells themselves lack receptors for bFGF, and bFGF is not a mitogen for the tumors cells in vitro. (Gross, et al., *Proc. Am. Assoc. Cancer Res.,* 31:79 (1990)).

(11) A specific angiogenesis inhibitor (AGM-1470) inhibits tumor growth and metastases in vivo, but is much less active in inhibiting tumor cell proliferation in vitro. It inhibits vascular endothelial cell proliferation half-maximally at 4 logs lower concentration than it inhibits tumor cell proliferation. (Ingber, et al., *Nature,* 48:555–57 (1990)). There is also indirect clinical evidence that tumor growth is angiogenesis dependent.

(12) Human retinoblastomas that are metastatic to the vitreous develop into avascular spheroids which are restricted to less than 1 mm$^3$ despite the fact that they are viable and incorporate $^3$H-thymidine (when removed from an enucleated eye and analyzed in vitro).

(13) Carcinoma of the ovary metastasizes to the peritoneal membrane as tiny avascular white seeds (1–3 mm$^3$) These implants rarely grow larger until one or more of them becomes neovascularized.

(14) Intensity of neovascularization in breast cancer (Weidner, et al, *New Eng. J. Med.,* 324:1–8 (1991); Weidner, et al., *J Nat. Cancer Inst.,* 84:1875–87 (1992)) and in prostate cancer (Weidner, et al., *Am. J. Pathol.,* 143(2): 401–09 (1993)) correlates highly with risk of future metastasis.

(15) Metastasis from human cutaneous melanoma is rare prior to neovascularization. The onset of neovascularization leads to increased thickness of the lesion and an increased risk of metastasis. (Srivastava, et al., *Am. J. Pathol.,* 133: 419–23 (1988)).

(16) In bladder cancer, the urinary level of an angiogenic protein, bFGF, is a more sensitive indicator of status and extent of disease than is cytology. (Nguyen, et al., *J. Nat. Cancer Inst.,* 85:241–42 (1993)).

Thus, it is clear that angiogenesis plays a major role in the metastasis of cancer. If this angiogenic activity could be repressed or eliminated, then the tumor, although present, would not grow. In the disease state, prevention of angiogenesis could avert the damage caused by the invasion of the new microvascular system. Therapies directed at control of the angiogenic processes could lead to the abrogation or mitigation of these diseases.

Angiogenesis has been associated with a number of different types of cancer, including solid tumors and blood-borne tumors. Solid tumors with which angiogenesis has been associated include, but are not limited to, rhabdomyosarcomas, retinoblastoma, Ewing's sarcoma, neuroblastoma, and osteosarcoma. Angiogenesis is also associated with blood-borne tumors, such as leukemias, any of various acute or chronic neoplastic diseases of the bone marrow in which unrestrained proliferation of white blood cells occurs, usually accompanied by anemia, impaired blood clotting, and enlargement of the lymph nodes, liver and spleen. It is believed to that angiogenesis plays a role in the abnormalities in the bone marrow that give rise to leukemia tumors and multiple myeloma diseases.

One of the most frequent angiogenic diseases of childhood is the hemangioma. A hemangioma is a tumor composed of newly-formed blood vessels. In most cases the tumors are benign and regress without intervention. In more severe cases, the tumors progress to large cavernous and infiltrative forms and create clinical complications. Systemic forms of hemangiomas, hemangiomatoses, have a high mortality rate. Therapy-resistant hemangiomas exist that cannot be treated with therapeutics currently in use.

Angiogenesis is also responsible for damage found in heredity diseases such as Osler-Weber-Rendu disease, or heredity hemorrhagic telangiectasia. This is an inherited disease characterized by multiple small angiomas, tumors of blood or lymph vessels. The angiomas are found in the skin and mucous membranes, often accompanied by epitaxis (nose bleeds) or gastrointestinal bleeding and sometimes with pulmonary or hepatitic arteriovenous fistula.

What is needed, therefore, is a composition and method which can inhibit angiogenesis. What is also needed is a composition and method which can inhibit the unwanted growth of blood vessels, especially in tumors.

Angiogenesis is also involved in normal physiological processes, such as reproduction and wound healing. Angiogenesis is an important step in ovulation and also in implantation of the blastula after fertilization. Prevention of angiogenesis could be used to induce amenorrhea, to block ovulation, or to prevent implantation by the blastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Several compounds have been used to inhibit angiogenesis. Taylor, et al. (*Nature,* 297:307 (1982)) have used protamine to inhibit angiogenesis. The toxicity of protamine limits its practical use as a therapeutic. Folkman, et al. (*Science,* 221:719 (1983), and U.S. Pat. Nos. 5,001,116 and 4,994,443) have disclosed the use of heparin and steroids to control angiogenesis. Steroids, such as tetrahydrocortisol, which lack gluccocorticoid and mineralocorticoid activity, have been found to be angiogenic inhibitors.

Other factors found endogenously in animals, such as a 4 kDa glycoprotein from bovine vitreous humor and a cartilage derived factor, have been used to inhibit angiogenesis. Cellular factors, such as interferon, inhibit angiogenesis. For example, interferon alpha or human interferon beta have been shown to inhibit tumor-induced angiogenesis in mouse dermis stimulated by human neoplastic cells. Interferon beta is also a potent inhibitor of angiogenesis induced by allogeneic spleen cells. (Sidky, et al., *Cancer Res.,* 47:5155–61 (1987)). Human recombinant interferon (alpha/A) was reported to be successfully used in the treatment of pulmonary hemangiomatosis, an angiogenesis-induced disease. (White, et al., *New Eng. J. Med.,* 320:1197–1200 (1989)).

Other agents which have been used to inhibit angiogenesis include ascorbic acid ethers and related compounds. (Japanese Kokai Tokkyo Koho No.58-13 (1978)). Sulfated polysaccharide DS 4152 also inhibits angiogenesis. (Japanese Kokai Tokkyo Koho No. 63-119500). Additional anti-angiogenic compounds include Angiostatin® (U.S. Pat. Nos. 5,639,725; 5,792,845; 5,885,795; 5,733,876; 5,776,704; 5,837,682; 5,861,372, and 5,854,221) and Endostatin™ (U.S. Pat. No. 5,854,205).

Another compound which has been shown to inhibit angiogenesis is thalidomide. (D'Amato, et al., *Proc. Natl. Acad. Sci.,* 90:4082–85 (1994)). Thalidomide is a hypnosedative that has been successfully used to treat a number of angiogenesis-associated diseases, such as rheumatoid arthritis (Gutierrez-Rodriguez, *Arthritis Rheum.,* 27 (10):1118–21 (1984); Gutierrez-Rodriguez, et al., *J. Rheumatol.,* 16(2): 158–63 (1989)), Behcet's disease (Handley, et al., *Br. J. Dermatol.,* 127 Suppl, 40:67–8 (1992); Gunzler, *Med. Hypotheses,* 30(2):105–9 (1989)), graft versus host rejection (Field, et al., *Nature,* 211(55): 1308–10 (1966); Heney, et al., *Br. J. Haematol.,* 78 (1):23–7 (1991)), *Mycobacteria* diseases (Vicente, et al., *Arch. Intern. Med.,* 153(4):534 (1993)), *Herpes simplex* and *Herpes zoster* infections (Naafs, et al., *Int. J. Dermatol.,* 24(2):131–4 (1985)), chronic inflammation, ulcerative colitis (Meza, et al., *Drug Ther,* 23 (11): 74–80, 83 (1993); Powell, et al., *Br. J Dermatol.,* 113 Suppl 28: 141–4 (1985)), leprosy (Barnes, et al, *Infect. Immun.,* 60(4):1441–46 (1992)) and lupus (Burrows, *BMJ,* 307: 939–40 (1993)).

Although thalidomide has minimal side effects in adults, it is a potent teratogen. Thus, there are concerns regarding its use in women of child-bearing age. Although minimal, there are a number of side effects which limit the desirability of thalidomide as a treatment. One such side effect is drowsiness. In a number of therapeutic studies, the initial dosage of thalidomide had to be reduced because patients became lethargic and had difficulty functioning normally. Another side effect limiting the use of thalidomide is peripheral neuropathy, in which individuals suffer from numbness and disfunction in their extremities. Thus, improved methods and compositions are needed that are easily administered and capable of inhibiting angiogenesis.

What is needed are safe and effective treatments that do not create unwanted side effects.

2-Methoxyestradiol is an endogenous metabolite of estradiol ($E_2$) that has potent anti-proliferative activity and induces apoptosis in a wide variety of tumor and non-tumor cell lines. When administered orally, it exhibits anti-tumor and anti-proliferative activity with little toxicity. In vitro data suggests that 2-methoxyestradiol does not engage the estrogen receptor for its anti-proliferative activity and is not estrogenic over a wide range of concentrations, as assayed by estrogen dependant MCF-7 cell proliferation. However, the presence of demethylases in vivo and in vitro may metabolize this compound to 2-hydroxyestradiol, which has been shown to be estrogenic by several approaches. What is needed is a means to improve the bioavailability of estradiol or 2-methoxyestradiol and to reduce the formation of estrogenic 2-methoxyestradiol metabolities. What is also needed is a means to modify estradiol or 2-methoxyestradiol in such a way to prevent conversion into an estrogenic derivative, metabolic conjugation and conversion to estrone.

SUMMARY OF THE INVENTION

The present invention provides certain analogs of 2-methoxyestradiol that are effective in treating diseases characterized by abnormal mitosis and/or abnormal angiogenesis. Specifically the present invention relates to analogs of 2-methoxyestradiol that have been modified at the 2, 16 or 17 positions or combinations thereof. Compounds within the general formulae that inhibit cell proliferation are preferred. Compounds within the general formula that inhibit angiogenesis are also preferred. Preferred compositions may also exhibit a change (increase or decrease) in estrogen receptor binding, improved absorption, transport (e.g. through blood-brain barrier and cellular membranes), biological stability, or decreased toxicity. The invention also provides compounds useful in the method, as described by the general formulae of the claims.

A mammalian disease characterized by undesirable cell mitosis, as defined herein, includes but is not limited to excessive or abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying: rheumatoid arthritis, skin diseases, such as psoriasis, diabetic retinopathy and other ocular angiogenic diseases such as retinopathy of prematurity (retrolental fibroplasic), macular degeneration, corneal graft rejection, neovascular glaucoma and Osler Weber syndrome (Osler-Weber-Rendu disease). Other undesired angiogenesis involves normal processes including ovulation and implantation of a blastula. Accordingly, the compositions described above can be used to block ovulation and implantation of a blastula or to block menstruation (induce amenorrhea).

It is known that 2-methoxyestradiol ($2ME_2$), an endogenous metabolite of estradiol with no intrinsic estrogenic activity, is a potent antiproliferative agent that induces apoptosis in a wide variety of tumor and non-tumor cell lines. When administered orally, it exhibits antitumor and antiangiogenic activity with little or no toxicity. Currently, $2ME_2$ is in several phase-I and II clinical trials under the name PANZEM™.

A novel series of compounds have been prepared that retain the biological activities of $2ME_2$ but are expected to have reduced metabolism. Several analogs lack the hydroxyl moiety at position 17 and cannot be metabolized to 2-methoxyestrone or conjugated at that position. Another set of compounds have the 2-methoxy group replaced by moieties which cannot be de-methylated to yield the potentially-estrogenic 2-hydroxy derivatives. Contrary to what is observed with $2ME_2$, several of these new analogs have selective in vitro antiproliferative activity for the endothelial cells over the tumor cell line assessed. The synthesis and SAR properties of these potential antitumor and antiangiogenic compounds will be discussed.

A novel series of compounds have been synthesized that retain the biological activities of $2ME_2$ and are expected to have reduced metabolism at position-17 and position-2. 17-Position alkylated analogs lack the hydroxyl moiety and cannot be metabolized to 2-methoxyestrone or conjugated at that position but retain antiproliferative activity in HUVEC and MDA-MB-231 cells.

Replacement of 2-methoxy group by other moieties such as 2-N-formamide or 2-formyl and 2-N.N-dimethylamino retained antiproliferative activity, but these groups cannot be de-methylated to yield the estrogenic 2-hydroxyl derivatives. These analogs have selective in vitro antiproliferative activity for endothelial cells over the tumor cell line assessed.

Also disclosed are compounds and methods for modifying the methyl ether of 2-methoxyestradiol so that it can not be a substrate for demethylase and the resulting compounds.

Also disclosed are compounds and methods for altering the chemical nature of positions 16 and 17 of 2-methoxyestradiol for preventing conversion to 2-methoxyestrone and/or the conjugation of 2-methoxyestradiol or metabolites with other molecules and its subsequent loss during excretion and the resulting compounds.

Other features and advantages of the invention will be apparent from the following description of preferred embodiments thereof.

DETAILED DESCRIPTION OF THE INVENTION

As described below, compounds that are useful in accordance with the invention include novel 2-methoxyestradiol derivatives that exhibit anti-mitotic, anti-angiogenic and anti-tumor properties. Specific compounds according to the invention are described below. Preferred compounds of the invention are 2-methoxyestradiol derivatives modified at the 2, 16, or 17 positions or combinations thereof. Those skilled in the art will appreciate that the invention extends to other compounds within the formulae given in the claims below, having the described characteristics. These characteristics can be determined for each test compound using the assays detailed below and elsewhere in the literature.

2-Methoxyestradiol is an endogenous metabolite of estradiol that has potent anti-proliferative activity and induces apoptosis in a wide variety of tumor and non-tumor cell lines. When administered orally, it exhibits anti-tumor and anti-proliferative activity with little or no toxicity. 2-Methoxyestradiol is metabolized to a less active metabolite, 2-methoxyestrone ($2ME_1$) as indicated by in vitro and in vivo results. Although not wishing to be bound by theory, it is believed that this metabolite is formed through the same enzymatic pathway as estrone is formed from estradiol. Although not wishing to be bound by theory, it is believed that the enzymes responsible for this reaction on estradiol are the 17β-hydroxysteroid dehydrogenases (17β-HSD) which utilize NADP+ as a co-factor (Han et al., *J. Biol. Chem.* 275:2, 1105–1111 (Jan. 12, 2000) and other references cited earlier). Each of the four members of this enzyme family, types 1, 2, 3, and 4, have distinct activity. It appears that 17β-HSD type 1 catalyzes the reductive reaction (estrone to estradiol), while 17β-HSD type 2 catalyzes the oxidation reaction (estradiol to estrone), and type 3 catalyzes 4-androstenedione to testosterone. It is also believed that an additional metabolic deactivation pathway results in conjugation of 2-methoxyestradiol or 2-methoxyestrone with molecules such as sulfate or glucuronic acid and subsequent loss via excretion. In this invention, positions 16 and/or 17 of 2-methoxyestradiol may be modified to prevent these metabolic pathways from occurring.

Since 2-methoxyestradiol is metabolized to a much less active metabolite, the present invention adds steric bulk and/or modification of chemical or electrostatic characteristics at positions 16 and 17 of 2-methoxyestradiol for retarding or preventing interaction of the family of 17β-hydroxysteroid dehydrogenases and co-factor $NADP^+$ on this substrate. Addition of steric bulk and/or modification of chemical or electrostatic characteristics at positions 16 and 17 of 2-methoxyestradiol may also retard or prevent conjugation, such as glucuronidation. It is believed that retardation or prevention of these two metabolic deactivation pathways prolongs the serum lifetime of 2-methoxyestradiol and other estradiol derivatives while retaining the desired anti-angiogenic and anti-tumor activity. Assays employed for measuring glucuronidation and conjugation employ substrate enzyme uridine 5'-diphospoglucuronic acid (UDGPA).

Aside from preventing the possible metabolism of $2ME_2$ to $2ME_1$, which may occur by making these steroids poor substrates for 17β-HSD (by either steric and/or electronic effects), it is not possible for analogs modified at the 2 position to undergo the demethylation known to occur with $2ME_2$ since there is no methyl ether group at that position. This is desirable since it has been demonstrated that 2-hydroxyestradiol (the product of demethylation of $2ME_2$) has estrogenic activity.

It is well known that orally-delivered steroids such as estradiol ($E_2$) and ethynyl-$E_2$ are extensively metabolized during passage through the gastrointestinal tract and by first-pass metabolism in the liver. Two major metabolic pathways that lead to rapid deactivation and excretion are well studied (Fotsis, T.; Zhang, Y.; Pepper, M. S.; Adlercrcutz, H.; Montesano, R.; Nawreth. P. P.; Schweigerer, L., The Endogenous Estrogen Metabolite 2-Methoxyestradiol Inhibits Angiogenesis and Supresses Tumor. *Nature*, 1994, 368, 237–239; Wang, Z.; Yang, D.; Mohanakrishnan, A. K.; Fanwick, P. E.; Nampoothiri, P.; Hamel, E.; Cushman, M. "Synthesis of B-Ring Homologated Estradiol Analogs that Modulate Tubulin Polymerization and Microtubule Stability." *J Med. Chem.,* 2000, 43, 2419–2429) e.g. oxidation at the D-ring's 17-hydroxy group of $E_2$ to form estrone and conjugation with sulfate and/or glucuronate at the hydroxyls of position-3 on the A-ring and position-17 on the D-ring.

Several studies have been conducted to determine SAR of $2ME_2$ analogs (D'Amato, R. J.; Lin, C. M.; Flynn, E.; Folkman, J.; Hamel, E. Inhibition of Angiogenesis and Breast Cancer in Mice by the Microtubule Inhibitors 2-Methoxyestradiol and Taxol", *Cancer Res.,* 1997, 57, 81–86; Cushman, M.; He, M. -H.; Katzenellenbogen, J. A.; Lin, C. M.; Hamel, E. "Synthesis, Antitubuln and Antimitotic Activity, and Cytotoxicity of Analogs of 2-Methoxyestradiol, an Endogenous Mammalian Metabolite of Estradiol that inhibits Tubulin Polymerization by Binding to the Colchicine Binding Site." *J. Med. Chem.* 1995, 38, 2041–2049) but none to reduce or stop its metabolic pathway. Compounds with no chain or with variable methylene chain lengths (1–4) were synthesized by replacing hydroxyl group at position-17 of D-ring of $2ME_2$ to block estrone formation or glucuronation. Similarly several analogs of 17-deoxyestrone with modification at position-2 were synthesized to block the both glucuronation and hydrolysis of the methoxy group to the hydroxyl. For these analogs data will be presented on the synthesis and preliminary in vitro screening in human umbilical vein endothelial cells (HUVEC) and breast cancer tumor MDA-MB-231 cells for antiproliferative activity, and in MCF-7 tumor cancer cells for estrogenic activity.

2-Methoxy-17-deoxyestrone, 17-ethyl-2-methoxyestrone and 17-methyl-2-methoxyestrone analogs showed equal or better antiproliferative activity than $2ME_2$ but have diminished the potential to change either into 2-methoxyestrone or to conjugate at position-17.

Increasing carbon chain length at-position-17 of 2-methoxyestrone decreases the antiproliferative activity.

Some position-2 modified 17-deoxyestrone analogs retained good antiproliferative activity in HUVEC cells only, suggesting that these analogs may be potent anti-angiogenics in vivo.

There was a slight decrease in antiproliferative activity in HUVEC cells as the 2-N-methylamino changed to 2-N,N-dimethylamino- 17-deoxyestrone.

2-Azido-estradiol that retained considerable antiproliferative activity was synthesized to identify $2ME_2$ binding proteins after photoactivation.

Also disclosed are compounds and methods for modifying the methyl ether of 2-methoxyestradiol so that it can not be a substrate for demethylase and the resulting compounds.

In another embodiment of the invention, derivatives are modified at combinations of the 2, 16 or 17 positions.

Anti-Proliferative Activity In Situ

Anti-proliferative activity is evaluated in situ by testing the ability of an improved estradiol derivative to inhibit the proliferation of new blood vessel cells (angiogenesis). A suitable assay is the chick embryo chorioallantoic membrane (CAM) assay described by Crum et al. *Science* 230:1375 (1985). See also, U.S. Pat. No. 5,001,116, hereby incorporated by reference, which describes the CAM assay. Briefly, fertilized chick embryos are removed from their shell on day 3 or 4, and a methylcellulose disc containing the drug is implanted on the chorioallantoic membrane. The embryos are examined 48 hours later and, if a clear avascular zone appears around the methylcellulose disc, the diameter of that zone is measured. Using this assay, a 100 μg disk of the estradiol derivative 2-methoxyestradiol was found to inhibit cell mitosis and the growth of new blood vessels after 48 hours. This result indicates that the anti-mitotic action of 2-methoxyestradiol can inhibit cell mitosis and angiogenesis.

Anti-Proliferative Activity In Vitro

The process by which $2ME_2$ affects cell growth remains unclear, however, a number of studies have implicated various mechanisms of action and cellular targets. $2ME_2$ induced changes in the levels and activities of various proteins involved in the progression of the cell cycle. These include cofactors of DNA replication and repair, e.g., proliferating cell nuclear antigen (PCNA) (Klauber, N., Parangi, S., Flynn, E., Hamel, E. and D'Amato, R. J. (1997), Inhibition of angiogenesis and breast cancer in mice by the microtubule inhibitors 2-methoxyestradiol and Taxol., Cancer Research 57, 81–86; Lottering, M -L., de Kock, M., Viljoen, T. C., Grobler, C. J. S. and Seegers, J. C. (1996) 17β-Estradiol metabolites affect some regulators of the MCF-7 cell cycle. Cancer Letters 110, 181–186); Cell division cycle kinases and regulators, e.g., $p34^{cdc2}$ and cyclin B (Lottering et al. (1996); Attalla, H., Mäkelä, T. P., Adlercreutz, H. and Andersson, L. C. (1996) 2-Methoxyestradiol arrests cells in mitosis without depolymerizing tubulin. Biochemical and Biophysical Research Communications 228, 467–473; Zoubine, M. N., Weston, A. P., Johnson, D. C., Campbell, D. R. and Baneijee, S. K. (1999) 2-Methoxyestradiol-induced growth suppression and lethality in estrogen- responsive MCF-7 cells may be mediated by down regulation of p34cdc2 and cyclin B1 expression. Int J Oncol 15, 639–646); transcription factor modulators, e.g., SAPK/JNK (Yue, T -L., Wang, X., Louden, C. S., Gupta, L. S., Pillarisetti, K., Gu, J -L., Hart, T. K., Lysko, P. G. and Feuerstein, G. Z. (1997) 2-Methoxyestradiol, an endogenous estrogen metabolite induces apoptosis in endothelial cells and inhibits angiogenesis: Possible role for stress-activated protein kinase signaling pathway and fas expression. Molecular Pharmacology 51, 951–962; Attalla, H., Westberg, J. A., Andersson, L. C., Aldercreutz, H. and Makela, T. P. (1998) 2-Methoxyestradiol-induced phosphorylation of bcl-2: uncoupling from JNK/SAPK activation. Biochem and Biophys Res Commun 247, 616–619); and regulators of cell arrest and apoptosis, e.g., tubulin (D'Amato, R. J., Lin, C. M., Flynn, E., Folkman, J. and Hamel, E. (1994) 2-Methoxyestradiol, and endogenous mammalian metabolite, inhibits tubulin polymerization by interacting at the colchicine site. Proc. Natl. Acad. Sci. USA 91, 3964–3968; Hamel, E., Lin, C. M., Flynn, E. and D'Amato, R. J. (1996) Interactions of 2-methoxyestradiol, and endogenous mammalian metabolite, with unploymerized tubulin and with tubulin polymers. Biochemistry 35, 1304–1310), $p21^{WAF1/CIP1}$ (Mukhopadhyay, T. and Roth, J. A. (1997) Induction of apoptosis in human lung cancer cells after wild-type p53 activation by methoxyestradiol. Oncogene 14, 379–384), bcl-2 and FAS (Yue et al. (1997); Attalla et al. (1998)), and p53 (Kataoka, M., Schumacher, G., Cristiano, R. J., Atkinson, E. N., Roth, J. A. and Mukhopadhyay, T. (1998) An agent that increases tumor suppressor transgene product coupled with systemic transgene delivery inhibits growth of metastatic lung cancer in vivo. Cancer Res 58, 4761–4765; Mukhopadhyay et al. (1997); Seegers, J. C., Lottering, M -L., Grobler C. J. S., van Papendorp, D. H., Habbersett, R. C., Shou, Y. and Lehnert B. E. (1997) The mammalian metabolite, 2-methoxyestradiol, affects p53 levels and apoptosis induction in transformed cells but not in normal cells. J. Steroid Biochem. Molec. Biol. 62, 253–267). The effects on the level of cAMP, calmodulin activity and protein phosphorylation may also be related to each other. More recently, $2ME_2$ was shown to upregulate Death Receptor 5 and caspase 8 in human endothelial and tumor cell lines (LaVallee, T. M., Zhan, X. H., Herbstritt, C. J., Williams, M. S., Hembrough, W. A., Green, S. J.,and Pribluda, V. S. 2001. 2-Methoxyestradiol induces apoptosis throughactivation of the extrinsic pathway. (Manuscript in preparation)). Additionally, 2ME2 has been shown to interact with superoxide dismutase (SOD) 1 and SOD 2 and to inhibit their enzymatic activities (Huang, P., Feng, L., Oldham, E. A., Keating, M. J., and Plunkett, W. 2000. Superoxide dismutase as a target for the selective killing of cancer cells, Nature. 407:390–5.). All cellular targets described above are not necessarily mutually exclusive to the inhibitory effects of $2ME_2$ in actively dividing cells.

The high affinity binding to SHBG has been mechanistically associated to its efficacy in a canine model of prostate cancer, in which signaling by estradiol and 5α-androstan-3 α, 17β-diol were inhibited by $2ME_2$ (Ding, V. D., Moller, D. E., Feeney, W. P., Didolkar, V., Nakhla, A. M., Rhodes, L., Rosner, W. and Smith, R. G. (1998) Sex hormone-binding globulin mediates prostate androgen receptor action via a novel signaling pathway. Endocrinology 139, 213–218).

The more relevant mechanisms described above have been extensively discussed in Victor S. Pribluda, Theresa M. LaVallee and Shawn J. Green, 2-*Methoxyestradiol: A novel endogenous chemotherapeutic and antiangiogenic* in The New Angiotherapy, Tai-Ping Fan and Robert Auerbach eds., Human Press Publisher.

Assays relevant to the mechanisms of action and cell proliferation are well-known in the art. For example,. antimitotic activity mediated by effects on tubulin polymerization activity can be evaluated by testing the ability of an estradiol derivative to inhibit tubulin polymerization and microtubule assembly in vitro. Microtubule assembly is followed in a Gilford recording spectrophotometer (model 250 or 2400S) equipped with electronic temperature controllers. A reaction mixture typically contains 1.0 M monosodium glutamate (pH 6.6), 1.0 mg/ml (10 µM) tubulin, 1.0 mM $MgCl_2$, 4% (v/v) dimethylsulfoxide and 20–75 µM of a composition to be tested. The reaction mixtures are incubated for 15 min. at 37° C. and then chilled on ice. After addition of 10 µl 2.5 mM GTP, the reaction mixture is transferred to a cuvette at 0° C., and a baseline established. At time zero, the temperature controller of the spectrophotometer is set at 37° C. Microtubule assembly is evaluated by increased turbity at 350 nm. Alternatively; inhibition of microtubule assembly can be followed by transmission electron microscopy as described in Example 2 of U.S. Pat. Nos. 5,504,074, 5,661,143, and 5,892,069.

Other such assays include counting of cells in tissue culture plates or assessment of cell number through metabolic assays or incorporation into DNA of labeled (radiochemically, for example $^3$H-thymidine, or fluorescently labeled) or immuno-reactive (BrdU) nucleotides. In addition, antiangiogenic activity may be evaluated through endothelial cell migration, endothelial cell tubule formation, or vessel outgrowth in ex-vivo models such as rat aortic rings.

Indications

The invention can be used to treat any disease characterized by abnormal cell mitosis. Such diseases include, but are not limited to: abnormal stimulation of endothelial cells (e.g., atherosclerosis), solid tumors and tumor metastasis, benign tumors, for example, hemangiomas, acoustic neuromas, neurofribomas, trachomas, and pyogenic granulomas, vascular malfunctions, abnormal wound healing, inflammatory and immune disorders, Bechet's disease, gout or gouty arthritis, abnormal angiogenesis accompanying: rheumatoid arthritis, skin diseases, such as psoriasis, diabetic retinopathy, and other ocular angiogenic diseases such as retinopathy of prematurity (retrolental fibroplasic), macular degeneration, corneal graft rejection, neuroscular glaucoma, liver diseases and Oster Webber syndrome (Osler-Weber Rendu disease).

Diseases associated with corneal neovascularization that can be treated according to the present invention include but are not limited to, diabetic retinopathy, retinopathy of prematurity, corneal graft rejection, neovascular glaucoma and retrolental ibroplasias, epidemic keratoconjunctivitis, Vitamin A deficiency, contact lens overwear, atopic keratitis, superior limbic keratitis, pterygium keratitis sicca, sjogrens, acne, rosacea, phylectenulosis, syphilis, *Mycobacteria* infections, lipid degeneration, chemical bums, bacterial ulcers, fungal ulcers, *Herpes simplex* infections, *Herpes zoster* infections, protozoan infections, Kaposi's sarcoma, Mooren's ulcer, Terrien's marginal degeneration, mariginal keratolysis, trauma, rheumatoid arthritis, systemic lupus, polyarteritis, Wegener's sarcoidosis, scleritis, Steven-Johnson disease, pemphigoid radial keratotomy, and corneal graph rejection.

Diseases associated with retinal/choroidal neovascularization that can be treated according to the present invention include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales' disease, Behcet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy, whether or not associated with diabetes.

Another disease which can be treated according to the present invention is rheumatoid arthritis. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Another disease that can be treated according to the present invention are hemangiomas, Osler-Weber-Rendu disease, or hereditary hemorrhagic telangiectasia, solid or blood borne tumors and acquired immune deficiency syndrome.

In addition, the invention can be used to treat a variety of post-menopausal symptoms, osteoporosis, cardiovascular disease, Alzheimer's disease, to reduce the incidence of strokes, and as an alternative to prior estrogen replacement therapies. The compounds of the present invention can work by estrogenic and non-estrogenic biochemical pathways.

Prodrug

The present invention also relates to conjugated prodrugs and uses thereof. More particularly, the invention relates to conjugates of estradiol compounds such as 2-methoxyestradiol and functionally active analogues and derivatives thereof, and the use of such conjugates in the prophylaxis or treatment of conditions associated with enhanced angiogenesis or accelerated cell division, such as cancer, and inflammatory conditions such as asthma and rheumatoid arthritis and hyperproliferative skin disorders including psoriasis. The invention also relates to compositions including the prodrugs of the present invention and methods of synthesizing the prodrugs.

In one aspect, the present invention provides a conjugated prodrug of an estradiol compound, preferably of 2-methoxyestradiol or a functionally active analogue or derivative thereof, conjugated to a biological activity modifying agent.

By "functionally active" is meant that the analogue or derivative of 2-methoxyestradiol has one or more of the biological activities of 2-methoxyestradiol. The biological activities of 2-methoxyestradiol include, but are not limited to: inhibition of endothelial cell proliferation; inhibition of smooth muscle cell proliferation; inhibition of tumour cell proliferation inhibition of microtubule function; inhibition of leukocyte activation. Examples of such functionally active analogues or derivatives include 2-ethoxyestradiol, 2-hydroxyestradiol and other analogues modified at the 2 position, 2-methoxyestradiol-3-methylether, 4-methoxyestradiol, and other analogues in which the B ring is expanded to a 7-numbered ring. See also WO95/04535 and WO 01/27132 the entire disclosures of which are incorporated herein by reference.

Alternatively, the conjugated prodrug according to the present invention includes 2-methoxyestradiol or a functionally active analogue or derivative thereof, conjugated to a peptide moiety.

The incorporation of an estradiol compound such as 2-methoxyestradiol into a disease-dependently activated pro-drug enables significant improvement of potency and selectivity of this anti-cancer and anti-inflammatory agent.

In addition to the compounds of the present invention, the pharmaceutical composition of this invention may also contain, or be co-administered (simultaneously or sequentially) with, one or more pharmacological agents of value in treating one or more disease conditions referred to hereinabove.

In addition, the prodrug may be incorporated into biodegradable polymers allowing for sustained release, the polymers being implanted in the vicinity of where delivery is desired, for example, at the site of a tumour. The biodegradable polymers and their use are described in detail in Brem et al., J. Neurosurg 74:441–446 (1991).

A person skilled in the art will be able by reference to standard texts, such as Remington's Pharmaceutical Sciences 17th edition, to determine how the formulations are to be made and how these may be administered.

In a further aspect of the present invention there is provided use of a conjugated prodrug according to the present invention for the preparation of a medicament for the prophylaxis or treatment of conditions associated with angiogenesis or accelerated cell division or inflammation.

In a further aspect of the present invention there is provided a pharmaceutical composition comprising a conjugated prodrug according to the present invention, together with a pharmaceutically acceptable carrier, diluent or excipient.

The pharmaceutical composition may be used for the prophylaxis or treatment of conditions associated with angiogenesis or accelerated cell division or inflammation.

In a still further aspect of the present invention there is provided a method of prophylaxis or treatment of a condition associated with angiogenesis or accelerated or increased amounts of cell division hypertrophic growth or inflammation, said method including administering to a patient in need of such prophylaxis or treatment an effective amount of a conjugated prodrug according to the present invention, as described above.

It should be understood that prophylaxis or treatment of said condition includes amelioration of said condition.

By "an effective amount" is meant a therapeutically or prophylactically effective amount. Such amounts can be readily determined by an appropriately skilled person, taking into account the condition to be treated, the route of administration and other relevant factors. Such a person will readily be able to determine a suitable dose, mode and frequency of administration.

Pharmaceutically acceptable salts of the compound of the formula may be prepared in any conventional manner for example from the free base and acid. In vivo hydrolysable esters, amides and carbamates may be prepared in any conventional manner.

Improved Estradiol Derivative Synthesis

Known compounds that are used in accordance with the invention and precursors to novel compounds according to the invention can be purchased, e.g., from Sigma Chemical Co., St. Louis, Steraloids and Research Plus. Other compounds according to the invention can be synthesized according to known methods from publicly available precursors.

The chemical synthesis of estradiol has been described (Eder, V. et al., Ber 109, 2948 (1976); Oppolzer, D. A. and Roberts, D A. Helv. Chim. Acta. 63, 1703, (1980)). The synthetic pathways used to prepare some of the derivatives of the present invention are based on modified published literature procedures for estradiol derivatives and dimethylhydrazone (Trembley et al., Bioorganic & Med. Chem. 1995 3, 505–523; Fevig et al., J. Org. Chem., 1987 52, 247–251; Gonzalez et al., Steroids 1982, 40, 171–187; Trembley et al., Synthetic Communications 1995, 25, 2483–2495; Newkome et al., J. Org. Chem. 1966, 31, 677–681; Corey et al Tetrahedron Lett 1976, 3–6; Corey et al., Tetrahedron Lett, 1976, 3667–3668) and German Patent No. 2757157 (1977). See for example, Table 3, compounds 2, 3, 4, 6. The modifications are provided in Example 15 below. Initial screening of epimeric 16-ethyl-2-methoxyestradiol and analogues showed that it is about equipotent to 2-methoxyestradiol in inhibition of HUVEC cell proliferation in vitro.

Administration

The compositions described above can be provided as physiologically acceptable formulations using known techniques, and these formulations can be administered by standard routes. In general, the combinations may be administered by the topical, oral, rectal or parenteral (e.g., intravenous, subcutaneous or intramuscular) route. In addition, the combinations may be incorporated into biodegradable polymers allowing for sustained release, the polymers being implanted in the vicinity of where delivery is desired, for example, at the site of a tumor or within or near the eye. The biodegradable polymers and their use are described in detail in Brem et al., J. Neurosurg. 74:441–446 (1991). The dosage of the composition will depend on the condition being treated, the particular derivative used, and other clinical factors such as weight and condition of the patient and the route of administration of the compound. However, for oral administration to humans, a dosage of 0.01 to 100 mg/kg/day, preferably 0.01–20 mg/kg/day, is generally sufficient.

The formulations include those suitable for oral, rectal, nasal, topical (including buccal and sublingual), vaginal or parenteral (including subcutaneous, intramuscular, intravenous, intradermal, intraocular, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tablets may be made by molding, in a suitable machine, a mixture of the powdered compound moistened with an inert liquid diluent. The tablets may optionally be coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is taken, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such as carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tables of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of the present invention may include other agents conventional in the art having regard to the type of formulation in question, for example, those suitable for oral administration may include flavoring agents.

2-Methoxyestradiol is an endogenous metabolite of estradiol ($E_2$) that has potent anti-proliferative activity and induces apoptosis in a wide variety of tumor and non-tumor cell lines. When administered orally, it exhibits anti-tumor and anti-proliferative activity with little or no toxicity. In vitro data suggests that 2-methoxyestradiol does not engage the estrogen receptor for its anti-proliferative activity. However, the presence of demethylases in vivo may metabolize this compound to 2-hydroxyestradiol, which has been shown to be estrogenic by several approaches. The present invention improves the bioavailability of estradiol or 2-methoxyestradiol and reduces the formation of estrogenic 2-methoxyestradiol metabolites. Although not wishing to be bound by theory, it is believed that the present invention modifies estradiol analogs in such a way to prevent or hinder demethylation, oxidation, and conjugation with another molecule during metabolism.

The present invention includes compositions and methods for treating mammalian disease characterized by pathogenic angiogenesis by administering derivates of 2-methoxyestradiol. The derivatives may be modified at the 2, 16, or 17 positions or combinations thereof, where it is chemically possible to someone skilled in the art. Combinations which are physically impossible are not contemplated by this invention, such as a carbon atom containing 5 bonds. The 2, 6, 16, and 17 positions may be modified with the following groups:

a) alkyls (both straight and branched up to ten carbons, having either the alpha or beta stereochemistry, and may be saturated or unsaturated, substituted or unsubstituted);

b) alkenyls, including, but not limited to, olefin regio- and/or stereoisomers (E- and Z-configurations of the olefin, and the hydrocarbon chain can be straight or branched, up to ten carbons, and may be saturated or unsaturated, substituted or unsubstituted), with the C=C at any position;

c) alkynyls with either straight or branched alkyl chains, up to ten carbons; and may be saturated or unsaturated, substituted or unsubstituted, with the C≡C at any position;

d) wherein aromatic or hetero groups can be incorporated into all of the above alkyl, alkenyl and alkynyl chains either singly or in combinations thereof, and wherein the aromatic groups include but are not limited to, phenyl, phenol, aniline, anisole, toluene (ortho, meta or para derivatives), zylenes, and the hetero groups include, but are not limited to, ether, amine, carbonyl containing functional groups, alcohols, phosphates, trifluoro and thiol groups, acids, esters, sulfates, sulfonates, sulfones, sulfamates and amides;

e) mono, dialkyl or trialkyl amine substitutions with either the alpha or beta stereochemistry (alkyl can be either straight or branched, up to ten carbons);

f) —CF$_2$, —CHF$_2$, —CF$_3$ and longer carbon chains up to 10 carbons, such as trifluoroethanes, pentafluoroethanes, fluorinated alkyl or alkene chains up to ten carbons, with the position on the chain varying with what is chemically possible to one of skill in the art;

g) hetero groups other than those of d) and e) that are not substituted, mono-substituted or multiply substituted;

h) aromatic groups other than those of d) that are not substituted, mono-substituted or multiply substituted;

i) both an alkyl group and a hetero or aromatic group incorporated at a single position simultaneously; and j) geminal alkyl, hetero, or aromatic groups incorporated simultaneously (geminal is defined as two substituents at the same C).

A hetero groups is defined herein as any group which contains at least one atom that is not C or H. A hetero group may contain other substituents, such as aromatic rings and other functional groups. The hetero group may be directly attached to the ring or on a substituent of a group. Especially considered are O, N, S, and P.

100% pure isomers are contemplated by this invention, however a stereochemical isomer labeled as α or β may be a mixture of both in any ratio, where it is chemically possible by one skilled in the art.

Particularly considered at positions 2, 16 and 17 are the modifications of acid, amide, amine, linear and branched chain alkanes, alkenes and alkynes with heteroatom substitutions, including, but not limited to, carbonyl, —CO—, —S—, —NH—, and/or —O— instead of CH$_2$ and also optionally substituted with hydroxyl, amino, sulphydryl, azide, halides, nitro, azides, nitrile, sulfamate, carbamate, phosphate, azides and azos, ester, ether, halide, formamide, nitro, nitrile, sulfide, sulfoxide, sulfate, sulfamate, phosphate, and phosphonate instead of H; single or multiple homocyclic or heterocyclic rings of 3, 4, 5, 6, 7 or 8 members, either saturated or unsaturated, attached directly to the 2, 16 or 17 position or linked via linear or branched chain alkanes, alkenes or alkynes with heteroatom substitutions, including, but not limited to, —S—, —NH—, and/or —O—, the ring hydrogens and linker hydrogens optionally being further substituted with groups, including, but not limited to those disclosed above, including, but not limited to, hydroxyl, amino, sulfhydryl and which are chemically possible for one skilled in the art.

Furthermore, at any position on the steroid rings, the following groups can be incorporated where it is chemically possible by one skilled in the art:

i) R is hydrogen;

ii) R is alkyl chains, straight and branched with stereoisomers up to 10C;

iii) R is alkene or alkyne derivatives of above alkyl chain with the olefin or alkyne moiety at any position and any configuration on the chain. Also included are multiply unsaturated alkyl chains of any configuration up to 10. The alkyl chain could be substituted with a phenyl substitutent and substituted phenyl substiutents (examples include, but are not limited to, aniline, anisole, toluene, phenol);

iv) alkyl, alkene or alkyne chains up to 10C (straight or branched) independently containing either one or multiple ester (R is defined in paragraphs ii and iii above), carboxylic acids, ketone (R is defined in paragraphs ii and iii above), aldehyde, alcohols, amine (primary, secondary tertiary and quaternary, with independent R as defined in paragraphs i, ii and iii above) nitrile, azide, urea (with R defined in paragraphs i, ii and iii above), oxime (and alkyl oxime) and halides (F, Cl, Br, I) and pharmaceutically acceptable salts of the above;

v) amines (primary, secondary, tertiary and quaternary) amines attached directly to the steroid, with R groups independently as defined in paragraphs i, ii and iii above, and pharmaceutically acceptable salts;

vi) ethers and polyethers attached directly to the steroid, where C=1 to 10;

vii) polyamines and polyols attached directly to the steroid where C=1–10;

viii) ring structures as indicated below, also including epoxides, aziridines and episulfide:

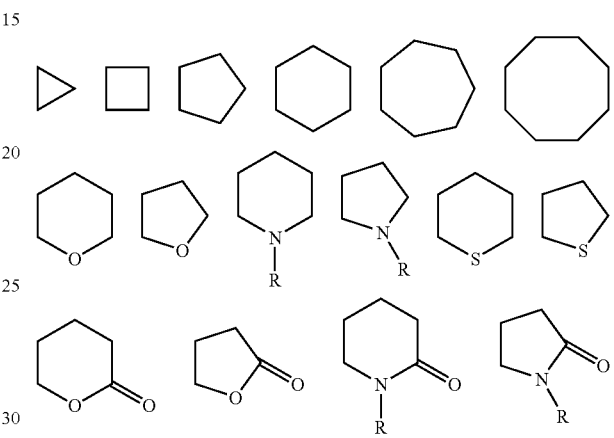

the ring structures above may have R groups (defined in parts i–vii and ix–xv) substituted at any position on the ring structure, have varying degrees of unsaturation, and be attached to any position on the steroid directly (for example, at a spiro ring junction or at a heteroatom) or through an alkyl or hetero or alkyl hetero chain, and where chemically possible to one skilled in the art;

ix) sulfate, sulfoxide, sulfamate, sulfone, sulfide, disulfide;

x) phosphate, phosphonate;

xi) nitro;

xii) amides substituted with any R group defined in paragraphs i, ii and iii above, attached to the steroid through either the carbonyl carbon or amide nitrogen, or linked to the steroid by an R group as defined in paragraphs ii and iii above;

xiii) any halogen containing alkyl, alkene and alkyne moiety (for example, CX, CX$_2$, CX$_3$ where X=F, Cl, Br, I);

xiv) —CO(CH$_2$)$_n$ OR n=0 to 10 the alkyl chain can also contain alkene or alkyne functionalities as defined in i, ii and iii above; and xv) amino acids or peptides, naturally and unnaturally occurring, up to 20 amino acids in length.

In general, all compounds were prepared using chemistry developed for analogous estradiol analogs. The modifications to these procedures generally involved protection of the 3-hydroxy group of 2-methoxyestradiol with a benzyl ether and cleavage of this ether at the appropriate point in the synthetic path as depicted in schemes 1–15.

The compounds listed in Table 1 were prepared by a variety of synthetic methodologies from either 3-protected 2-methoxyestradiol or estrone or 2-methoxyestrone. In Table 1, entry 2 was prepared using the Mitsunobu inversion as in Scheme 2 (Clive et al *J. Org. Chem,* 1991, 56, 3801). Entries 4 and 11 were prepared by reductive amination as in Scheme 1, route A and Scheme 3. Entry 3 was prepared as in Scheme 4 (Shapiro et al *J. Org. Chem.,* 1964, 86, 2825) although other methods such as the Barton deoxygenation (Robins et al *J. Am. Chem. Soc.* 1983, 105, 4059), other standard methods such as the Clemmenson reduction or Shapiro reaction can be utilized as well. Compounds 5 and 14 were synthesized via Schemes 1, route B and 4. Entries 7, 8, 9, 10, 12, 13, butyl and butene were prepared via Scheme 1, route B and 5 (Schow et al *J. Org Chem.* 1979, 22, 3760).

As expected with unstabilized ylides under salt free conditions, the 17(20) Z olefin was the major isomer. This was confirmed by NOESY NMR spectrometry. A weak NOE was observed between vinyl $H_{20}$ and $H_{18}$ methyl, whereas a significant NOE was observed between $H_{18}$ methyl and allylic $H_{21}$; a strong NOE was also noted between vinyl $H_{20}$ and allylic $H_{21}$. This data indicates a Z-alkene configuration as the major isomer, and the E-olefin as the minor (relative ratios are indicated in the example section).

Other approaches to the olefin products can utilize titanium based reagents (McMurray *Chem. Rev.* 1989, 89, 1513 or Pine et al *Synthesis,* 1991, 165) or the Peterson olefination reaction (Peterson et al *J. Org. Chem.* 1968, 33, 780). Entry 6 was prepared quantitatively from 2-methoxyestradiol as in Dean et al *Steroids,* 1971, 18, 130.

For Table 2, compounds 2, 3 and 4 were prepared via Scheme 6 (Pert et al *Aust. J. Chem.* 1989, 42, 405; Lovely et al *Tetrahedron Lett.,* 1994, 35, 8735 and Nambara et al *Chem. Pharm Bull* 1970, 18, 474 (alternate method)). Compounds 7, 8, 14 and 17 were synthesized via Scheme 7 (Cushman et al *J. Med. Chem* 1995, 38, 2041; alternate reductions of nitro compounds—Stubenrauch et al *Steroids* 1976, 28, 733; *J. Org. Chem.* 1988, 53 1775). Scheme 8 was used to prepare entries 10, 11, 12, 13 and 19. Compound 15 was prepared via Scheme 9 and compounds 16 and 18 were prepared as in Cushman et al *J. Med. Chem.* 1995, 38, 2041.

The starting material for all analogs in Table 3 was 3-benzylether-2-methoxy-17-estrone which was prepared as in Scheme 1A. For Table 3, entries 2 and 13 were prepared via Schemes 10 and 11 and gave the 16-alpha stereoisomer exclusively. (German patent 2757157 (1977); Newkome et al *J. Org. Chem.,* 1966, 31, 677; Corey et al *Tetrahedron Lett.* 1976, 3; Corey et al *Tetrahedron Lett.* 1976, 3667). Entries 3, 5, 6, 8 and 9 were prepared via Schemes 12 and 11 (Tremblay et al *Bioorg. & Medicinal Chemistry* 1995, 3, 505) and gave the 16-beta stereoisomer as the major product. Compounds 5 and 6 were separated via column chromatography (Tremblay et al *Synthetic Comm.* 1995, 25, 2483.) Entries 4, 7, 10 and 11 used Schemes 13 and 11 (Tremblay et al *Bioorg. & Medicinal Chemistry* 1995, 3, 505) and gave the 16-alpha stereoisomer as the predominant product in most cases. Scheme 14 was used to prepare entry 12 (Gonzalez et al *Steroids* 1982, 40, 171).

Scheme 1
Preparation of 2-methoxyestrone derivatives

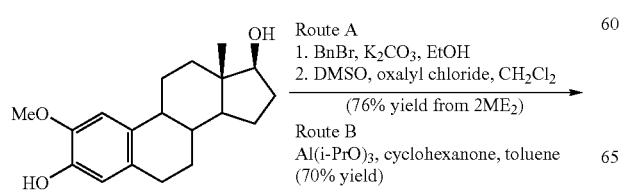

Route A
1. BnBr, $K_2CO_3$, EtOH
2. DMSO, oxalyl chloride, $CH_2Cl_2$
(76% yield from $2ME_2$)

Route B
Al(i-PrO)$_3$, cyclohexanone, toluene
(70% yield)

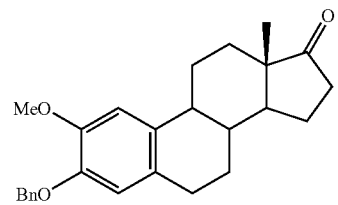

R = Bn, Route A
R = H, Route B

Scheme 2
Syntheisi of 17α-$2ME_2$

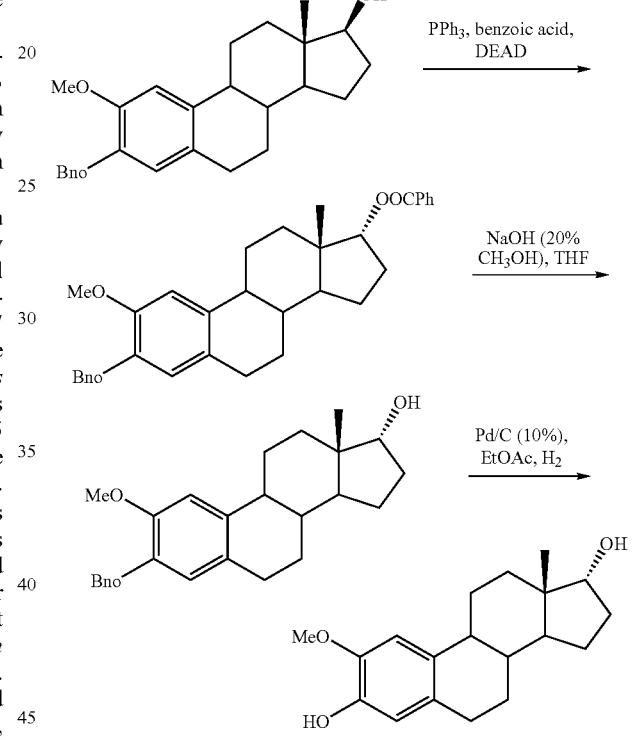

Ref: Clive et al; J. Org. Chem, 1991, 56, 3801.

Scheme 3
Preparation of 17-amine subtitutied-2-methoxy-1,3,5(10)triene-3-ol

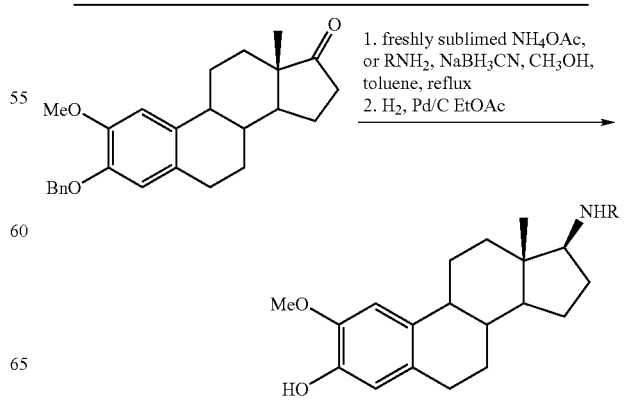

1. freshly sublimed $NH_4OAc$, or $RNH_2$, $NaBH_3CN$, $CH_3OH$, toluene, reflux
2. $H_2$, Pd/C EtOAc

Scheme 4
Synthesis of 2-Methoxyestrone Analogs
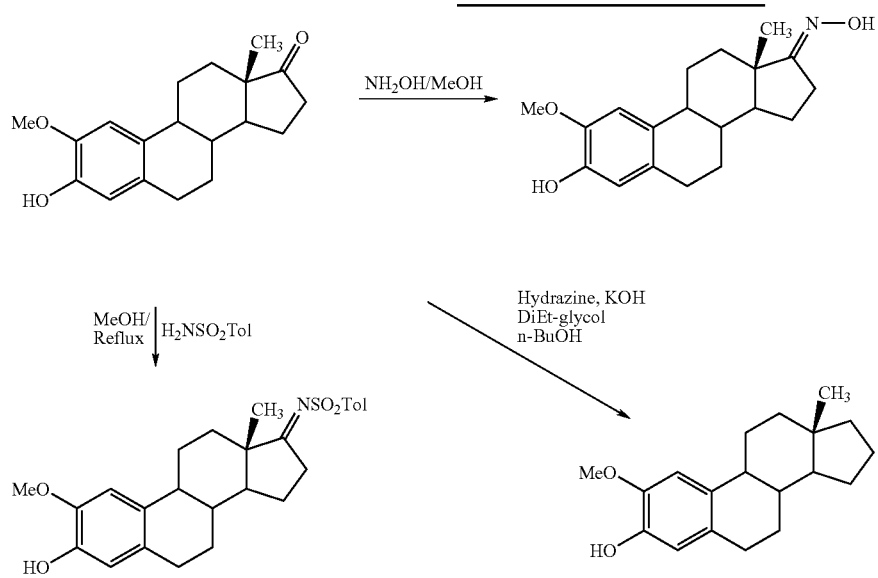
Scheme 5
Preparation of 17-olefin and 17-alkyl 2ME$_1$ Derivatives
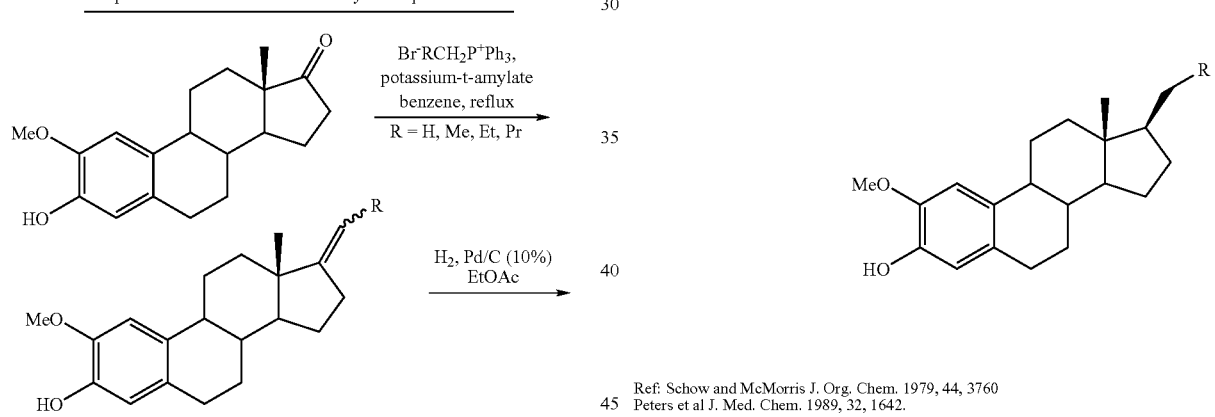
Ref: Schow and McMorris J. Org. Chem. 1979, 44, 3760
Peters et al J. Med. Chem. 1989, 32, 1642.
Scheme 6
Synthesis of 2-formyl, 2-methylenehydroxy and 2acetyl-E$_2$
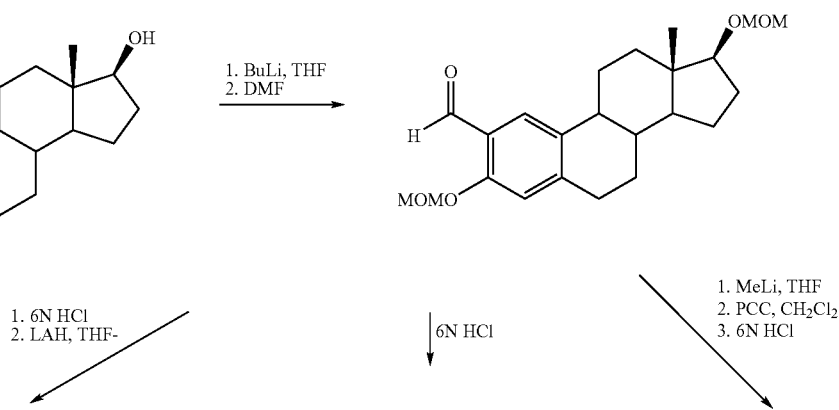

-continued
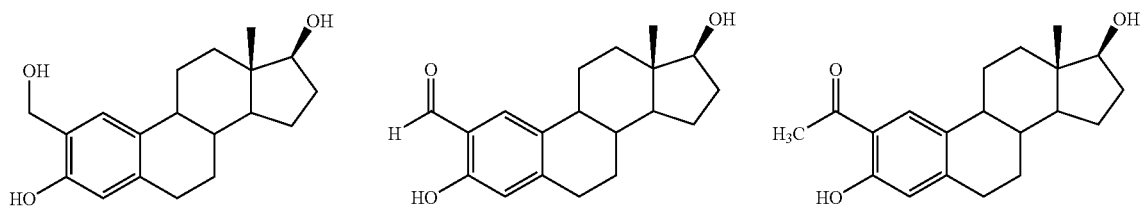
Ref: Pert et al Aust. J. Chem. 1989, 42, 405
Lovely et al Tetrahedron Lett., 1994, 35, 8735.
Alternate route to 2-acetyl-estradiol Nanbara et al Chem. Pharm. Bull. 1970, 18, 474.
Scheme 7
Preparation of 2-nitro, 2-amino and 2-azido $E_2$
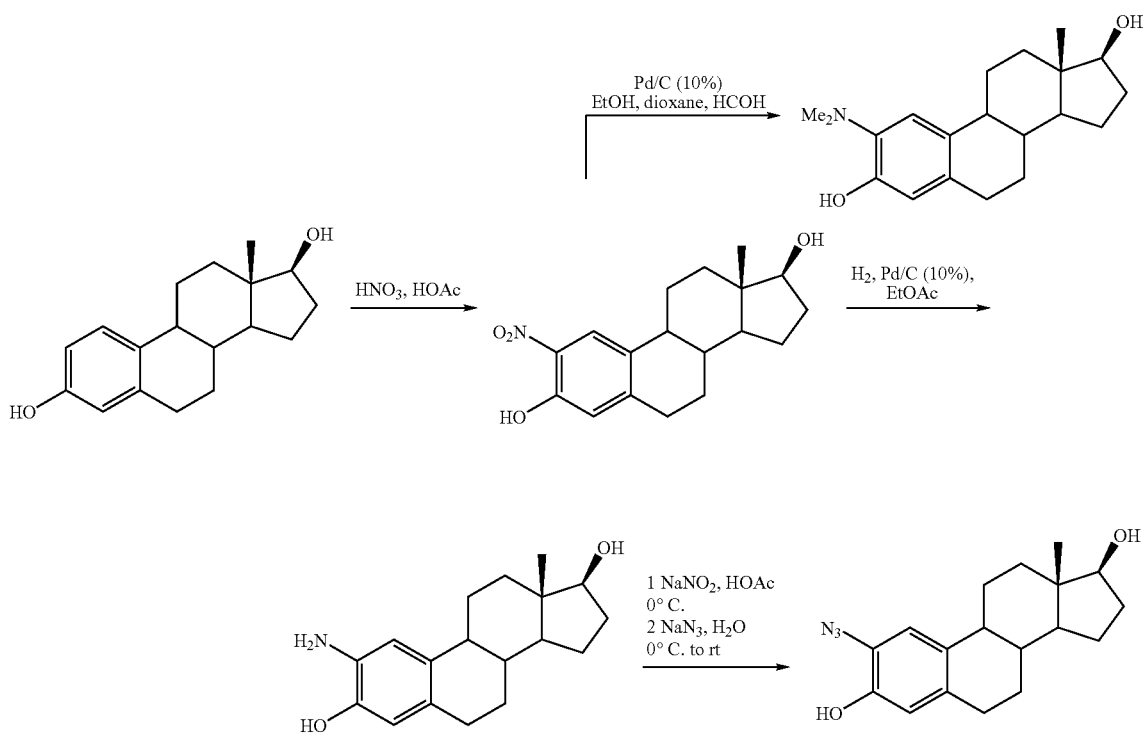
Alternative reduction procedure: Stubenrauch et al Steriods, 1976, 28, 733.
J Org. Chem. 1988, 53, 1775.
Scheme-8
Synthesis of 2-Alkylamino-17-Deoxyestrone Analogs
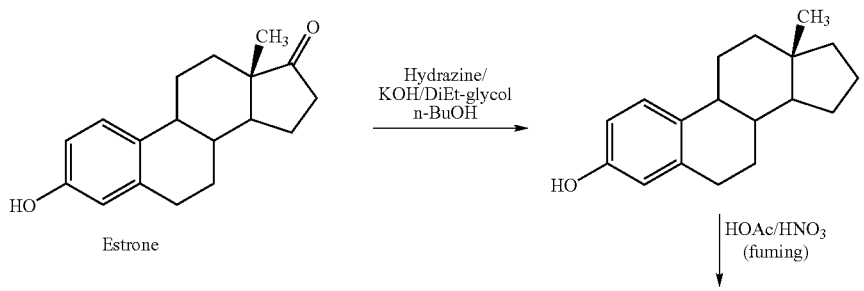

-continued
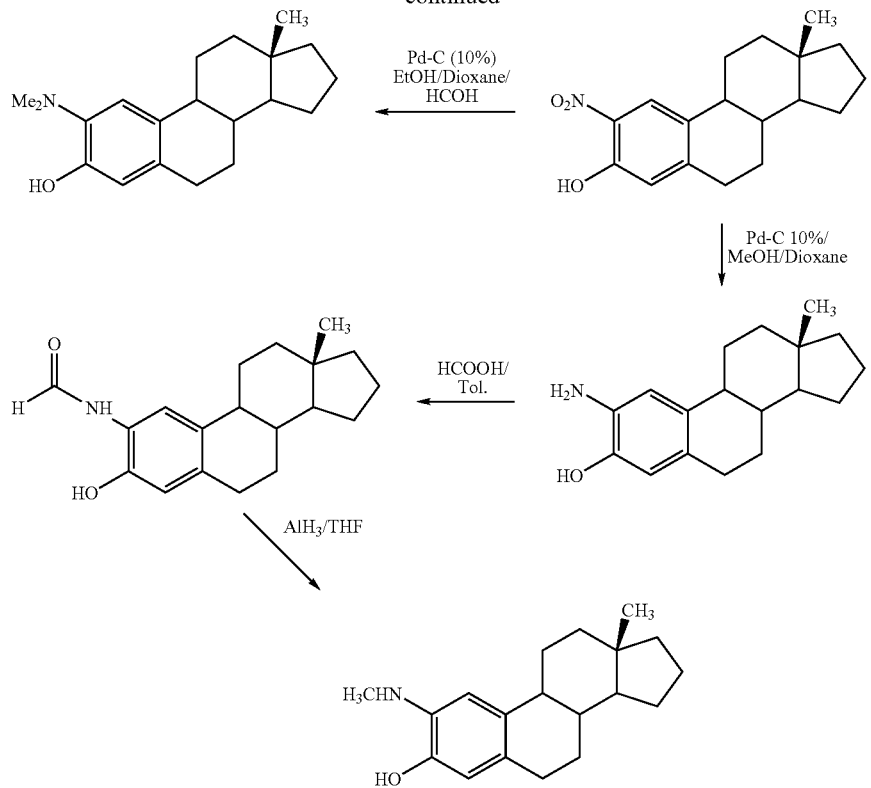
Scheme 9
Synthesis of 2-(N,N-dimethylamino)-17(20)-methyleneestra-1,3,5(10)triene-3-ol
Scheme 10
Synthesis of 16α-2ME₁ Analogs
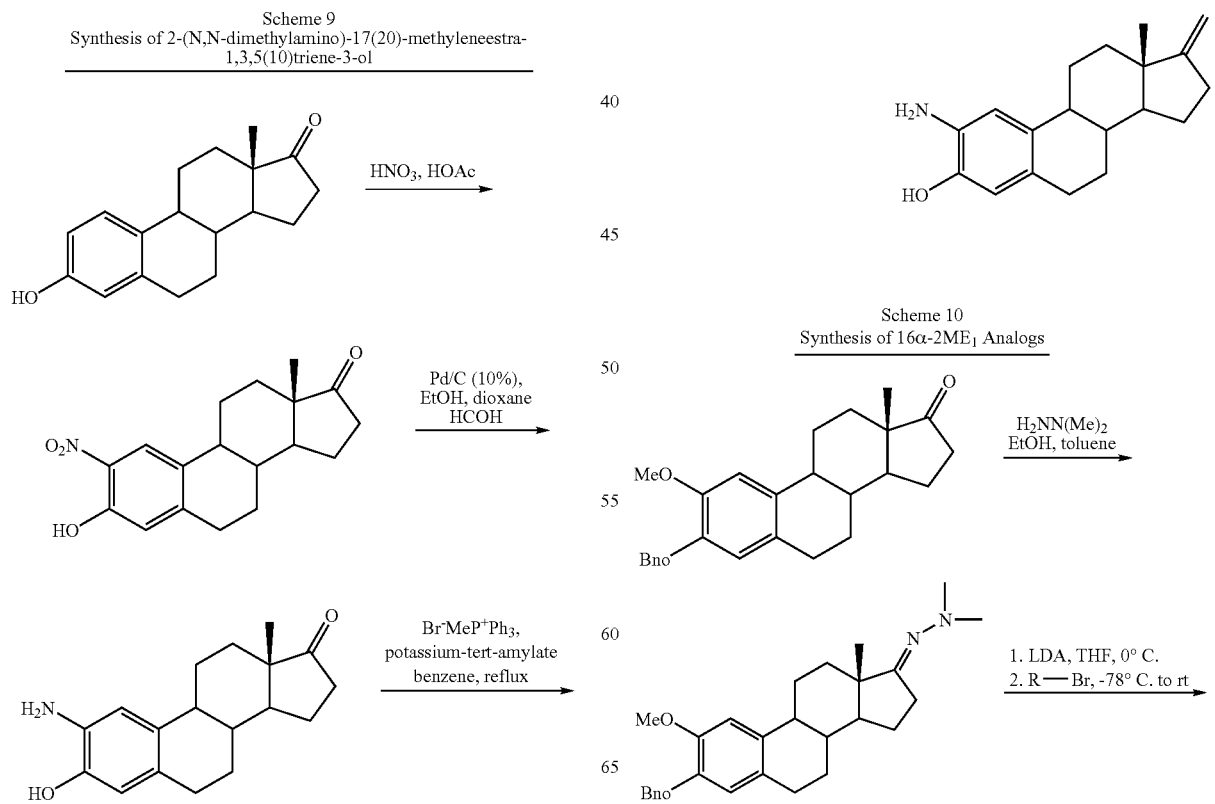

Scheme 11
Reduction and Deprotection of 16-alkyl-2-Methoxyestrone
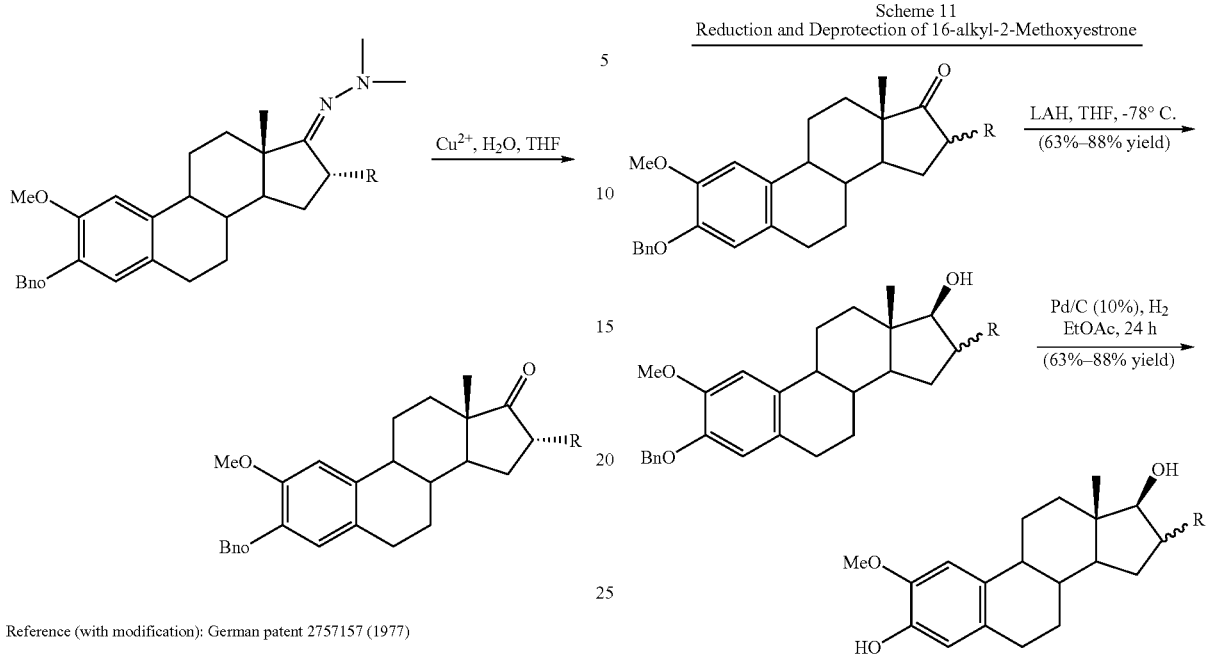
Reference (with modification): German patent 2757157 (1977)
Scheme 12
Synthesis of 16β-Alkyl-2-Methoxyestrone Analogs
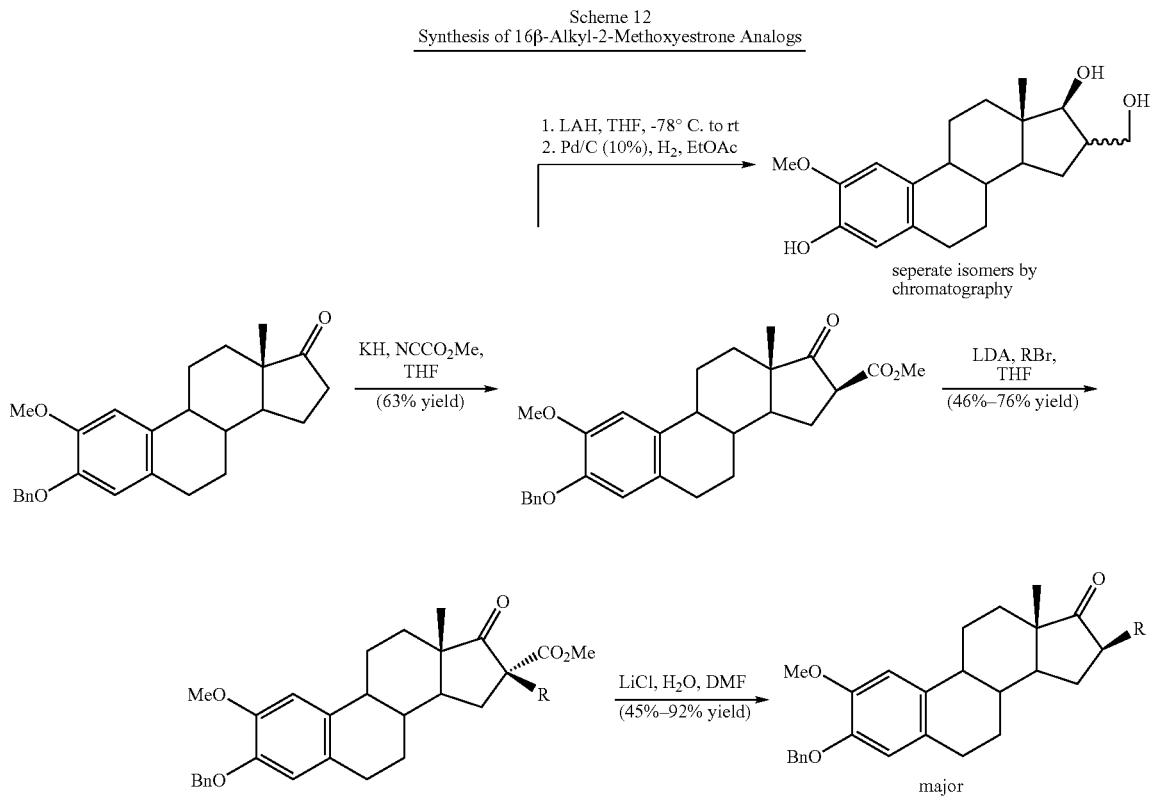
Reference (with modification): Trembly et al Bioorg. & Med. Chem. 1995, 3, 505.
Trembly et al Synthetic Comm. 1995, 25, 2483.

Scheme 13
Preparation of 16α-Alkyl-2-Methoxyestrone

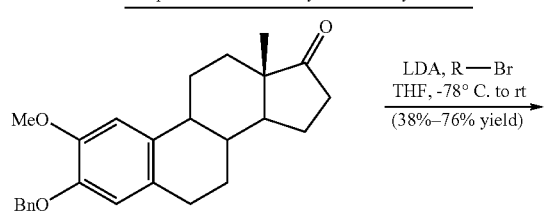

Reference (with modification): Trembly et al Bioorg. & Med. Chem 1995, 3, 505.

Scheme 14
Preparation of 2-methoxy-16β-(N,N-dimethylaminomethyl)estra1,3,5(10)-triene-3,17β-diol

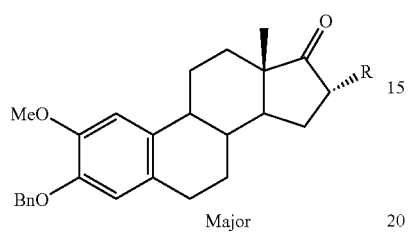

Ref: Gonzalez et al Steriods 1982, 40, 171.

Scheme 15
Preparation of 2-methoxy-estra-1,3,5(10)9(11)tetraen-3-ol

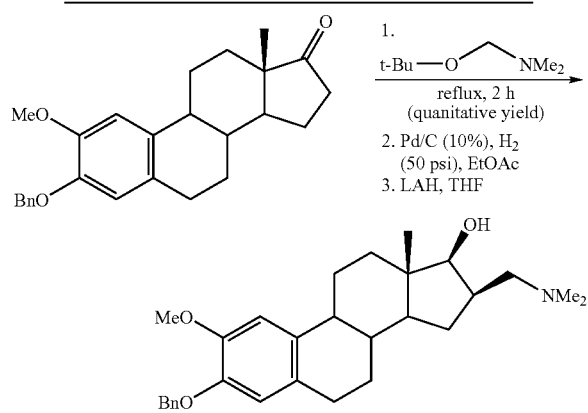

-continued

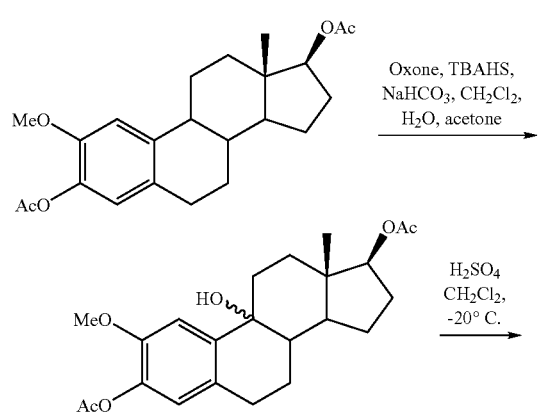

Ref: Modification of Schwarz et al Steroids, 1999, 64, 460.

TABLE 1

17 Substituted 2ME$_2$ Derivatives

| Entry | Compound | MDA-MB-231 (IC50 μM) | HUVEC (IC50 μM) | MCF7 Fold stimulation |
|---|---|---|---|---|
| 1 | 2-Methoxyestradiol (2ME$_2$) | 0.5 ± 0.05 | 0.66 ± 0.02 | 1.75 |
| 2 | estra-1,3,5(10)-triene-3,17α-diol | 5.86 +/− 1.03 | 6.79 +/− 0.17 | 1.75 (1) |
| 3 | 2-methoxyestra-1,3,5(10)-triene-3-ol | 1.25 ± 0.97 | 1.43 ± 0.51 | |
| 4 | 17β-aminoestra-1,3,-5,(10)-triene-3,17β-diol | 2.77 ± 1.58 | 21.64 +/− 2.31 | 1.82 (0.6) |
| 5 | 2-methoxy-17-oxime-3-hydroxyestra-1,3,5(10)-triene-17-one | 7.27 +/− 3.80 | 3.45 +/− 2.40 | |
| 6 | 2-methoxy-3,17β-bis(acetyloxy)estra-1,3,5,(10)-triene | 0.59 ± 0.15 | 3.60 ± 2.00 | |
| 7 | 2-methoxy-17β-propaneestra-1,3,5(10)-triene-3-ol | 51.31 ± 3.17 | 34.28 +/− 0.90 | 1.89 |
| 8 | 2-methoxy-17β-methylestra-1,3,5(10)-triene-3-ol | 3.43 +/− 0.81 | 2.36 +/− 1.31 | |
| 9 | 2-methoxy-17(20)-Z-propylideneestra-1,3,5,(10)-triene-3-ol | 6.85 ± 3.06 | 2.77 +/− 0.63 | 3.16 (0.6) |
| 10 | 17(20)-methyleneestra-1,3,5(10)-triene-3-ol | 0.24 ± 0 | 0.19 +/− 0.19 | |
| 11 | 2-methoxy-17β-(N-n-propylamino)estra-1,3,5(10)-triene-3-ol | 17.32 +/− 4.09 | 16.26 +/− 0.50 | 4.87 (1) |
| 12 | 2-methoxy-19-norpregna-1,3,5(10)17(20)-tetraen-3-ol | 1.75 +/− 0.30 (1.05 ± 0.64) | 0.50 +/− 0.01 (0.23 ± 0.07) | |
| 13 | 2-methoxy-17β-ethylestra-1,3,5(10)-triene-3-ol | 5.43 +/− 1.54 | 2.38 +/− 0.10 | |
| 14 | 2-methoxy-17-(4-tosylhydrazone)estra-1,3,5(10)-triene-3-ol | 65.17 +/− 4.43 | 7.07 +/− 2.1 | |
| 15 | 2-methoxy-17(20)-Z-butylideneestra-1,3,5(10)-triene-3-ol | 6.80 +/− 1.5 | 1.88 +/− 0.25 | |
| 16 | 2-methoxy-17β-butylestra-1,3,5(10)-triene-3-ol | 36.36 +/− 5.80 | 11.77 +/− 1.54 | |

These analogs were evaluated in vitro using MDA-MB-231 and MCF-7 breast tumor cells and HUVEC endothelial cells. Structure activity relationships include that inversion of C-17 stereocenter results in an approximately ten-fold drop in anti-proliferative activity. Removal of the 17-hydroxy group to give the dehydroxy derivative give an in vitro profile analogous to 2-methoxyestradiol. Conversion of the 17-hydroxy to a nitrogen functionality conserved some in vitro activity. Incorporation of a methylene group at position 17 results in an increase in in vitro activity compared to 2-methoxyestradiol.

Further evaluation of these compounds can include: in vitro evaluation for antitumor, antiproliferative or antiangiogenic activity using assays such as: in vitro tumor cell line or endothelial cell proliferation assays analyzed by direct cell counts, commercial kits measuring cellular metabolic function including MTT and XTT, or cell counts using metabolic incorporation into DNA of labeled ($^3$H-thymidine) or immunoreactive nucleotide (BrdU); in vitro assay of motility or migration including trans-membrane migration or endothelial cell layer wounding; surrogate in vitro assays for specific functions of $2ME_2$ analogs such as tubulin polymerization or SOD or other enzyme binding or inhibition assays; in vitro assays for induction of apoptosis or other perturbation of cell function including TUNEL and histone analysis, oxygen radical levels, p53 levels or p53 phosphorylation, or analysis of levels or activation state of enzymes in the apoptotic pathway such as caspases or other apoptotic molecules such as death receptors or other receptors associated with caspase activation; ex vivo assays including endothelial outgrowth from bone or aortic rings, tube forming assays, mitogenesis or motility or morphogenesis assays; or in vivo assays including chick embryo chorioallantoic membrane assay (CAM), matrigel plug assay, rabbit or mouse corneal eye pocket angiogenesis assay, liver sponge assay, or in vivo assays of angiogenesis-dependent tumor growth including B16BL6 melanoma metastasis or Lewis Lung primary and metastatic rat or mouse models or tumor xenografts or tumor development in susceptible strains such as AJ mice or mutant mouse strains such as agouti or ras-overexpressing strains or the min mouse or other transgenic or mutant mouse model systems. Examples of further analyses which can be used to determine the suitability of these analogs for use in particular diseases and pathologies include: estrogenic activity which can be assessed in vitro using estrogen dependant MCF-7 proliferation assay, or in animal assays such as uterine weight gain or uterine or vaginal cytology or diestrus time perturbation; metabolic stability which can be analyzed using liver microsomes in vitro, or dosing animals or human subjects and measuring metabolism of the compound or formation of specific metabolites such as oxidation or demethylation products or conjugates using analytical techniques including HPLC, LCMS, GCMS, or LCMSMS; models of inflammation-associated angiogenesis including psoriasis, granuloma and collagen-induced arthritis models; the ApoE −/− knockout mouse model of atherosclerotic angiogenesis; porcine model of restenosis injury; neonatal mouse model of hypoxia-driven retinopathy; measurement of cholesterol levels; assays for antiangiogenic effects on fertility or reproduction or endometriosis including inhibition of angiogenesis during follicular development; assays for effect of antiangiogenic agents on wound healing including skin punch biopsy measurement; and osteoporosis models such as in vitro measurement of osteoclast and osteoblast differentiation, proliferation, and function, ex vivo assessment of bone resorption (pitting), or in vivo measurement of bone density.

For example, one embodiment of the invention includes the modifications listed above at the 17 position and also modifies the methyl ether of 2-methoxyestradiol so that it can not be a substrate for demethylases. Additionally, it has been claimed (U.S. Pat. No. 5,504,074) and demonstrated (Cushman et al *J. Med. Chem.* 1995, 38, 2041–2049) that other electron-rich groups at the 2-position of estradiol (propyne, propene, ethoxy) have good anti-proliferative activity in vitro. It is disclosed that modifications at C-2 of estradiol such as formyl, acetyl, methanol, 1-ethanol, 2-ethanol, amino, alkylamino, dialkyl amino, methyleneamine, methylene alkyl amine and methylene dialkylamine, and alkyl amide are anti-proliferative and anti-angiogenic agents which have reduced or removed estrogenic activity and cannot be metabolized to $2-HO-E_2$ by demethylases. Alkyl is defined as any carbon chain up to 10 carbons in length that is branched or straight. Listed below in Table 2 are data of 2-modified estradiol derivatives in HUVEC, MDA-MB-231 and MCF7 proliferation data. The synthetic paths for preparation of these analogs can be found in Pert et al *Aust. J. Chem.* 1989, 42, 405–419; Lovely et al *Tetrahedron Lett.* 1994, 35, 8735–8738. Gonzalez et al *Steroids* 1982, 40, 171–187; Nambara et al *Chem. Pharm. Bull.* 1970, 18, 474–480; Cushman et al *J. Med. Chem.* 1995, 38, 2041–2049 and methods developed in-house which were discussed previously in this text.

TABLE 2

2 Substituted $E_2$ Derivatives

| Entry | Compound | MDA-MB-231 (IC50 µM) | HUVEC (IC50 µM) | MCF7 Fold stimulation |
|---|---|---|---|---|
| 1 | 2 Methoxyestradiol ($2ME_2$) | 0.5 ± 0.05 | 0.66 ± 0.02 | 1.75 |
| 2 | 2-acetylestra-1,3,5(10)-triene-3,17β-diol | 13.15 ± 1.93 | 19.36 ± 2.11 | 6.1 |
| 3 | 2-formylestra-1,3,5(10)-triene-3,17β-diol | 36.25 ± 1.50 | 4.82 ± 1.31 | |
| 4 | 2-(hydroxymethyl)estra-1,3,5(10)-triene-3,17β-diol | 64.4 +/− 15.5 | 5.62 +/− 1.03 | 3.59 |
| 5 | 2-ethylestra-1,3,5(10)-triene-3,17β-diol | 7.09 +/− 0.67 | 6.03 +/− 4.33 | 6.22 |
| 6 | 2-methylestra-1,3,5(10)-triene-3,17β-diol | 38.61 +/− 5.2 | 4.92 +/− 2.85 | |
| 7 | 2-nitroestra-1,3,5(10)-triene-3,17β-diol | 137.31 +/− 22.1 | 22.86 +/− 1.35 | 3.96 |

TABLE 2-continued

2 Substituted E$_2$ Derivatives

| Entry | Compound | MDA-MB-231 (IC50 μM) | HUVEC (IC50 μM) | MCF7 Fold stimulation |
|---|---|---|---|---|
| 8 | 2-(N,N-dimethylamino)estra-1,3,5(10)-triene-3,17β-diol | 43.57 +/− 4.47 | 5.65 +/− 0.55 | |
| 9 | 2-aminoestra-1,3,5(10)-triene-3-ol | >200 ± 0 | 90.12 +/− 0.34 | |
| 10 | 2-formamideestra-1,3,5(10)-triene-3-ol | 64.88 +/− 10.15 | 3.54 +/− 1.30 | |
| 11 | 2-(N-methylamino)estra-1,3,5(10)-triene-3-ol-HCl | 13.51 +/− 2.18 | 5.18 +/− 1.00 | |
| 12 | 2-(N,N-dimethylamino)estra-1,3,5(10)-triene-3-ol | See HCl form | 37.4, See HCl form | 2.82 |
| 13 | 2-(N,N-dimethylamino)estra-1,3,5(10)-triene-3-ol-HCl | 46.16 +/− 2.42 | 6.32 +/− 0.80 | |
| 14 | 2-aminoestra-1,3,5(10)-triene-3,17β-diol | 67.81 +/− 11.1 | 30.71 +/− 8.48 | |
| 15 | 2-(N,N-dimethylamino)-17(20)-methyleneestra-1,3,5(10)-triene-3-ol-HCL | 39.64 +/− 12.64 | 5.00 +/− 0.54 | |
| 16 | 2-(1'-propynyl)estra-1,3,5(10)-triene-3,17β-diol | 1.86 | | 6.09 |
| 17 | 2-Azidoestra1,3,5(10)-triene-3,17β-diol | 13.27 ± 2.07 | 1.66; 3.51 | |
| 18 | 2-ethoxyestra-1,3,5(10)-triene3,17β-diol | 0.179 | 0.06 | |
| 19 | estra-1,3,5(10)-triene-3-ol | 33.85 ± 2.09 | 8.66 ± 0.89 | |

All of the 2-modified analogs presented in Table 2 have significantly less estrogenic activity (compared to estradiol) as represented by their proliferation index in estrogen dependant MCF-7 cells. Both the 2-hydroxymethyl (entry 4) and 2-formyl (entry 3) derivatives had good antiproliferative activity (IC50<10 microM) in HUVEC cells, whereas the 2-acetyl (entry 2) had poor activity in the same assay. In contrast, 2-hydroxymethyl and 2-formyl had poor activity in breast tumor MDA-MB-231 cells while 2-acetyl-E2 had good activity in this cell line.

Although not wishing to be bound by theory, molecular modeling suggests that there may be a hydrogen bond that forms between the 3-hydroxy group and the methoxy group of 2-methoxyestradiol. This interaction may be important for both 2-methoxyestradiol's anti-proliferative and anti-angiogenic action as well as its non-estrogenic activity. It is disclosed that any group that can be placed at position 2 of estradiol and has the potential to form a hydrogen bond with the 3-hydroxy group is an anti-proliferative and anti-angiogenic agent that lacks estrogenic activity. (Brzozowski et al., Molecular basis of agonism and antagonism in the oestrogen receptor, *Nature* 389:753–758 (Oct. 16, 1997)). Although not wishing to be bound by theory, it is also believed that by modifying position 2,2-methoxyestrone may not be formed. It is possible that by making modifications in the 2-position, conjugation and oxidation to the estrone will not occur.

It is also disclosed that there are non-H-bonding analogs of 2-methoxyestradiol modified at the 2 position with antiproliferative activity and low estrogenicity. These compounds are also contemplated by this invention.

In another example, one embodiment of the invention includes the modifications listed at the 17 position and also modifies the 16 position of 2-methoxyestradiol. Examples of analogs modified at the 16 position are shown in Table 3.

TABLE 3

16 Substituted 2ME$_2$ Derivatives

| Entry | Compound (α/β) | MDA-MB-231 (IC50 μM) | HUVEC (IC50 μM) | MCF7 Fold stimulation |
|---|---|---|---|---|
| 1 | 2-Methoxyestradiol (2ME$_2$) | 0.5 ± 0.05 | 0.66 ± 0.02 | 1.75 |
| 2 | 2-methoxy-16α-methylestra-1,3,5(10)-triene-3,17β-diol | 0.57 ± 0.07 | 0.48 ± 0.02 | |
| 3 | 2-methoxy-16β-methylestra-1,3,5(10)-triene-3,17β-diol | 1.12 ± 0.08 | 1.36 +/− 0.49 | |
| 4 | 2-methoxy-16-ethylestra-1,3,5,(10)-triene-3,17β-diol | 6.42 ± 2.25 | 1.50 +/− 0.51 | 3.33 |
| 5 | 16α-(hydroxymethyl)estra-1,3,5(10)-triene-3,17β-diol | 1.68 ± 0.99 | 11.6 +/− 3.70 | 3.39 |
| 6 | 16β-(hydroxymethyl)estra-1,3,5(10)-triene-3,17β-diol | 5.40 ± 3.10 | 5.31 +/− 3.20 | 2.04 |
| 7 | 2-methoxy-16α-propaneestra-1,3,5(10)-triene-3,17β-diol | 39.9 +/− 7.70 | 5.97 ± 1.54 | |
| 8 | 2-methoxy-16β-propaneestra-1,3,5(10)-triene-3,17β-diol | 28 ± 13.08 | 17.89 ± 1.74 | |
| 9 | 2-methoxy-16β-butaneestra-1,3,5(10)-triene-3,17β-diol | 37.1 ± 1.93 | 4.33 ± 0.87 | |
| 10 | 2-methoxy-16α-butaneestra-1,3,5(10)-triene-3,17β-diol | 47.06 ± 0.09 | 16.81 ± 1.98 | |
| 11 | 2-methoxy-16β-iso-butaneestra-1,3,5(10)-triene-3,17β-diol | 36.6 ± 1.68 | 6.58 +/− 0.29 | 0.87 (0.1) |
| 12 | 2-methoxy-16α-(N,N-dimethylaminomethyl)estra-1,3,5(10)-triene-3,17β-diol | 18.13 ± 6.19 | 38.89 ± 0.11 | |

TABLE 3-continued

16 Substituted 2ME$_2$ Derivatives

| Entry | Compound (α/β) | MDA-MB-231 (IC50 μM) | HUVEC (IC50 μM) | MCF7 Fold stimulation |
|---|---|---|---|---|
| 13 | 2-methoxy-16α-ethylestra-1,3,5(10)-triene-3,17β-diol | 1.16 +/− 0.16 | 0.90 +/− 0.49 | |

Initial screening of epimeric 16-ethyl-2-methoxyestradiol and analogues showed that it is about equipotent to 2-methoxyestradiol in inhibition of HUVEC cell proliferation in vitro.

When 2-methoxyestradiol is metabolized to 2-methoxyestrone, biological activity is greatly reduced. Although not wishing to be bound by theory, it is believed that the present invention adds steric bulk and/or modification of chemical or electrostatic characteristics at positions 16 and 17 of 2-methoxyestradiol for retarding or preventing action of 17β-hydroxysteroid dehydrogenases and co-factor NADP$^+$ on this substrate. Addition of steric bulk and/or modification of chemical or electrostatic characteristics at positions 16 and 17 of 2-methoxyestradiol may retard or prevent conjugation, for example, glucuronidation. It is believed that retardation or prevention of these two metabolic deactivation pathways prolongs the serum lifetime of 2-methoxyestradiol and other steroidal compounds while retaining the desired anti-angiogenic and anti-tumor activity. It is also possible that modifications at positions 16 and 17 prevent demethylation at the 2 position. Preventing the possible metabolism of 2ME$_2$ to 2ME$_1$ may occur by making these steroids poor substrates for 17B-HSD (by either steric and/or electronic effects).

It should be understood that in addition to the ingredients, particularly mentioned above, the formulations of this invention may include other agents conventional in the art having regard to the type of formulation in question, for example, those suitable for oral administration may include flavoring agents.

Experimental Data

The following Examples refer to the compound of the following general formula:

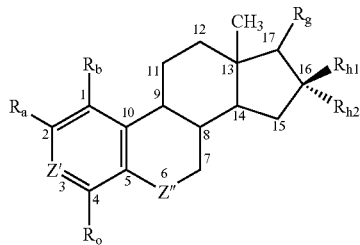

wherein:

a) $R_b$ and $R_o$ are independently —H, —Cl, —Br, —I, —F, —CN, lower alkyl, —OH, —OR$_6$, —CH$_2$—OH, —NH$_2$, or N(R$_6$)(R$_7$), wherein R$_6$ and R$_7$ are independently hydrogen or an alkyl or branched alkyl with up to 10 carbons;

b) $R_a$ is —N$_3$, —C≡N, —CH$_2$—C≡R, —C≡C—R, —C=CH—R, —R—C=CH$_2$, —C≡CH, —CH$_2$—C≡N, >C(H)—C(O)—OR$_3$, —O—R, —R—R$_1$, —O—R—R$_1$, OR(O)R, OR(O)R$_1$, ROR, ROR$_1$, —NHC(O)R$_6$, —NRC(O)R$_6$, —NH$_2$, or N(R$_6$)(R$_7$), wherein R$_6$ and R$_7$ are independently hydrogen or an alkyl or branched alkyl with up to 10 carbons; or a hetero group wherein the hetero group may have more than one hetero atom and may be substituted, where R is H or a straight or branched alkyl with up to 10 carbons or aralkyl, and in any position F may be substituted in or on the carbon chain, and R$_1$ is —OH, —NH$_2$, —Cl, —Br, —I, —F or CF$_3$ when R$_1$ is terminal;

c) Z' is >CH, >COH, CR$_2$, >C—R$_2$—OH, >C—C≡N, >CR$_1$, where R$_2$ is H or a straight or branched alkyl with up to 10 carbons or aralkyl, and in any position may have a hetero substitution in or on the carbon chain by hetero group as defined earlier, or where R$_2$ is an alkyl or branched alkyl with up to 10 carbons, or aralkyl (also referred to herein as arylalkyl), or a hetero group wherein the hetero group may have more than one hetero atom and may be substituted, and R$_1$ is —OH, —NH$_2$, —Cl, —Br, —I, —F or —CF$_3$ when R$_1$ is terminal;

d) >C—Rg is >CH$_2$, >C(H)—OH, >C=O, >C=N—OH, >C(R$_3$)OH, >C=N—OR$_3$, >C(H)—NH$_2$, >C(H)—NHR$_3$, >C(H)—NR$_3$R$_4$, or >C(H)—C(O)R$_3$, where each R$_3$ and R$_4$ is independently an alkyl or branched alkyl with up to 10 carbons or aralkyl; or R$_g$ is i) an alkyl of 1–10 carbon atoms that is straight chain or branched, ii) an alkenyl of 1–10 carbon atoms that is straight chain or branched having one or more double bonds at any position from C to Zo, iii) an alkenyl group of 1–10 carbon atoms that is straight chain or branched having one or more triple bonds at any position where chemically possible, iv) a mono or dialkyl amino group wherein each alkyl chain has from 1–10 carbon atoms and is straight chain or branched, v) (CH$_2$)$_n$—CF$_2$—, (CH$_2$)$_n$—CR$_1$ or (CH$_2$)$_n$—CF$_3$ wherein n=0–10 carbons, or vi) H, and wherein any of i–iv are optionally substituted with an aromatic or heteroaromatic group or optionally substituted with a heterogroup and wherein Rg is either in the α or β position; or Rg is Rg$_1$ and Rg$_2$, and wherein Rg$_1$ may be present or absent and when present is —H, an alkyl, alkenyl, or alkynyl of 1–10 carbon atoms that is straight chain or branched and is optionally substituted, and Rg$_2$ is a hetero group, wherein when Rg$_1$ is absent the heterogroup is bonded to the 17-position with a double bond, and wherein either Rg$_1$ or Rg$_2$ can be in the β position with the other group in the α position, and R$_1$ is —OH, —NH$_2$, —Cl, —Br, —I, —F or CF$_3$ when R$_1$ is terminal;

e) R$_{h1}$ and R$_{h2}$ are independently H, or a straight or branched chain alkyl, alkenyl or alkynyl with up to 10 carbons that is unsubstituted, or substituted with one or more groups selected from a hetero functionality wherein the H is not substituted, or is mono-substituted or is multiply substituted with an alkyl, alkenyl or alkynyl chain up to 10 carbons; a halo functionality (F, Cl, Br or I); an aromatic group optionally substituted with at least one hetero, halo or alkyl; or R$_{h1}$ and R$_{h2}$ are independently a group containing at least one aliphatic or aromatic group optionally substituted with at least one hetero, halo or alkyl, provided that both R$_{h1}$ and R$_{h2}$ are not H;

f) Z" is >CH$_2$, >C=O, >C—OAc, >C(H)—OH, >C=N—OH, >C=N—OR$_5$, >C(H)—C≡N, or >C(H)—NR$_5$R$_5$, wherein each R$_5$ is independently hydrogen, an alkyl or branched alkyl with up to 10 carbons or aralkyl;

and wherein saturated bonds in any ring may be dehydrogenated where chemically possible to someone skilled in the art;

and wherein all stereochemical isomers have either an α or β configuration (R and S; or D- and L-) where chemically possible to someone skilled in the art;

and wherein lower alkyl is defined as a carbon chain having 1–10 carbon atoms which may be branched or unbranched and wherein chemically possible to one skilled in the art.

In some embodiments of the invention, preferably Z" is >COH or >C—OAc. In some embodiments of the invention, preferably Z" is >CH$_2$. In some embodiments of the invention, preferably R$_b$ and R$_o$ are H.

As used herein, "terminal" is defined as "at the end of a chain".

The compounds of the present invention may also be presented as a pharmaceutically acceptable salts.

Examples of heterogroups that may be used in Rg$_2$ include, but are not limited to, ether groups, amino groups, carbonyl groups, haloalkyl, dihaloalkyl, or trihaloalkyl groups, hydroxy groups, ester groups, dialkylamino, or monoalkylamino groups, thiol, thioether, or thioester (phosphate) groups, and oximes.

An example of a compound of the invention comprising an olefin C9–C11 2-methoxyestradiol derivative is shown in Table 4. This compound was prepared by modifying Schwarz's methodology in Schwarz et al., Steroids (1999) 64, 460 (scheme 15).

TABLE 4

Dehydrogenated/Substituted 2ME$_2$ Derivatives

| Compound | MDA-MB-231 (IC50 μM) | HUVEC (IC50 μM) | MCF7 Fold stimulation |
| --- | --- | --- | --- |
| 2 Methoxyestradiol (2ME$_2$) | 0.5 ± 0.05 | 0.66 ± 0.02 | |
| 2-methoxy-estra-1,3,5(10)9(11)-tetraene-3,17β-diol | 0.45 +/− 0.20 | 0.25 +/− 0.03 | |

This additional compounds of Table 5 are also contemplated by this invention.

TABLE 5

Additional 2ME$_2$ Derivatives

| Entry | Compound | MDA-MB-231 (IC50 μM) | HUVEC (IC50 μM) | MCF7 Fold stimulation |
| --- | --- | --- | --- | --- |
| 1 | 2-ethoxy-19-norpregnane-1,3,5(10)17(20)-tetraen-3-ol | | | |
| 2 | 2-(1-propynyl)-19-norpregnane-1,3,5(10)17(20)-tetraen-3-ol | | | |
| 3 | 2-formyl-19-norpregnane-1,3,5(10)17(20)-tetraen-3-ol | | | |
| 4 | 2-formamide-19-norpregnane-1,3,5(10)17(20)-tetraen-3-ol | | | |
| 5 | 2-methyenehydroxy-19-norpregnane-1,3,5(10)17(20)-tetraen-3-ol | | | |
| 6 | 2-ethyl-19-norpregnane-1,3,5(10)17(20)-tetraen-3-ol | | | |
| 7 | 2-methyl-19-norpregnane-1,3,5(10)17(20)-tetraen-3-ol | | | |
| 8 | 2-(1-propenyl)-19-norpregnane-1,3,5(10)17(20)-tetraen-3-ol | | | |
| 9 | 2-ethoxy-17(20)-methyleneestra-1,3,5(10)-triene-3-ol | | | |
| 10 | 2-(1-propynyl)-17(20)-methyleneestra-1,3,5(10)-triene-3-ol | | | |
| 11 | 2-formyl-17(20)-methyleneestra-1,3,5(10)-triene-3-ol | | | |
| 12 | 2-formamide-17(20)-methyleneestra-1,3,5(10)-triene-3-ol | | | |
| 13 | 2-methylenehydroxy-17(20)-methyleneestra-1,3,5(10)-triene-3-ol | | | |
| 14 | 2-ethyl-17(20)-methyleneestra-1,3,5(10)-triene-3-ol | | | |
| 15 | 2-methyl-17(20)-methyleneestra-1,3,5(10)-triene-3-ol | | | |
| 16 | 2-(1-propenyl)-17(20)-methyleneestra-1,3,5(10)-triene-3-ol | | | |
| 17 | 2-ethoxyestra-1,3,5(10)-triene-3-ol | | | |
| 18 | 2-(1-propynyl)estra-1,3,5(10)-triene-3-ol | | | |
| 19 | 2-formylestra-1,3,5(10)-triene-3-ol | | | |
| 20 | 2-formamideestra-1,3,5(10)-triene-3-ol | | | |
| 21 | 2-(methylenehydroxy)estra-1,3,5(10)-triene-3-ol | | | |
| 22 | 2-ethylestra-1,3,5(10)-triene-3-ol | | | |
| 23 | 2-methylestra-1,3,5(10)-triene-3-ol | | | |
| 24 | 2-(1-propenyl)estra-1,3,5(10)-triene-3-ol | | | |
| 25 | 2-ethoxy-17β-methylestra-1,3,5(10)-triene-3-ol | | | |
| 26 | 2-(1-propynyl)-17β-methylestra-1,3,5(10)-triene-3-ol | | | |
| 27 | 2-formyl-17β-methylestra-1,3,5(10)-triene-3-ol | | | |
| 28 | 2-formamide-17β-methylestra-1,3,5(10)-triene-3-ol | | | |
| 29 | 2-methylenehydroxy-17β-methylestra-1,3,5(10)-triene-3-ol | | | |
| 30 | 2-ethyl-17β-methylestra-1,3,5(10)-triene-3-ol | | | |
| 31 | 2-methyl-17β-methylestra-1,3,5(10)-triene-3-ol | | | |
| 32 | 2-(1-propenyl)-17β-methylestra-1,3,5(10)-triene-3-ol | | | |
| 33 | 2-ethoxy-17β-ethylestra-1,3,5(10)-triene-3-ol | | | |
| 34 | 2-(1-propynyl)-17β-ethylestra-1,3,5(10)-triene-3-ol | | | |
| 35 | 2-formyl-17β-ethylestra-1,3,5(10)-triene-3-ol | | | |
| 36 | 2-formamide-17β-ethylestra-1,3,5(10)-triene-3-ol | | | |
| 37 | 2-methylenehydroxy-17β-ethylestra-1,3,5(10)-triene-3-ol | | | |
| 38 | 2-ethyl-17β-ethylestra-1,3,5(10)-triene-3-ol | | | |
| 39 | 2-methyl-17β-ethylestra-1,3,5(10)-triene-3-ol | | | |
| 40 | 2-(1-propenyl)-17β-ethylestra-1,3,5(10)-triene-3-ol | | | |
| 41 | 2-ethoxy-17(20)-propyleneestra-1,3,5(10)-triene-3-ol | | | |
| 42 | 2-(1-propynyl)-17(20)-propyleneestra-1,3,5(10)-triene-3-ol | | | |
| 43 | 2-formyl-17(20)-propyleneestra-1,3,5(10)-triene-3-ol | | | |

TABLE 5-continued

Additional 2ME₂ Derivatives

| Entry | Compound | MDA-MB-231 (IC50 µM) | HUVEC (IC50 µM) | MCF7 Fold stimulation |
|---|---|---|---|---|
| 44 | 2-formamide-17(20)-propyleneestra-1,3,5(10)-triene-3-ol | | | |
| 45 | 2-methylenehydroxy-17(20)-propyleneestra-1,3,5(10)-triene-3-ol | | | |
| 46 | 2-ethyl-17(20)-propyleneestra-1,3,5(10)-triene-3-ol | | | |
| 47 | 2-methyl-17(20)-propyleneestra-1,3,5(10)-triene-3-ol | | | |
| 48 | 2-(1-propenyl)-17(20)-propyleneestra-1,3,5(10)-triene-3-ol | | | |
| 49 | 2-methoxy-17β-methylenehydroxyestra-1,3,5(10)-triene-3-ol | | | |
| 50 | 2-methoxy-17β-(carboxyliacid)-estra-1,3,5(10)-triene-3-ol | | | |

Many of the 2-alkyl, 17-olefin or 17 alkyl estradiol analogs in Table 5 can be prepared as in Scheme 16. This scheme also shows synthetic routes to 2-alkyl, 17-deoxy estratriene analogs. This route starts with the appropriate 2-alkyl-estradiol precursors (Cushman et al *J. Med. Chem.* 1995, 38, 2041 and Cushman et al *J. Med. Chem.* 1997, 40, 2323.) Oxidation using Oppenauer conditions, gives the 2-alkyl-17-estrone. Deoxygenation of the 17 ketone with hydrazine, and KOH gives 2-alkyl-17-deoxyestratriene analogs. Alternatively, if the Wittig reaction used on 2-alkyl-17-estrone analogs, 2-alkyl-17-alkeneestratriene analogs are generated. Catalytic hydrogenation reduces the 17-alkene to give the 17-alkyl analogs.

In the case where the 2-substituents are propene and propynyl, the catalytic reduction step could not be done since these 2-functionalities would also be reduced. Consequently, when the 2-position substituents are an alkene or alkynyl functionality, and the 17 position substituent are alkanes, Scheme 17 was used to prepare this series of analogs. Commercially available 17-estrone was used as the starting material for this route. Using Wittig conditions as above, followed by catalytic hydrogenation 17-alkylestratriene analogs are generated. To prepare the 2-alkynyl substituted analogs, the propynyl group was introduced and the 3-alcohol was protected as the tBDMS ether using Castro's conditions (Castro et al *J. Org. Chem.* 1966, 31, 4071). Subsequent deprotection using TBAF gave 2-propynyl-17-alkyl-estratriene analogs. 2-Alkene substituted analogs can be prepared by protecting the 3-alcohol as a methoxymethyl ether, subsequent 2-formylation (Lovely et al *Tetrahedron Lett.* 1994, 8735; Pert et al *Aust. J. Chem.* 1989, 42, 405) gives the 2-formyl-3-methoxymethylether-17-alkylestratriene analog in Scheme 17. Subsequent Wittig olefination and deprotection with HCl gives the 2-propen-17-alkylestratriene analog series. The 2-formyl in Scheme 17 can also be reduced the alcohol and deprotected to give the 2-methylenehydroxy-17-alkylestratiene analog series.

2-Formyl-17-alkenylestratriene analogs were prepared as in Scheme 18. As in Scheme 17, estrone can be converted to 17-alkenylestratriene analogs using Wittig conditions. Protection of the 3-hydroxy as the methoxymethyl ether and subsequent formylation as in Scheme 17 gives 2-formyl-3-methoxymethylether-17-alkeneestratriene analogs. Deprotection with HCl gives 2-formyl-17-alkeneestratrienes as a final product.

2-nitrogen and 17-alkane or alkene substitutions were incorporated as depicted in Scheme 19. Estrone was converted to 2-nitroestrone with nitric and acetic acids. Reduction of the nitro group to the amine was accomplished via catalytic hydrogenation. Wittig reaction conditions on 2-aminoestrone yielded 2-amino-17-alkeneestratriene analogs. Formylation using formic acid in toluene gave 2-formamide-17-alkeneestratriene analogs. Alternatively, from 2-amino-17-alkeneestratriene catalytic hydrogenation followed by formylation as above gives 2-formyl-17-alkylestratriene analogs.

Scheme 20 describes the coupling of 17-methylenehydroxy and 17-carboxyacids to 2-methoxyestradiol. Using 2-methoxy-17(20)-methyleneestra-1,3,5(10)-triene-3-ol as the starting material, the hydroxy group was protected as a methoxymethyl ether. Hydroboration (general conditions: Mayo et al *Microscale Organic Laboratory,* 1986, pp 132, John Wiley & Sons, NY, N.Y.) give 17-methylenehydroxy estratriene derivative. Deprotection gives 2-methoxy-17-methylenehydroxyestra-1,3,5(10)-triene-3-ol. Oxidation of the 17-methylenehydroxy MOM protected intermediate with potassium permanganate using phase transfer conditions (Lifshitz et al *J. Am. Chem. Soc,* 1987, 109, 7280 and Herriott et al *Tetrahedron Lett.* 1974, 1511.) gives the carboxyacid. Deprotection as above gives the 17-carboxy analog shown in Scheme 20.

Scheme 16

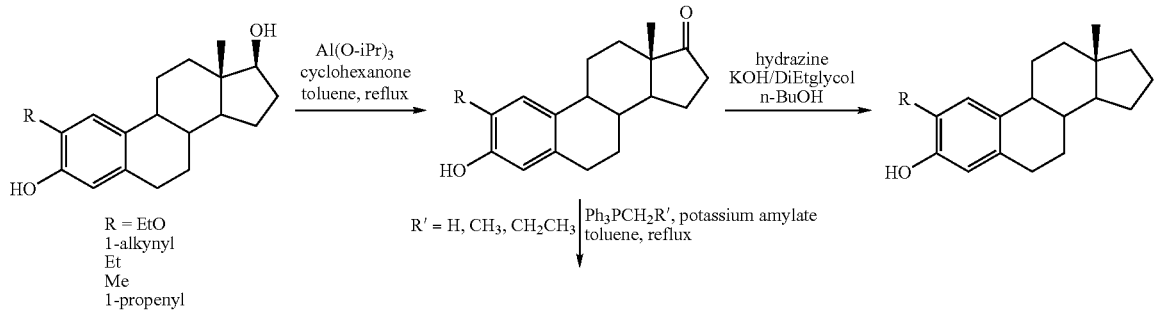

R = EtO
1-alkynyl
Et
Me
1-propenyl

R' = H, CH₃, CH₂CH₃

Ph₃PCH₂R', potassium amylate
toluene, reflux

-continued
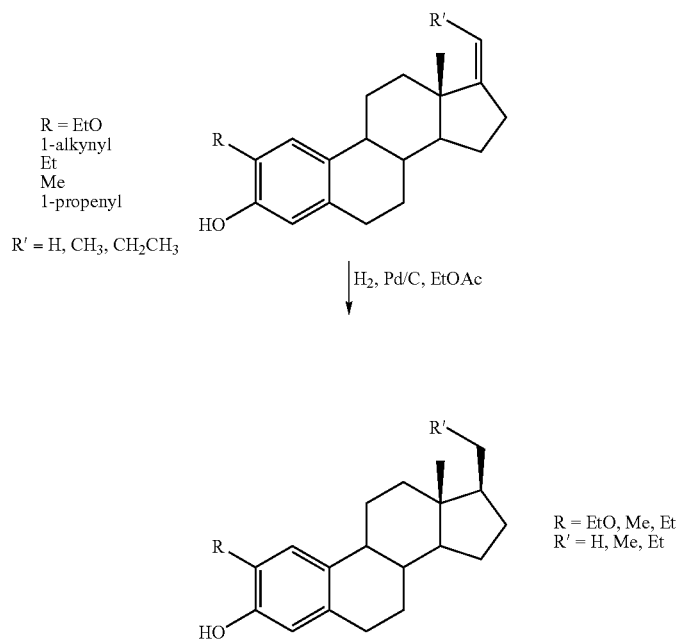
R = EtO
1-alkynyl
Et
Me
1-propenyl
R' = H, CH₃, CH₂CH₃
R = EtO, Me, Et
R' = H, Me, Et
Scheme 17
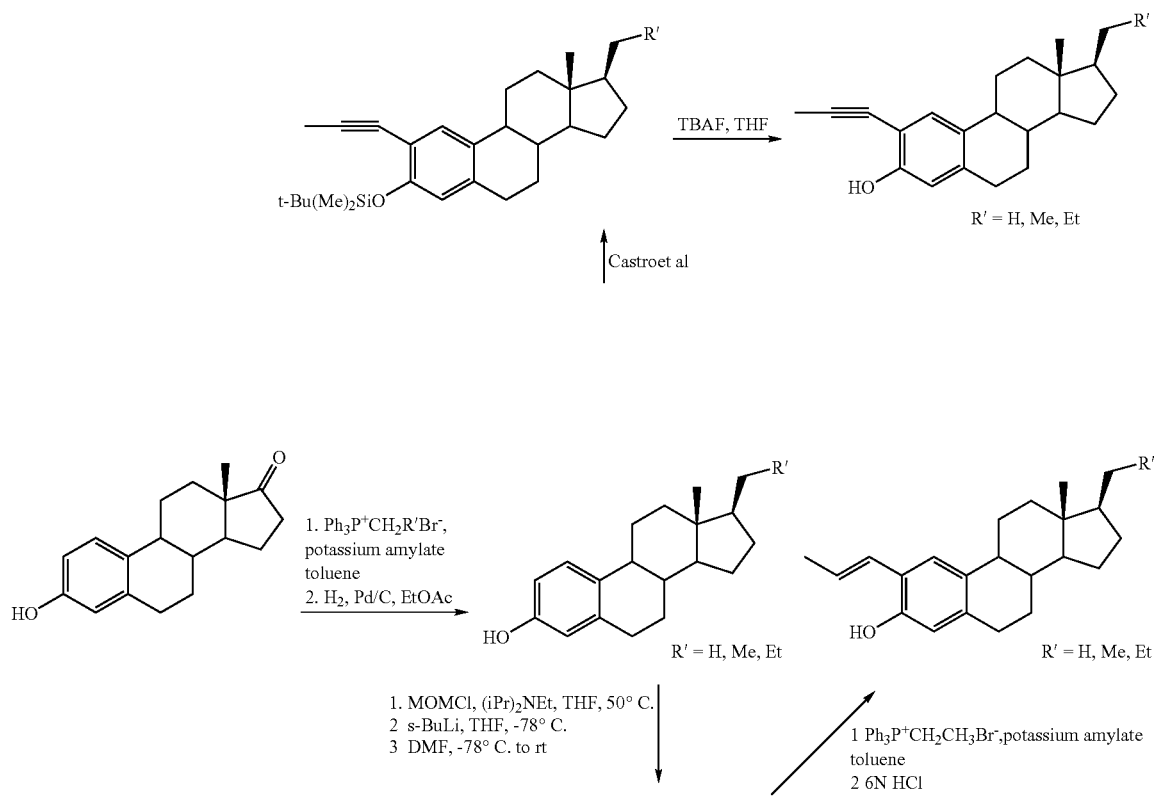
R' = H, Me, Et
Castro et al
1. Ph₃P⁺CH₂R'Br⁻, potassium amylate toluene
2. H₂, Pd/C, EtOAc
1. MOMCl, (iPr)₂NEt, THF, 50° C.
2. s-BuLi, THF, -78° C.
3. DMF, -78° C. to rt
1 Ph₃P⁺CH₂CH₃Br⁻, potassium amylate toluene
2 6N HCl
R' = H, Me, Et

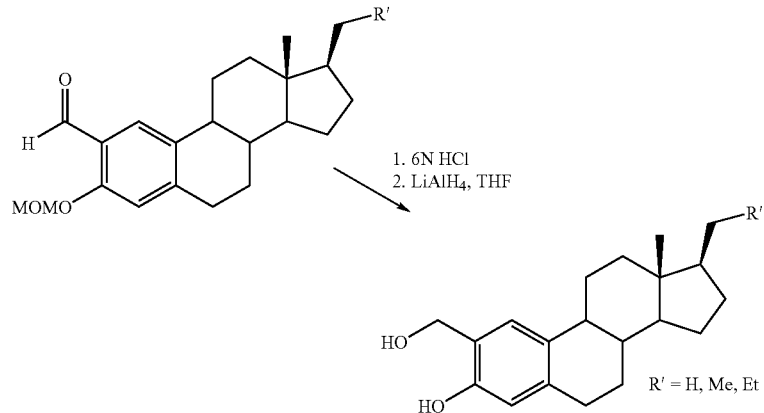
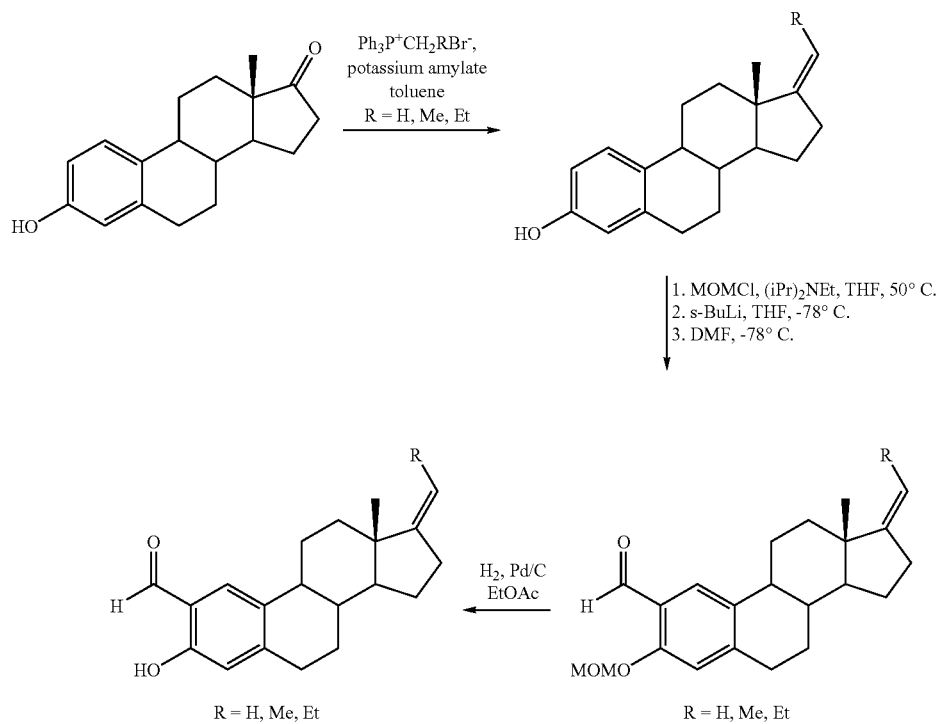
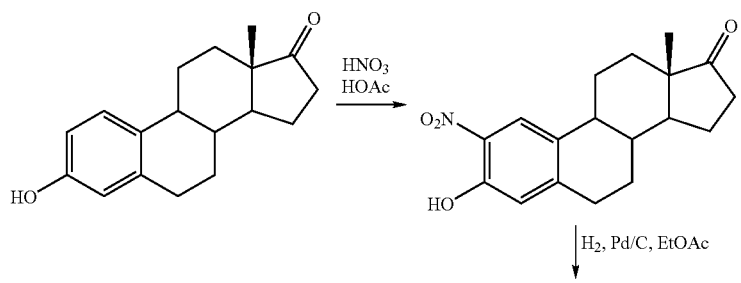

-continued
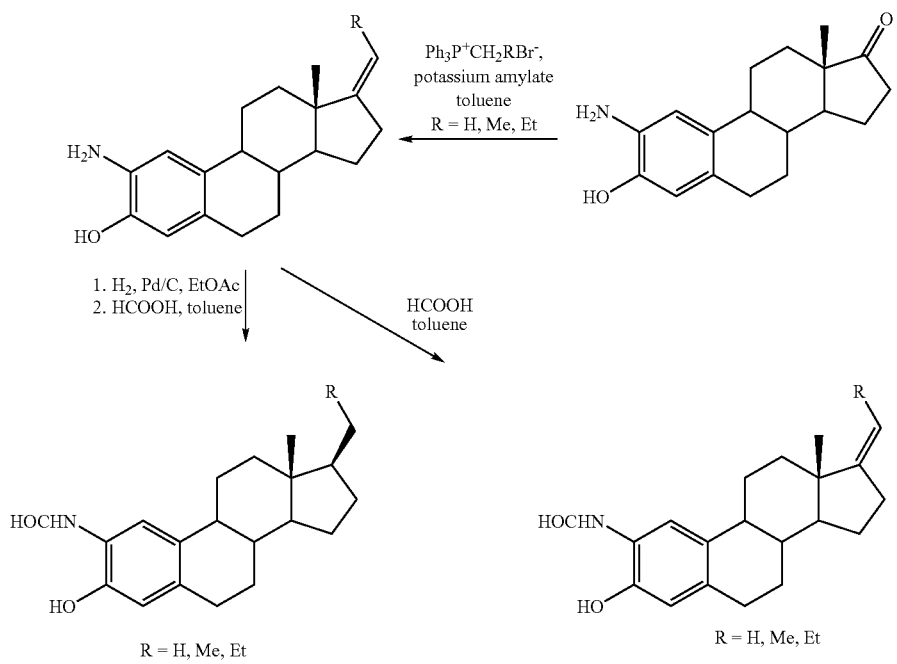
Scheme 20
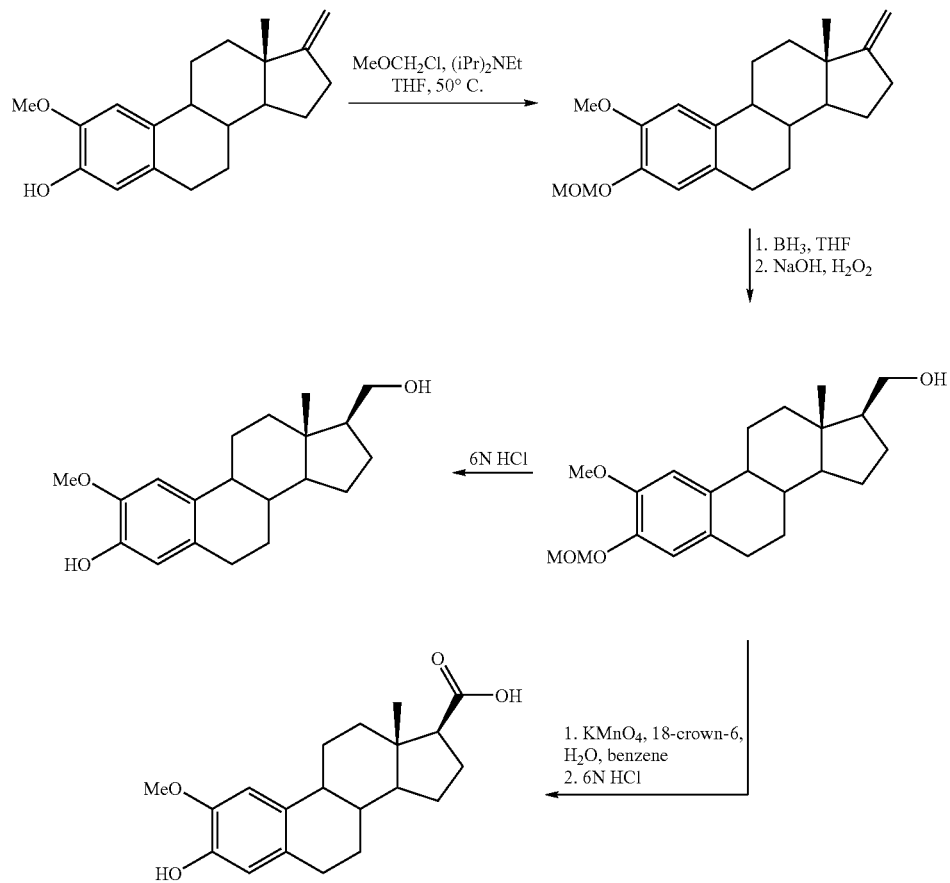

EXAMPLE 1

Synthesis of 2ME$_2$ Derivatives and Modifications at the 17 Position

Synthesis of the 2ME$_2$ derivatives described herein is within the capability of one ordinarily skilled in the art. The synthetic pathways used to prepare derivatives of estradiol modified at the 17 position of the present invention are based on modified published literature procedures for estradiol derivatives cited earlier. Examples of modifications at the 17 position are provided in Examples 2 through 13 below.

EXAMPLE 2

Spectral Data of 17-α-hydroxy-2-methoxyestradiol
(Table 1, Entry 2)

Selected spectral data: $^1$H NMR (300 MHz, CDCl$_3$) δ 6.83 (s, 1H), 6.67 (s, 1H ), 5.44 (s, 1H), 3.88 (s, 3H), 3.83 (d, J=6 Hz, 1H), 2.84–2.75 (m, 2H), 2.41–2.16 (m, 3H), 1.97–1.21 (m, 10H), 0.73 (s, 3H). Anal (C$_{19}$H$_{26}$O$_3$) calcd C=75.46, H=98.67, found C=75.18, H=8.70

EXAMPLE 3

Spectral Data of 17-dehydroxy-2-methoxyestradiol
(Table 1, Entry 3)

Selected spectral data: $^1$H NMR (CDCl$_3$, ppm), 6.85 (1H, s, aromatic), 6.70 (1H, s, aromatic), 5.45 (1H, s, phenol), 3.85 (3H, s, methoxy), 2.85 (dd, J=7.0, 3.5, benzylic), 2.25 (2H, m,), 1.90 (2H, m), 1.75–1.05 (10H, m), 0.75 (3H, s). Anal. (C$_{19}$H$_{26}$O$_2$), Calc.: C=79.68, H=9.09, found: C=79.65, H=9.06.

EXAMPLE 4

Spectral Data of 17-amino-2-methoxyestradiol
(Table 1, Entry 4)

Selected spectral data: $^1$H NMR (300 MHz, CD$_3$OD) δ6.69 (s, 1H), 6.39 (s, 1H), 3.75 (s, 3H), 2.74–2.62 (m, 3H), 2.34–2.20 (m, 1H), 2.19–1.57 (m, 5H), 1.50–1.14 (m, 8H), 0.72 (s, 3H). Anal (C$_{19}$H$_{27}$NO$_2$) calcd C=79.84, H=9.29, found C=80.28, H=9.17

EXAMPLE 5

Spectral Data of 17-oxime (2-methoxyestrone)
(Table 1, Entry 5)

Selected spectral data: $^1$H NMR (CDCl$_3$, ppm), 6.80 (1H, s, aromatic ), 6.70 (1H, s, aromatic ), 5.60 (1H, broad), 3.90 (3H, s, methoxy), 2.85 (m, benzylic), 2.55 (2H, m,), 2.35 (2H, m), 2.15–1.40 (8H, m), 0.95 (3H, s).

EXAMPLE 6

Spectral Data of 3,17-diacetate-2-methoxyestradiol
(Table 1, Entry 6)

Selected spectral data: $^1$H NMR (300 MHz, CD$_3$OD) δ6.90 (s, 1H), 6.75 (s, 1H), 4.71 (dd, J=7.8, 8.4 Hz, 1H), 3.82 (s, 3H), 2.84–2.77 (m, 2H), 2.32 (s, 3H), 2.32–2.15 (m, 2H), 2.08 (s, 3H), 1.95–1.22 (m, 7H), 0.85 (s, 3H). Anal (C$_{23}$H$_{30}$O$_5$) calcd C=71.48, H=7.82, found C=71.24, H=7.82.

EXAMPLE 7

Synthesis of Estradiol (E$_2$) Derivatives and Modifications at the 2 Position

Synthesis of the E$_2$ derivatives described herein is within the capability of one ordinarily skilled in the art. A specific description of the synthesis of the E$_2$ derivatives having modifications at the 2 position and analogs discussed herein can be found in M. Cushman, H -M. He, J. A. Katzenellenbogen, C. M. Lin and E. Hamel, Synthesis, antitubulin and antimitotic activity, and cytotoxicity of 2-methoxyestradiol, and endogenous mammalian metabolite of estradiol that inhibits tubulin polymerization by binding to the colchicine binding site, J. Med. Chem., 38(12): 2042 (1995); and M. Cushman, H -M. He, J. Katzenellenbogen, R. Varma, E. Hamel, C. Lin, S. Ram and Y. P. Sachdeva, Synthesis of analogs of 2-methoxyestradiol with enhanced inhibitory effects on tubulin polymerization and cancer cell growth, J. Med. Chem. 40(15): 2323 (1997).

EXAMPLE 8

Synthesis of 2ME$_2$ Derivatives and Modifications at the 16 Position

The synthetic pathways used to prepare the derivatives of the estradiol derivatives modified at the 16 position of the present invention are based on modified published literature procedures for estradiol derivatives. (Trembley et al., Bioorganic & Med. Chem. 1995 3, 505–523; Fevig et al., J. Org. Chem., 1987 52, 247–251; Gonzalez et al., Steroids 1982, 40, 171–187; Trembley et al., Synthetic Communications 1995, 25, 2483–2495; Newkome et al., J. Org. Chem. 1966, 31, 677–681; Corey et al Tetrahedron Lett 1976, 3–6; and Corey et al., Tetrahedron Lett, 1976, 3667–3668). Examples of selected modifications are provided in Examples 16 through 38 below.

EXAMPLE 9

Preparation of 3-Benzyl-2-methoxyestradiol
(Scheme 1A)

2-Methoxyestradiol (10.09 g, 33.4 mmol) and potassium carbonate (22 g, 278 mmol) were suspended in anhydrous ethanol and cooled to 0° C. Benzyl bromide (11.4 mL, 95.8 mmol) was added dropwise, and following the addition, the mixture was brought to reflux for 8 h. The solution was cooled to room temperature (rt), and the solvent was removed via rotoevap. The resulting residue was diluted with approximately 200 ml water, and washed with ethyl acetate (3×200 mL). The combined organics were washed with water (200 mL), sodium bicarbonate (saturated (satd), 200 mL) and brine (200 mL). Dry with sodium sulfate, filter and roto-evaporation (rotoevap). Product was dried under vacuo with occasional gentle heating using a heat gun to give a yellowish glass (13.54 g, quanitative yield) and used without further purification.

Selected spectral data: $^1$H- NMR (300 MHz, CDCl$_3$) δ 7.29–7.53 (m, 5H), 6.88 (s, 1H), 6.65 (s, 3H), 5.11 (s, 2H), 3.87 (s, 3H), 3.7 (t J=8 Hz, 1H), 0.80 (s, 3H). FT-IR (neat) 3341, 2920, 2864, 1605, 1513, 1453, 1254, 1211, 1117, 1022 cm$^{-1}$.

EXAMPLE 10

Preparation of 3-Benzyl-2-Methoxyestrone (Scheme 1A)

Oxalyl chloride (38 mmol, 19 mL, 2M, methylene chloride) was added to anhydrous methylene chloride (25 mL) and cooled to −46° C. Methyl sulfoxide (5.40 mL, 76 mmol) was added dropwise, and the mixture was stirred for 2 minutes. 3-Benzyl-2-methoxyestradiol in methylene chloride/methyl sulfoxide (10 mL/15 mL) and added within 5 minutes and the resulting mixture was stirred for 1 h. Triethyl amine (170 mmol, 23.5 mL) was added drop-wise, stirred 5 minutes and warmed to rt. Water (~200 mL) was added and the mixture was washed with methylene chloride (3×200 mL). The combined organics were washed with water (200 mL), dilute HCl (1% aq., 200 mL), sodium carbonate (satd, 200 mL) and brine (200 mL). The organics were dried with magnesium sulfate, filtered and rotoevaped to give a white solid. The solid was crystallized with hot ethanol to give white crystals (9.94 g, 25.5 mmol, 76% overall yield from 2-methoxyestradiol).

Selected spectral data: $^1$H-NMR (300 MHz, CDCl$_3$) δ 7.28–7.4 (m, 5H), 6.86 (s, 1H), 6.66 (s, 1H), 3.88 (s, 3H), 0.94 (s, 3H). IR (neat) 2920, 1731, 1519, 1202, 1012 cm$^1$.

EXAMPLE 11

Representative Preparation of 16α-alkyl-3-benzyl-2-methoxyestrone (Scheme 13)

Lithium diisopropyl amide (2M, Aldrich, heptane/THF/ethylbenzene) was dissolved in THF and cooled to −78° C., and 3-benzyl-2-methoxyestrone in THF (10 mL) was added dropwise. Following addition, the mixture was warmed to 0° C. and stirred 1 hour (h). The mixture was then cooled to −78° C. and DMPU (1 mL) followed by crotyl bromide (205 µL, 2.0 mmol) were added dropwise. The mixture was warmed to rt over 4 h. The reaction was quenched by carefully adding water (100 mL) and washing with ethyl acetate (2×100 mL). The combined organics were washed with water (100 mL) and brine (100 mL). The solution was dried with magnesium sulfate, filtered and rotoevaped. The crude product was purified using hexane/ethyl acetate (9:1) SiO$_2$ Biotage FLASH apparatus. 680 mg (1.53 mmol) of product was obtained and approximately 121 mg (0.31 mmol) of starting material was recovered (90% yield based on recovered starting material). Diastereomeric ratio of 16 α/β is approximately 2:1 (s H18 signals at 0.88, 0.79 ppm).

Selected spectral data: $^1$H-NMR (300 MHz, CDCl$_3$) δ 7.28–7.48 (m, 5H), 6.86 (s, 1H), 6.66 (s, 1H), 5.34–5.59(m, 2H), 5.13 (s, 2H), 3.88 (s, 3H), 0.87 & 0.97 (s, total 3H, ratio 1:2).

EXAMPLE 12

Representative Preparation of 16-alkyl-16-methoxycarbonyl-3-benzyl-2-methoxyestrone (Scheme 12)

3-benzyl-16-carbomethoxy-2-methoxyestrone (0.840 g, 1.87 mmol, prepared as in Example 15), potassium hydride (1.5 g, 10.9 mmol, 30% mineral oil dispursion, washed in hexanes) and 18-crown-6 (120 mg, 0.4 mmol) was mixed in THF (40 mL) and refluxed for 1 h. The mixture was cooled to rt, and allyl bromide (537 µL, 6.2 mmol) was added and the mixture was refluxed for 18 h. After cooling to rt, the reaction was quenched by carefully adding approximately 2 ml of water with stirring, then adding an additional 100 mL water. This mixture was washed with ethyl acetate (2×100 mL) and the combined organics were washed with brine (100 mL). The organics were dried with magnesium sulfate, filtered and rotoevaped. Purification using 85:5 hexanes:ethyl acetate SiO$_2$ Biotage FLASH apparatus yielded 697 mg of product (1.42 mol, 76% yield).

Selected spectral data: $^1$H-NMR (300 MHz, CDCl$_3$) δ 7.28–7.48 (m, 5H), 6.85 (s, 1H), 6.66 (s, 1H), 566–5.79 (m, 1H), 5.15–5.20 (m, 2H), 5.13 (s, 2H), 3.88 (s, 3H), 3.75 (s, 3H), 0.99 (s, 3H).

EXAMPLE 13

Representative Decarboxylation of 16-alkyl-16-methoxycarbonyl-3-benzyl-2-methoxyestrone (Scheme 12)

16-allyl-16-carbomethoxy-3-benzyl-2-methoxyestrone (697 mg, 1.42 mmol), lithium chloride (1.15 g, 27 mmol), water (485 µL, 27 mmol) were dissolved in DMF (63 mL) and refluxed for 20 h. Cool to rt, add 1N HCl (100 mL) and wash with ether (2×100 mL) the combined organics were washed with water (100 mL), and brine 100 mL), dry with magnesium sulfate, filter and rotoevap. Purification by 85:15 hexanes:ethyl acetate SiO$_2$ Biotage Flash apparatus gave 271 mg product and 189 mg recovered starting material. Starting material was resubjected to the reaction (308 mg LiCl, 132 µL, water, 17 mL DMF) for 28 h and worked up as above to give 130 mg product. Overall yield for reaction was 66% (401 mg, 0.93 mmol).

Selected spectral data: $^1$H-NMR (300 MHz, CDCl$_3$) δ 7.28–7.48 (m, 5H), 6.85 (s, 1H), 6.65 (s, 1H), 5.69–5.88 (m, 1H), 5.13 (s, 2H), 5.00–5.08 (m, 2H), 5.88 (s, 3H), 0.98 nd 0.88 (s, total 3H, ratio 1:1.4). FT-IR (neat), 2925, 2855, 1726, 1514, 1214, 1103 cm$^{-1}$.

EXAMPLE 14

Preparation of 16-methane-dimethylenamine-3-benzyl-2-methoxyestrone (Scheme 14)

3-benzyl-2-methoxyestrone (1.51 g, 3.87 mmol) was suspended in tert-butoxy bis(dimethylamino)methane (1.64 mL, 8.13 mmol) and heated in an oil bath (155° C.) for 1.5 h, during which time the steroid dissolved. The reaction mixture was cooled to rt, and poured into ice water (100 mL) and washed with methylene chloride (2×100 mL). The organics were washed with brine (100 mL) dried with magnesium sulfate, filtered and rotoevaped to give product which was used without further purification (1.82 g, quanitative yield).

Selected spectral data: $^1$H-NMR (300 MHz, CDCl$_3$) δ 7.23–7.47 (m, 5H), 6.87 (s, 1H), 6.64 (s, 1H), 5.12 (s, 2H), 3.88 (s, 3H), 3.0 (s, 6H), 0.91 (s, 3H).

EXAMPLE 15

Preparation of 16-methoxycarbonyl-3-benzyl-2-methoxy estrone (Scheme 12)

3-Benzyl-2-methoxyestrone (1.6113 g, 2.978 mmol) was dissolved in THF (15 mL), cooled to −78° C. and lithium diisopropyl amide (2M, Aldrich, Heptane/THF/ethylbenzene) was added dropwise and stirred for 1 h. Methyl cyanoformate (237 µL, 3 mmol) in DMPU (1 mL) was added and the mixture warmed to rt over 18 h. Water (100 ml) was carefully added, and the mixture was washed with ethyl acetate (3×100 mL) and the combined organics were washed with brine (100 mL), dried with sodium sulfate, filtered and rotoevaped. Final purification of product using hexane:ethyl acetate (85:15) then switching to hexane: ethyl acetate (75:25) SiO$_2$ flash column yielded 806 mg product (1.8 mmol, 60%).

Selected spectral data: $^1$H-NMR (300 MHz, CDCl$_3$) δ 7.28–7.48 (m, 5H), 6.85 (s, 1H), 6.66 (s, 1H), 5.13 (s, 2H), 3.88 (s, 3H), 3.78 (s, 3H), 3.23 (dd, J=9, 10 Hz, 1H), 1.0 (s, 3H). FT-IR (neat) 2929, 2860, 1750, 1723, 1604, 1508, 1211, 1014 cm$^{-1}$.

EXAMPLE 16

Representative Procedure for Preparation of 16-alkyl-3-benzyl-2-methoxyestra-17β-diol (Scheme 11)

16α-crotyl-3-benzyl-2-methoxyestrone (680 mg, 1.53 mmol) was dissolved in anhydrous THF (10 mL), and cooled to −78° C. Lithium aluminum hydride (3.06 mmol, 116 mg) was added and the solution was stirred for 2 h. The reaction was quenched by carefully adding water (2 mL) and warming to rt, then adding additional 50 mL portion of water. The mixture was washed with ethyl acetate (2×50 mL) and the combined organics were washed with water (50 mL), brine (50 mL), dried with magnesium sulfate, filtered and rotoevaped. The mixture was purified with 3:1 hexane: ethyl acetate SiO$_2$ Biotage FLASH apparatus to give 500 mg purified product (1.12 mmol, 73% yield).

Selected spectral data: $^1$H-NMR (300 MHz, CDCl$_3$) δ 7.28–7.48 (m, 5H), 6.87 (s, 1H), 6.64 (s, 1H), 5.47–5.56 (m, 2H), 5.12 (s, 2H), 3.88 (s, 3H), 3.8 (d, J=9 Hz) and 3.33 (d, J=8 Hz) total 1H, ratio 1:1.7, 0.84 and 0.81 (s, 3H total).

EXAMPLE 17

Preparation of 16-methanol-3-benzyl-2-methoxyestradiol (Scheme 12)

Reaction procedure and work up as above, (used 806 mg, 1.8 mmol 16-carbomethoxy-3-benzyl-2-methoxyestrone), except warm to rt for 2 h before quenching. Purify final product with 3:2 hexane:ethyl acetate SiO$_2$ flash column. Obtain 304 mg β isomer, 51 mg α isomer which were separated by chromatography.

Selected spectral data: $^1$H-NMR (300 MHz, CDCl$_3$) δ Major isomer 7.28–7.48 (m, 5H), 6.87 (s, 1H), 6.64 (s, 1H), 5.12 (s, 2H), 3.97 (d, J=10 Hz), 3.88 (s and obscured d, 4H), 3.67 (dd, J=4, 7 Hz, 1H), 0.87 (s, 3H). Minor isomer 7.28–7.47 (m, 5H), 6.86 (s, 1H), 6.64 (s, 1H), 3.88 (s, 3H), 3.83 (d, J=14 Hz, 1H), 3.69 (t, J=9 Hz, 1H), 3.54 (d, J=7 Hz, 1H), 0.87 (s, 3H).

EXAMPLE 18

Representative Debenzylation of 16-alkyl1–13-benzyl-2-methoxyestradiol (Scheme 11)

16α-crotyl-3-benzyl-2-methoxyestradiol (500 mg, 1.12 mmol) was dissolved in ethyl acetate (25 mL) in Parr reaction bottle. The bottle was flushed with argon, and Pd/C (10%, 2.5 g) was added. The bottle was fitted to a Parr hydrogenator, filled and purged with hydrogen five times, pressurized to 50 psi, and agitated for 24 h. The mixture was filtered through a celite pad, rotoevaped and purified with a 3:1 hexane ethyl acetate SiO$_2$ flash column. Obtain 358 mg product (1.0 mmol, 89%).

Selected spectral data: $^1$H-NMR (300 MHz, CDCl$_3$) δ 6.81 (s, 1H), 6.66 (s, 1H), 3.87 (s, 3H), 3.76 (d, J=10 Hz) and 3.29 (d, J=8 Hz) (total 1H, ratio 1:2), 0.82 and 0.79 (s, 3H) FT-IR (neat) 3245, 2914, 1606, 1523, 1414, 1258, 1028 cm$^{-1}$. Analysis calculated (Anal. Calcd) for C$_{20}$H$_{34}$O$_3$: C, 77.44; H, 9.56. Found: C, 76.64; H, 9.51.

EXAMPLE 19

16β-methyl-2-methoxyestradiol (Table 3, Entry 3)

Selected spectral data: $^1$H-NMR (300 MHz, CDCl$_3$) δ6.81 (s, 1H), 6.66 (s, 1H), 3.87 (s, 3H), 3.73 (d, J=10 Hz) and 3.23 (d, J=8 Hz) (total 1H, 2:1), 0.83 and 0.81(s, 3 H total). Anal. Calcd for C$_{20}$H$_{28}$O$_3$, 1/4 H$_2$O: C, 74.85; H, 8.95. Found: C, 74.93; H, 8.94.

EXAMPLE 20

16α-methyl-2methoxyestradiol (Table 3, Entry 2)

Selected spectral data: 1H-NMR (300 MHz, CDCl$_3$) δ6.81 (s, 1H), 6.66 (s, 1H), 3.87 (s, 3H), 3.23 (d, J=7 Hz) (s, 1H), 0.81 (s, 3 H). Anal. Calcd for C$_{20}$H$_{28}$O$_3$, 1/4 H$_2$O: C, 74.85; H, 8.95. Found: C, 74.98; H, 8.65.

EXAMPLE 21

Racemic 16-ethyl-2-methoxyestradiol (Table 3, Entry 4)

Selected spectral data: 1H-NMR (300 MHz, CDCl$_3$) δ 6.82 (s, 1H), 6.66 (s, 1H), 3.88 (s, 3H), 3.76 (d, J=9 Hz) and 3.30 (d, J=10 Hz), (1H total, ratio 1:1), 0.83 and 0.79 (s, 3H total). FT-IR (neat) 3214, 2918, 1605, 1522, 1229, 1201, 1024 cm$^{-1}$. Anal. Calcd for C$_{21}$H$_{30}$O$_3$:C, 76.33; H, 9.15. Found: C, 76.18; H, 9.16.

EXAMPLE 22

16α-n-propyl-2-methoxyestradiol (Table 3, Entry 7)

Selected spectral data: 1H-NMR (300 MHz, CDCl$_3$) δ6.81 (s, 1H), 6.66 (s, 1H), 5.43 (s, 1H), 3.87 (s, 3H), 3.29 (t, J=7 Hz, 1H), 0.95 (t, J=7 Hz, 3H), 0.83 and 0.80 (s, total 3H, ratio 7.3:1). Anal. Calcd for C$_{22}$H$_{32}$O$_3$:C, 76.69; H, 9.37. Found: C, 76.55; H, 9.44.

EXAMPLE 23

16β-n-propyl-2-methoxyestradiol (Table 3, Entry 8)

Selected spectral data: 1H-NMR (300 MHz, CDCl$_3$) δ 6.81 (s, 1H), 6.66 (s, 1H), 3.87 (s, 3H), 3.76 (d, J=10 Hz) and 3.29 (t, J=7 Hz) (total 1H, ratio 2:1), 0.95 (t, J=7 Hz, 3H), 0.83 and 0.80 (s, total 3H). FT-IR (neat) 3411, 2923, 1504, 1446, 1267, 1202, 1118, 1024 cm$^{-1}$. Anal. Calcd for C$_{22}$H$_{32}$O$_3$, 1/4 H$_2$O: C, 75.71; H, 9.39. Found: C, 75.61; H, 9.33.

EXAMPLE 24

16,β-n-butyl-2-methoxyestradiol (Table 3, Entry 9)

Selected spectral data: 1H-NMR (300 MHz, CDCl$_3$) δ 6.81 (s, 1H), 6.66 (s, 1H), 5.43 (s, 1H), 3.88 (s, 3H), 3.76 (d, J=10 Hz) 3.29 (d, J=8 Hz) (total 1H, ratio 2.6:1), 0.83 and 0.80 (s, total 3H). FT-IR (neat) 3221, 2921, 1594, 1504, 1416, 1265, 1200, 1021 cm−1. Anal. Calcd for $C_{23}H_{34}O_3$: C, 77.04; H, 9.56. Found: C, 77.06; H, 9.65.

EXAMPLE 25

16β-isobutyl-2-methoxyestradiol (Table 3, Entry 11)

Selected spectral data: 1H-NMR (300 MHz, CDCl$_3$) δ 6.81 (s, 1H), 6.66 (s, 1H), 5.43 (s, 1H), 3.88 (s, 3H), 3.77 (dd, J=9, 10 Hz) and 3.26 (t, J=7 Hz) (total 1 H, ratio 2:1), 0.84 and 0.80 (s, total 3H). IR (neat) 3525, 2913, 1506, 1258, 1202, 1026 cm$^{-1}$. Anal. Calcd for $C_{22}H_{30}O_3$: C, 76.69; H, 9.37. Found: C, 76.82; H, 9.47.

EXAMPLE 26

16β-methyl(dimethyl amine)-2-methoxyestradiol (Table 3, Entry 12)

Selected spectral data: 1H-NMR (300 MHz, CDCl$_3$) δ 6.81 (s, 1H), 6.65 (s, 1H), 3.88 (s) and 3.85 (obscured d) (total 4H), 2.28 (s, 6H), 0.87 (s, 3H). Anal. Calcd for $C_{22}H_{33}O_3N$, 1/4 $H_2O$: C, 72.59; H, 9.28; N, 3.85. Found: C, 72.80; H, 9.17; N, 3.66.

EXAMPLE 27

16,β-methylenehydroxy-2-methoxyestradiol (Table 3, Entry 6)

Selected spectral data: 1H-NMR (300 MHz, CDCl$_3$) δ6.78 (s, 1H), 6.61 (s, 1H), 3.92 (d, J=11 Hz, 1H), 3.84 (s, 3H), 3.80 (d, J=10 Hz, 1H), 3.63 (d, J=8, 11 Hz, 1H), 0.83 (s, 3H). FT-IR (neat) 3283, 3091, 2919, 1602, 1513, 1445, 1204, 1119, 1013 cm$^{-1}$. Anal. Calcd for $C_{20}H_{28}O_4$: C, 72.25; H, 8.49. Found: C, 72.24; H, 8.48.

EXAMPLE 28

16β-methylenehydroxy-2-methoxyestradiol (Table 3, Entry 5)

Selected spectral data: 1H-NMR (300 MHz, CDCl$_3$) δ 6.77 (s, 1H), 6.61 (s, 1H), 3.84 (s, 3H), 3.84 (dd, J=7, 8 Hz, 1H), 3.61 (dd, J=9, 11 Hz, 1H), 3.45 (d, J=8 Hz, 1H), 0.83 (s, 3H).

EXAMPLE 29

MDA-MB-231 In Vitro Cellular Proliferation Inhibition

MDA-MB-231 Cells and Culture Conditions

Table 3 shows the results of antiproliferative activity tests of 2-methoxyestradiol analogs of the present invention modified at the 16 position in cells and tumor.

MDA-MB-231 human breast carcinoma cells were grown in DMEM containing 10% FCS (Hyclone Laboratories, Logan Utah) and supplemented with 2 mM L-Glutamine, 100 units/ml penicillin, 100 μg/ml streptomycin (Irvine Scientific, Santa Anna, Calif.).

Proliferation Assays

MDA-MB-231 cells were plated at 5000 cells/ml in 96-well plates. After allowing the cells to attach overnight, the appropriate fresh media were applied containing differing concentrations of 2-ME2 or derivatives thereof, as described below. Drug was dissolved in DMSO (Sigma, St. Louis, Mo.) and added to the wells in a volume of 200 μl. Cells were incubated for two days at 37° C.; at 32 h BrdU was added. BrdU cell proliferation assay (a nucleotide analogue that is incorporated into DNA) was performed as described by the manufacturer (Roche). Each condition was prepared in triplicate and the experiments were carried out a minimum of two times. Results presented are means +/− SE.

EXAMPLE 30

HUVEC In Vitro Cellular Proliferation Inhibition

HUVEC Cells and Culture Conditions

HUVEC cells were grown in EGM (Clonetics).

Proliferation Assays

HUVEC cells were plated at 5000 cells/ml in 96-well plates. After allowing the cells to attach overnight, the cells were washed with PBS and incubated in the absence of growth factor for 24 h (EBM, 2% FCS, Clonetics). Cells were treated with increasing concentrations of drug in EBM containing 2% FCS and 10 ng/ml bFGF for 48 h at 37° C. Drug preparation, volumes added and BrdU proliferation assay were performed as indicated above.

2-Methoxyestradiol is a potent anti-angiogenic and anti-tumor agent. In order to assess the biological activity of modifications at position 16, the anti-proliferative activity of these analogs was evaluated on human umbilical vein endothelial cells (HUVEC) and breast carcinoma cell line, MDA-MB-231 as models for the anti-angiogenic and anti-tumor activity, respectively. It was found that a decrease (approximately 18 fold) in anti-proliferative activity occurs as steric bulk increased (note trend from R=Et to R=Bu). The most active compound in this series is 16α-methyl, which has similar activity to 2-methoxyestradiol.

The MDA-MB-231 tumor cell line has a much greater sensitivity to substitutions at position 16 compared to HUVEC cells. Any group at position 16 larger than ethyl has a significant decrease in antiproliferative activity (IC50>22 μM). 16α-methyl has better activity than 2-methoxyestradiol, whereas 16β-methyl (which had a 1:2 mixture of α:β) has about 5-fold less activity than 2-methoxyestradiol, and racemic 16-ethyl has about a 3-fold drop in activity compared to 2-methoxyestradiol.

MCF7 cells, an estrogen dependent breast carcinoma cell line, were maintained in DMEM/F12 (1:1) containing 10% (v/v) fetal bovine serum (Hyclone Laboratories, Logan, Utah) and 1×antibiotic-antimytotic. MCF7 cells were used between passage 60 and passage 90. For MCF7 estrogen-dependent proliferation assay the cells were seeded in complete media at 20–30,000 cells/well in a 24 well plate. After allowing the cells to adhere overnight the seeding density was determined by cell counts. Cells were washed with PBS (37° C.) and starved by placing them in IMEM-phenol red free media containing 2% charcoal-dextran fetal bovine-stripped serum (Georgetown University) and 1×antibioticantimitotic. After 3 days of starvation, cells were treated with or without increasing concentrations of compounds, replacing the media every 2–3 days and counted after 8 or 10 days of treatment. Proliferation was measured by cell counting using a Coulter Z1 cell counter (Coulter Corporation, Hialeah, Fla.). Each condition was done in triplicate.

These data indicate that it is possible to design $2ME_2$ analogs that are selective anti-angiogenic agents. For example, 16α-propyl is more than ten-fold less active in inhibiting tumor growth while it has good activity inhibiting endothelial cell proliferation. Other examples include: 16β-propyl (4-fold difference), 16β-i-butyl (5-fold difference), 16β-n-butyl (4-fold difference) and 16β-methanol (10-fold difference). Additionally, a small alkyl group at position 16 can be added without significantly altering the anti-proliferative activity of the molecule.

EXAMPLE 31

17(20)-methyleneestra-1,3,5(10)-triene-3-ol (Table 1, Entry 10)

Representative procedure for preparation of 17-olefin-2-methoxyestrone analogs: Potassium-tert-amylate (1.54 M, toluene, 4.35 mL 6.69 mmol, prepared as in Schow et al *J. Org. Chem.* 1979, 44, 3760) was added to a suspension of methyl triphenylphosphonium bromide (2.39 g, 6.69 mmol) in anhydrous benzene and refluxed for 30 min. 2-Methoxyestrone (300 mg, 1 mmol) in warm benzene (5 mL) was added and the mixture was refluxed for 3 h. The reaction was cooled to rt, poured into 100 mL water, washed with ether (2×100 mL). The combined organics were washed with 6 M HCl (1×100 mL), NaHCO$_3$ (satd, 1×100 mL), water (1×100 mL), and brine (1×100 mL). Dry with sodium sulfate, filter and rotoevap to give a semi solid-yellowish oil. Purify by silica gel column chromatography using 95:5 chloroform:methanol as an eluent. Obtain 220 mg 17(20)-methyleneestra-1,3,5(10)-triene-3-ol (0.738 mmol, 73 % yield). Selected spectral data: $^1$H NMR (300 MHz, CDCl$_3$) δ 6.83 (s, 1H), 6.67 (s, 1H), 5.44 (br s, 1H), 4.70 (t, J=2.26 Hz, 2H), 3.89 (s, 3H), 2.86–2.74 (m, 2H), 2.64–2.49 (m, 1H), 2.39–2.17 (m, 3H), 2.02–1.78 (m, 3H), 1.65–1.19 (m, 4H), 0.85 (s, 3H). $^{13}$C NMR (75 MHz, CDCl$_3$) δ 162.2, 144.9, 143.8, 132.3, 130.0, 115.0, 108.5, 101.2, 77.6, 56.5, 53.9, 44.7, 39.2, 36.2, 29.9, 29.5, 28.1, 27.3, 24.3, 19.0. Anal ($C_{20}H_{26}O_2$) calcd C=80.48, H=8.79, found C=80.60, H=8.77.

EXAMPLE 32

2-methoxy-19-norpregna-1,3,5(10)17(20)-tetraene-3-ol (Table 1, Entry 12)

Reaction conditions as above except reaction scale was doubled and ethyl triphenylphosphonium bromide was used, from 2-methoxyestrone (613 mg, 2.04 mmol) obtain 540 mg (1.73 mmol, 84% yield) of final product. Selected spectral data: $^1$H NMR (300 MHz, CDCl$_3$) δ 6.82 (s, 1 H), 6.67 (s, 1 H), 5.44 (s, 1 H), 5.23–5.07 (m, 1 H), 3.88 (s, 3 H), 2.86–2.72 (m, 2 H), 2.51–2.38 (m, 2 H), 2.38–2.17 (m, 3 H), 1.99–1.88 (m, 1 H), 1.83–1.68 (m, 4 H), 1.49–1.20 (m, 5 H), 0.94 (s, Z isomer) and 0.80 (s, E isomer, total 3H, ratio 5:1 respectively). $^{13}$C NMR (75 MHz, CDCl$_3$) δ153.0 (E isomer) and 150.7 (Z isomer), 145.0, 143.8, 132.4, 130.0, 115.0, 113.8, 110.6 (Z isomer) and 108.4 (E isomer), 56.5, 55.6, 54.1, 45.0 (Z isomer) and 44.5 (E isomer), 39.0 (E isomer) and 38.7 (Z isomer), 37.7 (Z isomer) and 36.6 (E isomer), 31.9, 29.5, 28.1 (E isomer) and 28.0 (Z isomer), 27.7 (Z isomer) and 27.4 (E isomer), 24.5 (Z isomer) and 24.4 (E isomer), 19.5 (E isomer) and 17.4 (Z isomer), 14.0 (E isomer) and 13.6 (Z isomer). Anal ($C_{21}H_{28}O_2$) calcd C=80.73 H=8.79 found C=80.60 H=8.77.

EXAMPLE 33

Preparation of 2-methoxy-17(20)-Z-propylideneestra-1,3,5(10)-triene-3-ol

Reaction conditions as above except reaction scale was doubled and propyl triphenylphosphonium bromide was used, from 2-methoxyestrone (614.2 mg, 2.04 mmol) obtain 358.9 mg (1.10 mmol, 54% yield) of final product. Selected spectral data: $^1$H NMR (300 MHz, CDCl$_3$) δ 6.81 (s, 1 H), 6.66 (s, 1 H), 5.44 (s, 1 H), 5.07 (t, J=7.4 Hz, 1 H), 3.88 (s, 3 H), 2.88–2.71 (m, 2 H), 2.53–2.04 (m, 6 H), 2.00–1.87 (m, 1 H), 1.76 (t, J=9.9, 12 Hz, 2 H), 1.49–1.18 (m, 6 H), 0.99 (t, J=7.5 Hz, 3 H), 0.94 (s, Z isomer) and 0.81 (s, E isomer, total 3 H, Z/E ratio 5:1 respectively). $^{13}$C NMR (75 MHz, CDCl$_3$) δ151.5 (E isomer) and 149.2 (Z isomer), 145.0, 143.8, 132.4, 130.0, 122.3 (Z isomer) and 118.6 (E isomer), 115.0, 108.4, 56.5, 55.7 (Z isomer) and 54.0 (E isomer), 45.0 (Z isomer) and 44.9 (E isomer), 44.5 (Z isomer) and 44.2 (E isomer), 39.1 (E isomer) and 38.8 (Z isomer), 37.7 (Z isomer) and 36.6 (E isomer), 31.9, 29.5, 28.2 (E isomer) and 28.0 (Z isomer), 27.7 (Z isomer) and 27.4 (E isomer), 26.7 (E isomer) and 24.5 (Z isomer), 22.2 (E isomer) and 21.3 (Z isomer), 19.5 (E isomer) and 17.9(Z isomer), 15.8 (Z isomer) and 14.7 (E isomer). Anal ($C_{22}H_{30}O_2$) calcd C=80.94, H=9.26, found C=80.71, H=9.30.

EXAMPLE 34

Preparation of 2-methoxy-17(20)-Z-butylideneestra-1,3,5(10)-triene-3-ol (Table 1, Entry 15)

Reaction conditions as above except reaction scale was doubled and butyl triphenylphosphonium bromide was used, from 2-methoxyestrone (593.6 mg, 1.97 mmol) obtain 532.1 mg (1.56 mmol, 79% yield) of final product. Selected spectral data: $^1$H NMR (300 MHz, CDCl$_3$) δ 6.82 (s, 1 H), 6.66 (s, 1 H), 5.43 (s, 1 H), 5.08 (t, J=7.4 H), 3.88 (s, 3 H), 2.81–2.77 (m, 2 H), 2.54–2.01 (m, 7 H), 1.99–1.87 (m, 1 H), 1.76 (app t, J=9.6, 12.6 Hz, 2 H), 1.49–1.26 (m, 6 H), 0.97–0.89 (m, $H_{18}$ of Z isomer and terminal butyl methyl) and 0.80 (s, $H_{18}$ of E isomer, total 6 H, Z/E ratio 9:1 respectively determined by subtracting out terminal methyl of butyl chain in integration) $^{13}$C NMR (75 MHz, CDCl$_3$) δ 152.2 (E isomer) and 149.8 (Z isomer), 145.0, 143.8, 132.4, 130.0, 120.5 (Z isomer) and 116.7 (E isomer), 115.0, 108.4, 56.5, 55.7 (Z isomer) and 54.1 (E isomer), 44.9, 44.5 (Z isomer) and 44.3(E isomer), 39.1 (E isomer) and 38.8 (Z isomer), 37.8 (Z isomer) and 36.6 (E isomer), 32.0, 31.0 (E isomer) and 30.1 (Z isomer), 29.5, 28.2 (E isomer) and 28.0 (Z isomer), 27.7 (Z isomer) and 27.4 (E isomer), 24.5, 24.3 (Z isomer) and 23.3 (E isomer), 19.6 (E isomer) and 17.9 (Z isomer), 14.4. Anal ($C_{23}H_{32}O_2$) calcd C=81.13, H=9.47, found C=81.32, H=9.55.

EXAMPLE 35

Representative Procedure for Preparation of 17-alkyl-2-methoxyestradiol Analogs 2-methoxy-17β-methylestra-1,3,5(10)-triene-3-ol (Table 1, Entry 8)

17-Methylene analog (471.9 mg, 1.58 mmol) was dissolved ethyl acetate (20 ml). Pd/C 10% (47.5 mg) was added and reaction mixture was then subjected to hydrogenation in Parr hydrogenater for an hour under 30 psi of hydrogen. Reaction mixture was then filtered through Celite and solvent was removed via rotary evaporation to yield 472.5 mg white crystals (1.57 mmol, 99% yield) of the final product 2-methoxy-17β-methylestra-1,3,5(10)-triene-3-ol. Selected spectral data: $^1$H NMR (300 MHz, CDCl$_3$) δ6.82 (s, 1 H), 6.66 (s, 1 H), 5.43 (s, 1 H), 3.88 (s, 3 H), 2.85–2.70 (m, 2 H), 2.32–2.15 (m, 2 H), 1.94–1.68 (m, 4 H), 1.52–1.12 (m, 8 H), 0.90 (d, J=6.9 Hz, 3 H), 0.61 (s, 3 H). $^{13}$C NMR (75 MHz, CDCl$_3$) δ144.90, 143.75, 132.65, 130.11, 114.99, 108.51, 56.46, 55.21, 45.58, 44.85, 42.74, 39.39, 37.97, 30.65, 29.52, 28.38, 27.21, 24.83, 14.34, 12.44. Anal (C$_{20}$H$_{28}$O$_2$) calcd C=79.96 H=9.39 found C=79.98 H=9.49.

EXAMPLE 36

2-methoxy-17β-ethylestra-1,3,5(10)-triene-3-ol (Table 1, Entry 13)

Reaction conditions as above, from olefin (435.7 mg, 1.39 mmol) obtain 395.8 mg (1.26 mmol, 91% yield) of final product. Selected spectral data: $^1$H NMR (300 MHz, CDCl$_3$) δ 6.82 (s, 1 H), 6.66 (s, 1 H), 5.43 (s, 1 H), 3.88 (s, 1 H), 2.78 (app t, J=10.2, 4.5 Hz, 3 H), 2.30–2.15 (m, 2 H), 2.00–1.82 (m, 3 H), 1.79–1.69 (m, 1 H), 1.62–1.08 (m, 11 H), 0.92 (app t, J=7.5, 6.6 Hz, 3 H), 0.63 (s, 3 H). $^{13}$C NMR (75 MHz, CDCl$_3$) δ 144.90, 143.74, 132.66, 130.10, 114.98, 108.49, 56.45, 55.36, 53.58, 44.91, 42.85, 39.19, 38.47, 29.51, 28.65, 28.35, 27.24, 24.67, 23.57, 13.78, 12.95. Anal (C$_{21}$H$_{30}$O$_2$) calcd C=80.21, H=9.62, found C=79.95, H=9.71.

EXAMPLE 37

2-methoxy-17,β-propylestra-1,3,5(10)-triene-3-ol (Table 1, Entry 7)

Reaction conditions as above, from olefin (269.5 mg, 0.83 mmol) obtain 258.4 mg (0.79 mmol, 95% yield) of final product. Selected spectral data: $^1$H NMR (300 MHz, CDCl$_3$) δ6.82 (s, 1 H), 6.66 (s, 1 H), 5.43 (s, 1 H), 3.88 (s, 3 H), 2.84–2.70 (m, 2 H), 2.31–2.16 (m, 2 H), 1.97–1.67 (m, 4 H), 1.52–1.06 (m, 12 H), 0.93 (t, J=6.7 Hz, 3 H), 0.63 (s, 3 H). $^{13}$C NMR (75 MHz, CDCl$_3$) δ144.91, 143.75, 132.66, 130.10, 115.00, 108.50, 56.46, 55.31, 51.34, 44.92, 42.83, 39.21, 38.41, 33.15, 29.52, 28.98, 28.37, 27.24, 24.77, 22.39, 15.06, 12.97. Anal (C$_{22}$H$_{32}$O$_2$) calcd C=80.44, H=9.82, found C=80.20, H=9.86.

EXAMPLE 38

2-methoxy-17β-butylestra-1,3,5(10)-triene-3-ol (Table 1, Entry 16)

Reaction conditions as above, from olefin (478.8 mg, 1.41 mmol) obtain 430.5 mg (1.26 mmol, 90% yield) of final product. Selected spectral data: $^1$H NMR (300 MHz, CDCl$_3$) δ 6.82 (s, 1 H), 6.66 (s, 1 H), 5.43 (s, 1 H), 3.89 (s, 3 H), 2.78 (app t, J=10.8, 4.5 Hz, 2 H), 2.30–2.16 (m, 2 H), 1.96–1.83 (m, 3 H), 1.79–1.69 (m, 1 H), 1.51–1.07 (m, 15 H), 0.92 (t, J=9, 6.9 Hz, 4 H), 0.63 (s, 3 H). $^{13}$C NMR (75 MHz, CDCl$_3$) δ 144.90, 143.74, 132.66, 130.09, 114.99, 108.48, 56.46, 55.31, 51.52, 44.92, 42.84, 39.20, 38.42, 31.56, 30.49, 29.52, 29.02, 28.36, 27.23, 24.75, 23.63, 14.60, 12.96. Anal (C$_{23}$H$_{34}$O$_2$) calcd C=80.65, H=10.01, found C=80.90, H=10.10.

EXAMPLE 39

2-acetylestra-1,3,5(10)-triene-3,17β-diol (Table 1, Entry 6)

Selected spectral data: $^1$H NMR (300 MHz, CDCl$_3$) δ7.62 (s, 1H), 6.71 (s, 1H), 4.78 (s, 1H), 3.73 (t, J=8 Hz, 1H), 2.94 (m, 2H), 2.62 (s, 3H), 0.85 (s, 3H). $^{13}$C NMR (75 MHz, CDCl$_3$) δ 204.4, 160.4, 147.7, 132.0, 127.6, 118.2, 118.0, 86.2, 50.4, 43.9, 43.4, 38.8, 37.8, 30.3, 28.5, 27.2, 26.9, 26.7, 23.5, 12.2. Anal (C$_{20}$H$_{26}$O$_3$) calcd C=76.39, H=8.34, found C=76.31, H=8.20.

EXAMPLE 40

2-formylestra-1,3,5(10)-triene-3,17β-diol (Table 2, Entry 3)

Selected spectral data: $^1$H NMR (300 MHz, CDCl$_3$, drop CD$_3$OD) δ9.79 (s, 1H), 7.42 (s, 1H), 6.68 (s, 1H), 3.75–3.63 (m, 1H), 2.91–2.82 (m, 2H), 0.77 (s, 3H). $^{13}$C NMR (75 MHz, CDCl$_3$) δ 196.6, 159.3, 148.6, 133.2, 131.0, 119.3, 117.2, 58.4, 43.7, 43.5, 38.8, 36.8, 30.6, 30.5, 27.1, 26.6, 23.4, 18.5, 11.4. Anal (C$_{19}$H$_{24}$O$_3$) calcd C=75.96 H=8.06 found C=75.70 H=8.26.

EXAMPLE 41

2-nitroestra-1,3,5(10)-estratriene-3,17,β-diol (Table 2, Entry 7)

Selected spectral data: $^1$H NMR (300 MHz, CDCl$_3$) δ 10.43 (s, 1H), 8.00 (s, 1H), 6.86 (s, 1H), 3.75 (t, J=8 Hz, 1H), 3.00–2.80 (m, 2H), 0.80 (s, 3H). $^{13}$C NMR (300 MHz, CDCl$_3$) δ153.2, 149.6, 134.2, 132.1, 121.9, 119.3, 82.1, 50.4, 43.8, 43.6, 38.6, 36.7, 30.9, 30.2, 27.0, 26.5, 23.5, 11.4. Anal (C$_{18}$H$_{23}$NO$_4$) calcd C=68.12 H=7.30 N=4.41 found C=67.85 H=7.29 N=4.40.

EXAMPLE 42

2-aminoestra-1,3,5(10)-triene-3-ol (Table 2, Entry 9)

Selected spectral data: $^1$H NMR (300 MHz, CD$_3$OD) δ 6.68 (s, 1H), 6.45 (s, 1H), 3.68 (t, J=8 Hz, 1H), 0.75 (s, 1H). $^1$H NMR (75 MHz, CD$_3$OD) δ143.7, 132.1, 131.7, 127.6, 114.7, 114.0, 81.5, 50.3, 43.4, 39.6, 37.1, 29.7, 29.1, 27.8, 26.7, 23.0, 21.9, 10.7. Anal (C$_{18}$H$_{25}$NO$_2$1/3H$_2$O) calcd C=73.68 H=8.84 N=4.78 found C=73.77 H=8.73, N=4.39.

EXAMPLE 43

2-ethoxyestra-1,3,5(10)-triene-3-ol (Table 2, Entry 18)

Selected spectral data: $_1$H NMR (300 MHz, CDCl$_3$, drop CD$_3$OD) δ 6.77 (s, 1H), 6.62 (s, 1H), 4.11 (m, 2H), 3.69 (t, J=8 Hz, 1H), 2.80–2.63 (m, 2H), 1.41 (t, J=7 Hz, 3H), 0.76

(s, 3H). $^{13}$C NMR (300 MHz, CDCl$_3$) δ 144.3, 144.0, 132.1, 129.9, 115.0, 109.9, 65.150.4, 44.6, 43.6, 39.2, 37.1, 30.7, 29.3, 27.7, 27.0, 23.4, 15.3, 11.4. Anal (C$_{20}$H$_{28}$O$_3$ 3/4 H$_2$O) calcd C=72.80 H=9.01 found C=72.51 H=8.60.

EXAMPLE 44

2-methoxyestra-1,3,5(10)9(11)-tetraene-3,17,β-diol
(Table 4)

Selected spectral data: $^1$H NMR (300 MHz, CDCl$_3$, drop CD$_3$OD) δ 7.08 (s, 1H), 6.63 (s, 1H), 6.08 (s, 1H), 3.90 (s, 3H), 3.82 (t, J=8 Hz, 1H), 2.88–2.65 (m, 2H), 0.81 (s, 3H). $^{13}$C NMR (75 MHz, CDCl$_3$) δ 145.7, 145.2, 135.9, 130.0, 126.9, 117.6, 115.0, 106.5, 82.2, 56.3, 47.8, 41.9, 39.3, 39.1, 30.9, 29.5, 28.8, 24.3, 11.4. Anal (C$_{19}$H$_{24}$O$_3$1/4H$_2$O) calcd C=74.85 H=8.10 found C=74.70 H=7.89.

EXAMPLE 45

17,β-aminoestra-1,3,5(10)-triene-3-ol
(Table 1, Entry 4)

Selected spectral data: $^1$H NMR (300 MHz, CD$_3$OD) δ 6.8 (s, 1H), 6.64 (s, 1H), 3.86 (s, 3H), 2.83–2.69 (m 2H), 0.69 (s, 3H).: $^{13}$C NMR (75 MHz, CDCl$_3$) δ 145.0, 143.8 132.2, 130.0, 115.0, 108.6, 63.0, 56.5, 52.4, 44.7, 43.3, 39.4, 37.1, 31.6, 29.4, 27.9, 27.0, 23.7, 11.5. Anal (C$_{19}$H$_{27}$NO$_2$) calcd C=75.70 H=9.05 N=4.65 found C=75.66 H=9.02, N=4.64.

EXAMPLE 46

17-α-hydroxy-2-methoxyestradiol
(Table 2, Entry 2)

Selected spectral data: $^1$H NMR (300 MHz, CDCl$_3$) δ 6.83 (s, 1H), 6.67 (s, 1H), 5.44 (s, 1H), 3.88 (s, 3H), 3.83 (d, J=6 Hz, 1H), 2.84–2.75 (m, 2H), 2.41–2.16 (m, 3H), 1.97–1.21 (m, 10H), 0.73 (s, 3H). $^{13}$C NMR (75 MHz, CDCl$_3$) δ 145.0, 143.8, 132.3, 130.0, 115.0, 108.5, 80.5, 56.5, 48.1, 46.0, 44.3, 39.5, 32.9, 31.9, 29.5, 28.6, 27.0, 24.7, 17.5. Anal (C$_{19}$H$_{26}$O$_3$) calcd C=75.46, H=98.67, found C=75.18, H=8.70

EXAMPLE 47

Synthesis of 2-Alkylamino-17-deoxyestrone Analogs

2-Alkylamino-17-deoxyestrone Analogs were synthesized as depicted in Scheme-8.

EXAMPLE 48

Synthesis of estra-1,3,5(10)-triene-3-ol

Into a stirring suspension of estrone (8.1 g, 30 mmols) in 60 mL diethylene glycol, 20 mL 1-butanol and 2 mL hydrazine anhydrous (60 mmols) were added. The reaction mixture was heated under reflux for 1 hour to get clear solution. After cooling reaction mixture to 50° C., 5.04 g KOH pellets (90 mmols) were added and butanol was distilled. The reaction mixture was heated at 50° C. for 2 hours and then cooled to RT. On pouring in to ice (50 g), 20 mL 6N HCl was added and reaction mixture stirred to give white solid product. The product was separated by filtration, washed with cold water and dried under vac. to give 7.5 g (90%) product. The product was purified on silica gel column eluted with CHCl$_3$/MeOH 99:1. $^1$H NMR in CDCl$_3$ confirmed the product as estra-1,3,5(10)-triene-3-ol.

EXAMPLE 49

Synthesis of 2-Nitroestra-1,3,5(10)-triene-3-ol

Into a solution of estra-1,3,5(10)-triene-3-ol (760 mg, 3 mmols) in 20 mL acetic acid glacial, 0.19 mL (3 mmols) of conc. HNO$_3$ was added at 20° C. The temperature of reaction mixture was raised to RT and stirred for 18 hour. The reaction mixture was diluted with water and products were extracted with ethyl ether. The ether layer was washed with water and brine and dried over CaSO$_4$ anhydrous, filtered and evaporated to give yellow solid. The product was purified on flash silica gel column eluted with Hex/CH$_2$CL$_2$ 4:1 mixture to give yellow crystal product (400 mg, 55%). $^1$H NMR in CDCl$_3$ confirmed the product as 2-Nitroestra-1,3,5(10)-triene-3-ol.

EXAMPLE 50

Synthesis of 2-aminoestra-1,3,5(10)-triene-3-ol

2-Nitroestra-1,3,5(10)-triene-3-ol (301 mg, 1.0 mmols) was dissolved in 30 mL dioxane/methanol 1:3 mixture and was hydrogenated in Parr hydrogenater at 40 psi of hydrogen in the presence of Pd/C 10% (200 mg) for 4 hours[1]. After filtering the reaction mixture through Celite filtering agent the solvents were evaporated under vacuum to give white crystals (240 mg, 95%). $^1$H NMR in CDCl$_3$ confirmed the product as 2-aminoestra-1,3,5(10)-triene-3-ol.

EXAMPLE 51

Synthesis of
2-N,N-Dimethylaminoestra-1,3,5(10)-triene-3-ol 2-nitroestra-1,3,5(10)-triene-3-ol (170 mg, 0.5 mmols) was dissolved in 30 mL dioxane/methanol 1:5 mixture and after adding 0.4 mL formaldehyde (37%) was hydrogenated in Parr hydrogenated at 40 psi of hydrogen in the presence of Pd/C 10% (200 mg) for 4 hours. After filtering the reaction mixture through Celite filtering agent the solvents were evaporated under vacuum to give white powder. The product was purified on flash silica gel column eluted with CHCl$_3$/MeOH 95:5 mixture to give white solid product (140 mg, 95%). $^1$H NMR in CDCl$_3$ confirmed the product as 2-N,N-Dimethylaminoestra-1,3,5(10)-triene-3-ol.

EXAMPLE 52

Synthesis of
2-N-Formamidestra-1,3,5(10)-triene-3-ol

Into a hot solution of 2-amino-17-deoxyestrone (135 mg, 0.5 mmols) in 5 mL toluene, 0.2 mL of formic acid was added[2]. The temperature of reaction mixture was raised to boil and the azotropic mixture of tol./water was collected and then toluene was slowly distilled over a period of one hour. When 1/3 toluene was distilled the reaction mixture was cooled to RT to give white crystals of 2-N-Formamide-17-deoxyestrone (100 mg, 75%). $^1$H NMR in CDCl$_3$ confirmed the product as 2-N-formamidestra-1,3,5(10)-triene-3-ol.

EXAMPLE 53

Synthesis of 2-N-Methylaminoestra-1,3,5(10)-triene-3-ol

Into solution of $AlH_3$ (5 mmols) (formed in-situ)[3] in 15 mL THF anhydrous, 2-N-formamidestra-1,3,5(10)-triene-3-ol (150 mg, 0.5 mmols) in 5 mL THF was added at RT and stirred for 2 h. After adding 0.4 mL THF/$H_2O$ 1:1 mixture drop wise, 1.5 mL 15% NaOH solution was added and suspension was stirred for 20 min. After diluting with 20 mL ethyl ether $AlOH_3$ PPT were separated by filtration. After evaporating solvents the product was purified on flash silica gel column eluted with Hex/ether 1:1 mixture to give white solid product (120 mg, 70%). $^1$H NMR in $CDCl_3$ confirmed the product as 2-N-Methylaminoestra-1,3,5(10)-triene-3-ol.

EXAMPLE 54

Synthesis of 3-Azidoestra-1,3,5(10)-triene-3-ol

Into a solution of 2-amino-estradiol (144 mg, 0.5 mmols) in 3 mL acetic acid glacial, a solution of sodium nitrite (48 mg, 0.7 mmols) in 1 mL water was added at 0° C. The color of the reaction mixture changed to orange-yellow. After stirring at 0° C. for 30 min. a solution of sodium azide (45 mg, 0.7 mmols) in water was added. The color of the reaction mixture changed to orange-red. Temperature was maintained at 0° C. for 30 min. and then raised to RT. After stirring for one hour, the solvents were evaporated under vac. and remaining solid was dissolved in chloroform. The chloroform layer was washed with water and brine and dried over $CaSO_4$ anhydrous, filtered and evaporated to give light brown foamy solid. The product was purified by flash silica gel column eluted with $CHCl_3$/MeOH. 99:1 mixture to give 100 mg light yellow foamy solid (70%). IR and $^1$H NMR in $CDCl_3$ confirmed the product as 3-Azidoestra-1,3,5(10)-triene-3-ol.

References for examples 31–54 include: Org. Synt. Coll. Vol. 5, 552; Org. Synt. Coll. Vol. 3, 590; and Shah, et. al. *J. Med. Chem.* 1995, 38, 4284.

All of the publications mentioned herein are hereby incorporated by reference in their entireties. The above examples are merely demonstrative of the present invention, and are not intended to limit the scope of the appended claims.

What is claimed is:

1. A compound of the general formula:

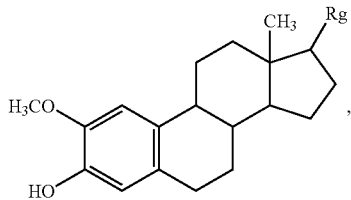

wherein, Rg is selected from =NOH, —NHCH$_2$CH$_2$CH$_3$, =N—NH—(SO$_2$)—C$_6$H$_4$—p—CH$_3$, —COOH and —CH$_2$OH.

2. A pharmaceutical preparation comprising:
   (a) the compound of claim 1; and
   (b) a pharmaceutically acceptable carrier, excipient or diluent.

* * * * *